(12) United States Patent
Takaoka et al.

(10) Patent No.: US 7,199,139 B2
(45) Date of Patent: Apr. 3, 2007

(54) MEDICINAL COMPOSITIONS CONTAINING DIURETIC AND INSULIN RESISTANCE-IMPROVING AGENT

(75) Inventors: Masaya Takaoka, Shizuoka (JP); Kazushi Araki, Kamakura (JP); Shoichi Kanda, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 27 days.

(21) Appl. No.: 10/606,632

(22) Filed: Jun. 26, 2003

(65) Prior Publication Data
US 2004/0053974 A1 Mar. 18, 2004

Related U.S. Application Data

(63) Continuation-in-part of application No. PCT/JP01/11296, filed on Dec. 21, 2001.

(30) Foreign Application Priority Data
Dec. 26, 2000 (JP) ............................. 2000-394424

(51) Int. Cl.
*A61K 31/44* (2006.01)
(52) U.S. Cl. .................................. 514/342
(58) Field of Classification Search ................ 514/369, 514/342
See application file for complete search history.

(56) References Cited

U.S. PATENT DOCUMENTS

| | | | |
|---|---|---|---|
| 4,687,777 A | 8/1987 | Meguro et al. | |
| 4,897,393 A | 1/1990 | Iijima et al. | |
| 5,002,953 A | 3/1991 | Hindley | |
| 5,457,109 A | 10/1995 | Antonucci et al. | |
| 5,594,016 A | 1/1997 | Ueno et al. | |
| 5,643,931 A | 7/1997 | Niigata et al. | |
| 5,693,651 A | 12/1997 | Nomura et al. | |
| 5,728,720 A | 3/1998 | Shinkai | |
| 5,886,014 A | 3/1999 | Fujita et al. | |
| 6,030,990 A | 2/2000 | Maeda et al. | |
| 6,103,907 A * | 8/2000 | Yanagisawa et al. | ....... 546/329 |
| 6,528,525 B1 | 3/2003 | Yanagisawa et al. | |
| 6,596,751 B2 | 7/2003 | Fujita et al. | |
| 2002/0013334 A1 * | 1/2002 | Robl et al. | ........... 514/291 |
| 2003/0073729 A1 * | 4/2003 | Kitahara et al. | ........... 514/369 |

FOREIGN PATENT DOCUMENTS

| | | |
|---|---|---|
| EP | 0 745 600 A1 | 12/1996 |
| EP | 745600 A1 | 12/1996 |
| EP | 0 861 831 A1 | 9/1998 |
| EP | 1 180 519 A1 | 2/2002 |
| WO | WO 97/11055 A1 | 3/1997 |
| WO | WO 97/31907 A1 | 9/1997 |
| WO | WO 99/19313 A1 | 4/1999 |
| WO | WO 99/62872 A1 | 12/1999 |
| WO | WO 00/61127 A2 | 10/2000 |
| WO | WO 01/17513 A2 | 3/2001 |
| WO | WO 01/21602 A1 | 3/2001 |
| WO | WO 01/47509 A2 | 7/2001 |

OTHER PUBLICATIONS

Mizukami J, Taniguchi T., "The antidiabetic agent thiazolidinedione stimulates the interaction between PPAR gamma and CBP", Biochem Biophys Res Commun. Nov. 7, 1997;240(1):61-4.*

Fukui Y, et. al., "A new thiazolidinedione, NC-2100, which is a weak PPAR-gamma activator, exhibits potent antidiabetic effects and induces uncoupling protein 1 in white adipose tissue of KKAy obese mice", Diabetes. May 2000;49(5):759-67.*

Devasthale et. al., "Design and synthesis of N-[(4-methoxyphenoxy)carbonyl]-N-[[4-[2-(5- methyl-2-phenyl-4-oxazolyl)ethoxy]phenyl]methyl]glycine [Muraglitazar/BMS-298585], a novel peroxisome proliferator-activated receptor alpha/gamma dual agonist with effacious glucose and lipid-lowering activities", J Med Chem. Mar. 24, 2005;48(6):2248-50.*

Hosokawa, et al., "Troglitazone Inhibits Bicarbonate Secretion in Rat and Human Duodenum[1]", *Journal of Pharmacology and Experimental Therapeutics, The American Society for Pharmacology and Experimental Therapeutics*, Sep. 1999, pp. 1080-1084, XP008002057, ISSN: 0022-3565, vol. 3, No. 290, USA.

Dagogo-Jack, et al., "Pathophysiology of Type 2 Diabetes and Modes of Action of Therapeutic Interventions", *Archives of Internal Medicine, American Medical Association*, Sep. 8, 1997, pp. 1802-1817, XP000872498, ISSN: 0003-9926 vol. 157, No. 16, Chicago, IL.

Gilbert et al., "Drug Administration in Patients with Diabetes Mellitus-Safety Considerations", *Drug Safety*, (1998), pp. 441-455, vol. 18, No. 6, XP001041098, ISSN: 0114-5916, Adis Press, Auckland NZ.

Hosokawa, et al., "Troglitazone Inhibits Bicarbonate Secretion in Rat and Human Duodenum[1]", Journal of Pharmacology and Experimental Therapeutics, The American Society for Pharmacology and Experimental Therapeutics, Sep. 1999, pp. 1080-1084, XP008002057, ISSN: 0022-3565, vol. 3, No. 290, USA.

Dagogo-Jack, et al., "Pathophysiology of Type 2 Diabetes and Modes of Action of Therapeutic Interventions", Archives of Internal Medicine, American Medical Association, Sep. 8, 1997, pp. 1802-1817, XP000872498, ISSN: 0003-9926 vol. 157, No. 16, Chicago, IL Gilbert et al., "Drug Administration in Patients with Diabetes Mellitus-Safety Considerations" Drug Safety, (1998), pp. 441-455, vol. 18, No. 6, XP001041098, ISSN: 0114-5916, Adis Press, Auckland NZ.

* cited by examiner

*Primary Examiner*—Brian-Yong S. Kwon
*Assistant Examiner*—Nancy Zhang
(74) *Attorney, Agent, or Firm*—Frishauf, Holtz, Goodman & Chick, P.C.

(57) ABSTRACT

The present invention relates to a pharmaceutical composition comprising an insulin sensitizer and a diuretic which can prevent or treat side effects such as edema, cardiac enlargement, body fluid retention or hydrothorax caused by administration of an insulin sensitizer.

1 Claim, 2 Drawing Sheets

MEDICINAL COMPOSITIONS CONTAINING DIURETIC AND INSULIN RESISTANCE-IMPROVING AGENT

This is a Continuation-in-Part Application of International Application PCT/JP01/11296 filed Dec. 21, 2001, which is incorporated herein by reference in its entirety.

BACKGROUND OF THE INVENTION

The present invention relates to new pharmaceutical agents for prophylaxis or treatment of diabetes mellitus comprising an insulin sensitizer and a diuretic, said diuretic having the activity of preventing or treating edema caused by the insulin sensitizer.

It is known that insulin sensitizers are useful as agents for the prevention and/or treatment of diabetes mellitus. However, it is also known that insulin sensitizers sometimes elicit adverse events such as increase in heart-weight, cardiac enlargement, edema, hydrothorax and the like, when used clinically. These adverse events are considered to be associated with retention of body fluid due to increased sensitivity to insulin. On the other hand, diuretics are agents that promote excretion of excess body fluid (hydrothorax, plasma, etc.) as urine. When diuretics are co-administered with insulin sensitizers, adverse events such as increase in heart-weight, cardiac enlargement, edema, hydrothorax, which are related to retention of body fluid, are expected to be suppressed by preventing such retention.

Loop diuretics are known to produce more potent diuretic action than other diuretics. On the other hand, epithelial $Na^+$ channel (ENaC) blockers are used with a combination of other diuretics, because their diuretic action is mild.

BRIEF SUMMARY OF THE INVENTION

A pharmaceutical composition of a diuretic and insulin sensitzer for prophylaxis or treatment of diabetes mellitus.

DETAILED DESCRIPTION OF THE INVENTION

Figure 1:
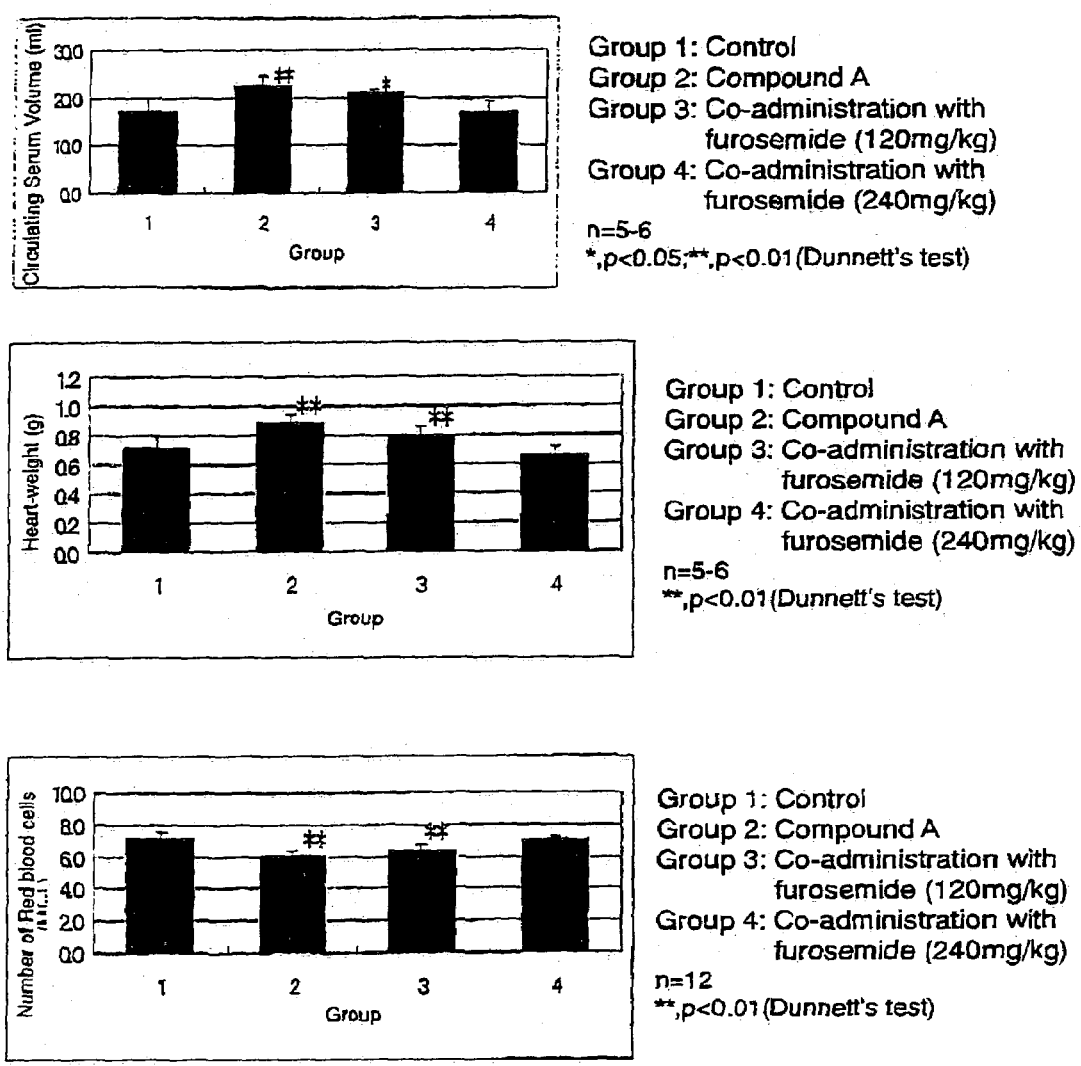
FIG. 1 represents the results of experiments that indicate that increases in serum volume, heart-weight and edema elicited by 5-[4-(6-methoxy-1-methyl-1H-benzimidazol-2-ylmethoxy)benzyl]thiazolidine-2,4-dione hydrochloride (compound A), are suppressed by co-administration with furosemide (diuretic).

Insulin sensitizers sometimes elicit adverse events such as increase in heart-weight, cardiac enlargement, edema, retention of body fluid, hydrothorax and the like when used clinically.

The present inventors found that increases in heart-weight or the like elicited by some kinds of therapeutic agents for diabetes mellitus (insulin sensitizers) were due to their effects on increasing sensitivity to insulin. Hence the present inventors studied methods for prevention of increase in heart-weight, cardiac enlargement, edema, retention of body fluid, hydrothorax and the like, and found that such adverse events can be prevented by co-administration with a diuretic. Thus they completed their invention.

Regarding the present invention, the "insulin sensitizer" has no limitation as long as the agent improves insulin resistance and enhances sensitivity to insulin.

Examples of insulin sensitizers include such as troglitazone and pioglitazone, rosiglitazone, JTT-501, MCC-555, GI-262570, YM-440, KRP-297, T-174, NC-2100, BMS-298585, AZ-242 and NN-622 represented by the formulae below.

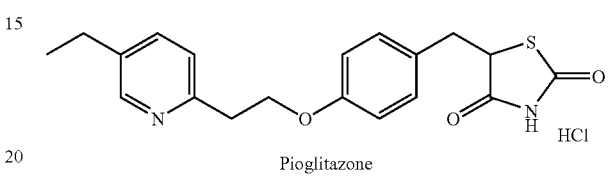

Pioglitazone

Rosiglitazone

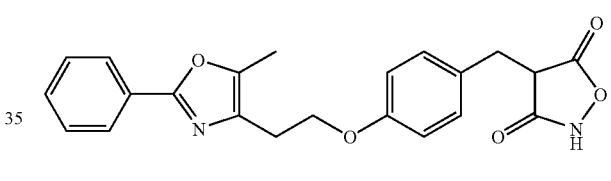

JTT-501

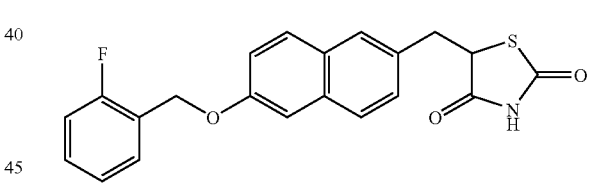

MCC-555

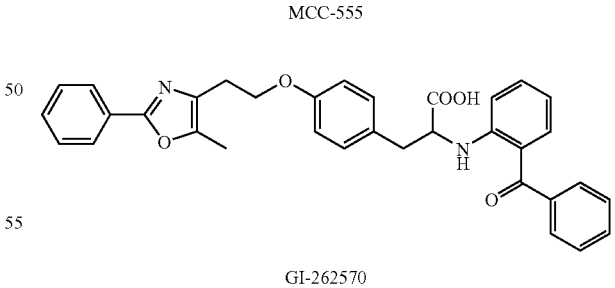

GI-262570

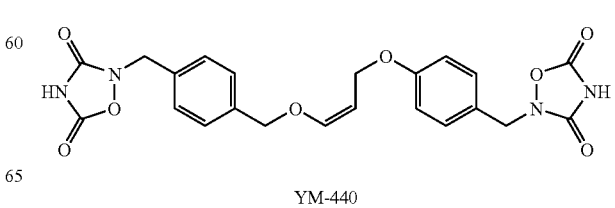

YM-440

-continued

KRP-297

T-174

NC-2100

BMS-298585

AZ-242

NN-622

5-[4-(6-Methoxy-1-methyl-1H-benzimidazol-2-yl-methoxy)benzyl]thiazolidine-2,4-dione or a pharmacologically acceptable salt thereof.

A phenylalkylcarboxylic acid derivative having the general formula (Ia) below:

(Ia)

a pharmacologically acceptable salt thereof or a pharmacologically acceptable ester thereof

[wherein, $R^{1a}$ represents a hydrogen atom or a straight- or branched-chain alkyl group having from 1 to 6 carbon atoms, $R^{2a}$ represents a straight- or branched-chain alkylene group having from 2 to 6 carbon atoms, $R^{3a}$ represents (i) a hydrogen atom, (ii) a straight- or branched-chain alkyl group having from 1 to 6 carbon atoms, (iii) a straight- or branched-chain alkoxy group having from 1 to 4 carbon atoms, (iv) a straight- or branched-chain alkylthio group having from 1 to 4 carbon atoms, (v) a halogen atom, (vi) a nitro group, (vii) a straight- or branched-chain dialkylamino group in which the alkyl groups are the same or different from each other and each has from 1 to 4 carbon atoms, (viii) an aryl group having from 6 to 10 carbon atoms which may have from 1 to 3 substituents $\alpha^a$ mentioned below or (ix) an aralkyl group having from 7 to 12 carbon atoms which may have from 1 to 3 substituents $\alpha^a$ mentioned below on the aryl moiety, $Z^a$ represents a single bond or a straight- or branched-chain alkylene group having from 1 to 6 carbon atoms, $W^a$ represents (i) a straight- or branched-chain alkyl group having from 1 to 6 carbon atoms, (ii) a hydroxyl group, (iii) a straight- or branched-chain alkoxy group having from 1 to 4 carbon atoms, (iv) a straight- or branched-chain alkylthio group having from 1 to 4 carbon atoms, (v) an amino group, (vi) a straight- or branched-chain monoalkylamino group having from 1 to 4 carbon atoms, (vii) a straight- or branched-chain dialkylamino group in which the alkyl groups are the same or different from each other and each has from 1 to 4 carbon atoms, (viii) an N-alkyl-N-arylamino group having a straight- or branched-chain alkyl group having from 1 to 4 carbon atoms and an aryl group having from 6 to 10 carbon atoms which may have from 1 to 3 substituents $\alpha^a$ mentioned below on the aryl moiety, (ix) an aryl group having from 6 to 10 carbon atoms which may have from 1 to 3 substituents $\alpha^a$ mentioned below, (x) an aryloxy group having from 6 to 10 carbon atoms which may have from 1 to 3 substituents $\alpha^a$ mentioned below on the aryl moiety, (xi) an arylthio group having from 6 to 10 carbon atoms which may have from 1 to 3 substituents $\alpha^a$ mentioned below on the aryl moiety, (xii) an arylamino group having from 6 to 10 carbon atoms which may have from 1 to 3 substituents $\alpha^a$ mentioned below on the aryl moiety, (xiii) an aralkyl group having from 7 to 12 carbon atoms which may have from 1 to 3 substituents $\alpha^a$ mentioned below on the aryl moiety, (xiv) an aralkyloxy group having from 7 to 12 carbon atoms which may have from 1 to 3 substituents $\alpha^a$ mentioned below on the aryl moiety, (xv) an aralkylthio group having from 7 to 12 carbon atoms which may have from 1 to 3 substituents $\alpha^a$ mentioned below on the aryl moiety, (xvi) an aralkylamino group having from 7 to 12 carbon atoms which may have from 1 to 3 substituents $\alpha^a$ mentioned below on the aryl moiety, (xvii) a 1-pyrrolyl group, (xviii) a 1-pyrrolidinyl group, (xix) a 1-imidazolyl group, (xx) a piperidino group or (xxi) a morpholino group, $X^a$ represents an aryl group having from 6 to 10 carbon atoms which may have from 1 to 3 substituents $\alpha^a$ mentioned below or a 5- to 10-membered monocyclic or bicyclic heteroaromatic group containing from 1 to 4 heteroatoms selected from the group consisting of oxygen, nitrogen and sulfur atoms which may have from 1 to 3 substituents $\alpha^a$ mentioned below, the substituent $\alpha^a$ is selected from the group consisting of (i) a straight- or branched-chain alkyl group having from 1 to 6 carbon atoms, (ii) a straight- or branched-chain halogenated alkyl group having from 1 to 4 carbon atoms, (iii) a hydroxyl group, (iv) a straight- or branched-chain aliphatic acyloxy group having from 1 to 4 carbon atoms, (v) a straight- or branched-chain alkoxy group having from 1 to 4 carbon atoms, (vi) a straight- or branched-chain alkylenedioxy group having from 1 to 4 carbon atoms, (vii) an aralkyloxy group having from 7 to 12 carbon atoms, (viii) a straight- or branched-chain alkylthio group having from 1 to 4 carbon atoms, (ix) a straight- or branched-chain alkylsulfonyl group having from 1 to 4 carbon atoms, (x) a halogen atom, (xi) a nitro group, (xii) a straight- or branched-chain dialkylamino group in which the alkyl groups are the same or different from each other and each has from 1 to 4 carbon atoms, (xiii) an aralkyl group having from 7 to 12 carbon atoms, (xiv) an aryl group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xv) an aryloxy group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xvi) an arylthio group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xvii) an arylsulfonyl group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xviii) an arylsulfonylamino group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms, and the nitrogen atom of the amino moiety may be substituted with a straight- or branched-chain alkyl having from 1 to 6 carbon atoms), (xix) a 5- to 10-membered monocyclic or bicyclic heteroaromatic group containing from 1 to 4 heteroatoms selected from the group consisting of oxygen, nitrogen and sulfur atoms, (xx) a 5- to 10-membered monocyclic or bicyclic heteroaromatic oxy group containing from 1 to 4 heteroatoms selected from the group consisting of oxygen, nitrogen and sulfur atoms, (xxi) a 5- to 10-membered monocyclic or bicyclic heteroaromatic thio group containing from 1 to 4 heteroatoms selected from the group consisting of oxygen, nitrogen and sulfur atoms, (xxii) a 5- to 10-membered monocyclic or bicyclic heteroaromatic sulfonyl group containing from 1 to 4 heteroatoms selected from the group consisting of oxygen, nitrogen and sulfur atoms and (xxiii) a 5- to 10-membered monocyclic or bicyclic heteroaromatic sulfonylamino group containing from 1 to 4 heteroatoms selected from the group consisting of oxygen, nitrogen and sulfur atoms (the nitrogen atom of the amino moiety may be substituted with a straight- or branched-chain alkyl having from 1 to 6 carbon atoms) and $Y^a$ represents an oxygen atom, a sulfur atom or a group of formula: >N—$R^{4a}$ (wherein $R^{4a}$ represents a hydrogen atom, a straight- or branched-chain alkyl group having from 1 to 6 carbon atoms or a straight- or branched-chain aliphatic acyl group having from 1 to 8 carbon atoms or an aromatic acyl group)].

An amidocarboxylic acid derivative having the general formula (Ib) below:

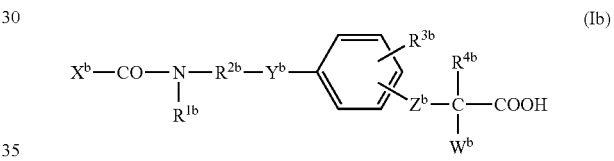

a pharmacologically acceptable salt thereof of a pharmacologically acceptable ester thereof

[wherein, $R^{1b}$ represents a hydrogen atom or a straight- or branched-chain alkyl group having from 1 to 6 carbon atoms, $R^{2b}$ represents a straight- or branched-chain alkylene group having from 1 to 6 carbon atoms, $R^{3b}$ represents (i) a hydrogen atom, (ii) a straight- or branched-chain alkyl group having from 1 to 6 carbon atoms, (iii) a straight- or branched-chain alkoxy group having from 1 to 4 carbon atoms, (iv) a straight- or branched-chain alkylthio group having from 1 to 4 carbon atoms, (v) a halogen atom, (vi) a nitro group, (vii) a straight- or branched-chain dialkylamino group in which the alkyl groups are the same or different from each other and each has from 1 to 4 carbon atoms, (viii) an aryl group having from 6 to 10 carbon atoms which may have from 1 to 3 substituents $\alpha^b$ mentioned below or (ix) an aralkyl group having from 7 to 12 carbon atoms which may have from 1 to 3 substituents $\alpha^b$ mentioned below on the aryl moiety, $R^{4b}$ represents a hydrogen atom or a straight- or branched-chain alkyl group having from 1 to 6 carbon atoms, $Z^b$ represents a single bond or a straight- or branched-chain alkylene group having from 1 to 6 carbon atoms, $W^b$ represents (i) a straight- or branched-chain alkyl group having from 1 to 6 carbon atoms, (ii) a hydroxyl group, (iii) a straight- or branched-chain alkoxy group having from 1 to 4 carbon atoms, (iv) a straight- or branched-chain alkylthio group having from 1 to 4 carbon atoms, (v) an amino group, (vi) a straight- or branched-chain monoalkylamino group having from 1 to 4 carbon atoms, (vii) a straight- or branched-chain dialkylamino group in which the alkyl groups are the same or different from each other and each has from 1 to 4 carbon atoms, (viii) an N-alkyl-N-arylamino group having a straight- or branched-chain alkyl group having from 1 to 4 carbon atoms and an aryl group having from 6 to 10 carbon atoms which may have from 1 to 3 substituents $\alpha^b$ mentioned below on the aryl moiety, (ix) an aryl group having from 6 to 10 carbon atoms which may have from 1 to 3 substituents $\alpha^b$ mentioned below, (x) an aryloxy group having from 6 to 10 carbon atoms which may have from 1 to13 substituents $\alpha^b$ mentioned below on the aryl moiety, (xi) an arylthio group having from 6 to 10-carbon atoms which may have from 1 to 3 substituents $\alpha^b$ mentioned below on the aryl moiety, (xii) an arylamino group having from 6 to 10 carbon atoms which may have from 1 to 3 substituents $\alpha^b$ mentioned below on the aryl moiety, (xiii) an aralkyl group having from 7 to 12 carbon atoms which may have from 1 to 3 substituents $\alpha^b$ mentioned below on the aryl moiety, (xiv) an aralkyloxy group having from 7 to 12 carbon atoms which may have from 1 to 3 substituents $\alpha^b$ mentioned below on the aryl moiety, (xv) an aralkylthio group having from 7 to 12 carbon atoms which may have from 1 to 3 substituents $\alpha^b$ mentioned below on the aryl moiety, (xvi) an aralkylamino group having from 7 to 12 carbon atoms which may have from 1 to 3 substituents $\alpha^b$ mentioned below on the aryl moiety, (xvii) a 1-pyrrolyl group, (xviii) a 1-pyrrolidinyl group, (xix) a 1-imidazolyl group, (xx) a piperidino group or (xxi) a morpholino group, $X^b$ represents an aryl group having from 6 to 10 carbon atoms which may have from 1 to 3 substituents $\alpha^b$ mentioned below or a 5- to 10-membered monocyclic or bicyclic heteroaromatic group containing from 1 to 4 heteroatoms selected from the group consisting of oxygen, nitrogen and sulfur atoms which may have from 1 to 3 substituents $\alpha^b$ mentioned below, the substituent $\alpha^b$ mentioned above is selected from the group consisting of (i) a straight- or branched-chain alkyl group having from 1 to 6 carbon atoms, (ii) a straight- or branched-chain halogenated alkyl group having from 1 to 4 carbon atoms, (iii) a hydroxyl group, (iv) a straight- or branched-chain aliphatic acyloxy group having from 1 to 4 carbon atoms, (v) a straight- or branched-chain alkoxy group having from 1 to 4 carbon atoms, (vi) a straight- or branched-chain alkylenedioxy group having from 1 to 4 carbon atoms, (vii) an aralkyloxy group having from 7 to 12 carbon atoms, (viii) a straight- or branched-chain alkylthio group having from 1 to 4 carbon atoms, (ix) a straight- or branched-chain alkylsulfonyl group having from 1 to 4 carbon atoms, (x) a halogen atom, (xi) a nitro group, (xii) a straight- or branched-chain dialkylamino group in which the alkyl groups are the same or different from each other and each has from 1 to 4 carbon atoms, (xiii) an aralkyl group having from 7 to 12 carbon atoms, (xiv) an aryl group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having-from 1 to 4 carbon atoms), (xv) an aryloxy group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xvi) an arylthio group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xvii) an arylsulfonyl group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), (xviii) an arylsulfonylamino group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms, and the nitrogen atom of the amino moiety may be substituted with a straight- or branched-chain alkyl having from 1 to 6 carbon atoms), (xix) a 5- to 10-membered monocyclic or bicyclic heteroaromatic group containing from 1 to 4 heteroatoms selected from the group consisting of oxygen, nitrogen and sulfur atoms, (xx) a 5- to 10-membered monocyclic or bicyclic heteroaromatic oxy group containing from 1 to 4 heteroatoms selected from the group consisting of oxygen, nitrogen and sulfur atoms, (xxi) a 5- to 10-membered monocyclic or bicyclic heteroaromatic thio group containing from 1 to 4 heteroatoms selected from the group consisting of oxygen, nitrogen and sulfur atoms, (xxii) a 5- to 10-membered monocyclic or bicyclic heteroaromatic sulfonyl group containing from 1 to 4 heteroatoms selected from the group consisting of oxygen, nitrogen and sulfur atoms and (xxiii) a 5- to 10-membered monocyclic or bicyclic heteroaromatic sulfonylamino group containing from 1 to 4 heteroatoms selected from the group consisting of oxygen, nitrogen and sulfur atoms (the nitrogen atom of the amino moiety may be substituted with a straight- or branched-chain alkyl having from 1 to 6 carbon atoms) and $Y^b$ represents an oxygen atom, a sulfur atom or a group of formula: $>N-R^{5b}$ (wherein $R^{5b}$ represents a hydrogen atom, a straight- or branched-chain alkyl group having from 1 to 6 carbon atoms or a straight- or branched-chain aliphatic acyl group having from 1 to 8 carbon atoms or an aromatic acyl group).

An α-substituted carboxylic acid derivative having the general formula (Ic) below:

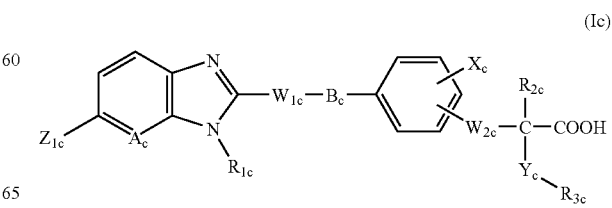

(Ic)

a pharmacologically acceptable ester thereof, a pharmacologically acceptable amide thereof or a pharmacologically acceptable salt thereof

[wherein, $R_{1c}$, $R_{2c}$ and $R_{3c}$ are the same or different, and each represents (i) a hydrogen atom, (ii) a $C_1$–$C_6$ alkyl group, (iii) a $C_6$–$C_{10}$ aryl group (optionally having from 1 to 5 substituents $\alpha_{1c}$ mentioned below), (iv) a $C_7$–$C_{16}$ aralkyl group (optionally having from 1 to 5 substituents $\alpha_{1c}$ mentioned below on the aryl moiety), (v) a $C_1$–$C_6$ alkylsulfonyl group, (vi) a $C_1$–$C_6$ halogenoalkylsulfonyl group, (vii) a $C_6$–$C_{10}$ arylsulfonyl group (optionally having from 1 to 5 substituents $\alpha_{1c}$ mentioned below) or (viii) a $C_7$–$C_{16}$ aralkylsulfonyl group (optionally having from 1 to 5 substituents $\alpha_{1c}$ mentioned below on the aryl moiety), $A_c$ represents a nitrogen atom or a =CH— group, $B_c$ represents an oxygen atom or a sulfur atom, $W_{1c}$ represents a $C_1$–$C_8$ alkylene group, $W_{2c}$ represents a single bond or a $C_1$–$C_8$ alkylene group, $X_c$ represents (i) a hydrogen atom, (ii) a $C_1$–$C_6$ alkyl group, (iii) a $C_1$–$C_6$ halogenoalkyl group, (iv) a $C_1$–$C_6$ alkoxy group, (v) a halogen atom, (vi) a hydroxyl group, (vii) a cyano group, (viii) a nitro group, (ix) a $C_3$–$C_{10}$ cycloalkyl group, (x) a $C_6$–$C_{10}$ aryl group (optionally having from 1 to 5 substituents $\beta_c$ mentioned below), (xi) a $C_7$–$C_{16}$ aralkyl group (optionally having from 1 to 5 substituents $\beta_c$ mentioned below on the aryl moiety), (xii) a $C_1$–$C_7$ aliphatic acyl group, (xiii) a $C_4$–$C_{11}$ cycloalkylcarbonyl group, (xiv) a $C_7$–$C_{11}$ arylcarbonyl group (optionally having from 1 to 5 substituents $\beta_c$ mentioned below), (xv) a $C_8$–$C_{17}$ aralkylcarbonyl group (optionally having from 1 to 5 substituents $\beta_c$ mentioned below on the aryl moiety), (xvi) a monocyclic heteroaromatic carbonyl group (optionally having from 1 to 5 substituents $\beta_c$ mentioned below), (xvii) a carbamoyl group, (xviii) a $C_7$–$C_{11}$ arylaminocarbonyl group (optionally having from 1 to 5 substituents $\beta_c$ mentioned below on the aryl moiety) or (xix) an amino group (optionally having one or two substituents $\beta_c$ mentioned below), $Y_c$ represents an oxygen atom or a $S(O)_p$ group (wherein p is an integer of from 0 to 2), $Z_{1c}$ represents (i) a hydrogen atom, (ii) a $C_1$–$C_6$ alkyl group, (iii) a $C_1$–$C_6$ alkoxy group, (iv) a $C_1$–$C_6$ alkylthio group, (v) a halogen atom, (vi) a $C_6$–$C_{10}$ aryl group (optionally having from 1 to 5 substituents $\alpha_1$ mentioned below), (vii) a $C_7$–$C_{16}$ aralkyl group (optionally having from 1 to 5 substituents $\alpha_{1c}$ mentioned below on the aryl moiety), (viii) a $C_6$–$C_{10}$ aryloxy group (optionally having from 1 to 5 substituents $\alpha_{1c}$ mentioned below), (ix) a $C_7$–$C_{16}$ aralkyloxy group (optionally having from 1 to 5 substituents $\alpha_{1c}$ mentioned below on the aryl moiety), (x) a $C_3$–$C_{10}$ cycloalkyloxy group, (xi) a $C_3$–$C_{10}$ cycloalkylthio group, (xii) a saturated heterocyclic oxy group (optionally having from 1 to 5 substituents $\alpha_{1c}$ mentioned below), (xiii) a monocyclic heteroaromatic oxy group (optionally having from 1 to 5 substituents $\alpha_{1c}$ mentioned below), (xiv) a $C_6$–$C_{10}$ arylthio group (optionally having from 1 to 5 substituents $\alpha_{1c}$ mentioned below), (xv) a $C_7$–$C_{16}$ aralkylthio group (optionally having from 1 to 5 substituents $\alpha_{1c}$ mentioned below on the aryl moiety), (xvi) a saturated heterocyclic thio group (optionally having from 1 to 5 substituents $\alpha_{1c}$ mentioned below), (xvii) a monocyclic heteroaromatic thio group (optionally having from 1 to 5 substituents $\alpha_{1c}$ mentioned below), (xviii) an amino group (optionally having one or two substituents $\alpha_{1c}$ mentioned below) or (xix) a hydroxyl group, the substituent $\alpha_{1c}$ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group, (vii) a nitro group, (viii) a $C_3$–$C_{10}$ cycloalkyl group, (ix) a $C_6$–$C_{10}$ aryl group (optionally having from 1 to 5 substituents $\beta_c$ mentioned below), (x) a $C_7$–$C_{16}$ aralkyl group (optionally having from 1 to 5 substituents $\beta_c$ mentioned below on the aryl moiety), (xi) a $C_1$–$C_7$ aliphatic acyl group, (xii) a $C_4$–$C_{11}$ cycloalkylcarbonyl group, (xiii) a $C_7$–$C_{11}$ arylcarbonyl group (optionally having from 1 to 5 substituents $\beta_c$ mentioned below), (xiv) a $C_8$–$C_{17}$ aralkylcarbonyl group (optionally having from 1 to 5 substituents $\beta_c$ mentioned below on the aryl moiety), (xv) a monocyclic heteroaromatic carbonyl group (optionally having from 1 to 5 substituents $\beta_c$ mentioned below), (xvi) a carbamoyl group, (xvii) a $C_7$–$C_{11}$ arylaminocarbonyl group (optionally having from 1 to 5 substituents $\beta_c$ mentioned below on the aryl moiety), (xviii) an amino group (optionally having one or two substituents $\beta_c$ mentioned below) or (xix) a carboxyl group, the substituent $\beta_c$ represents (i) a $C_1$–$C_{10}$ alkyl group, (ii) a halogen atom, (iii) a $C_6$–$C_{10}$ aryl group (optionally having from 1 to 5 substituents $\gamma_c$ mentioned below), (iv) a $C_7$–$C_{16}$ aralkyl group (optionally having from 1 to 5 substituents $\gamma_c$ mentioned below on the aryl moiety), (v) a $C_1$–$C_7$ aliphatic acyl group, (vi) a $C_7$–$C_{11}$ arylcarbonyl group (optionally having from 1 to 5 substituents $\gamma_c$ mentioned below), (vii) a $C_8$–$C_{17}$ aralkylcarbonyl group (optionally having from 1 to 5 substituents $\gamma_c$ mentioned below on the aryl moiety), (viii) a $C_4$–$C_{11}$ cycloalkylcarbonyl group, (ix) a monocyclic heteroaromatic carbonyl group (optionally having from 1 to 5 substituents $\gamma_c$ mentioned below), (x) a carbamoyl group or (xi) a $C_7$–$C_{11}$ arylaminocarbonyl group (optionally having from 1 to 5 substituents $\gamma_c$ mentioned below on the aryl moiety) and the substituent $\gamma_c$ represents a $C_1$–$C_6$ alkyl group, a $C_1$–$C_6$ halogenoalkyl group, a halogen atom or a hydroxyl group].

An α-substituted carboxylic acid derivative having the general formula (Id) below:

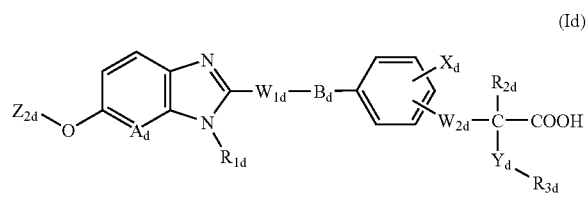

(Id)

a pharmacologically acceptable ester thereof, a pharmacologically acceptable amide thereof or a pharmacologically acceptable salt thereof

[wherein, $R_{1d}$, $R_{2d}$ and $R_{3d}$ are the same or different, and each represents (i) a hydrogen atom, (ii) a $C_1$–$C_6$ alkyl group, (iii) a $C_6$–$C_{10}$ aryl group (optionally having from 1 to 5 substituents $\alpha_{1d}$ mentioned below); (iv) a $C_7$–$C_{16}$ aralkyl group (optionally having from 1 to 5 substituents $\alpha_{1d}$ mentioned below on the aryl moiety), (v) a $C_1$–$C_6$ alkylsulfonyl group, (vi) a $C_1$–$C_6$ halogenoalkylsulfonyl group, (vii) a $C_6$–$C_{10}$ arylsulfonyl group (optionally having from 1 to 5 substituents $\alpha_{1d}$ mentioned below) or (viii) a $C_7$–$C_{16}$ aralkylsulfonyl group (optionally having from 1 to 5 substituents $\alpha_{1d}$ mentioned below on the aryl moiety), A$_d$ represents a nitrogen atom or a =CH— group, B$_d$ represents an oxygen atom or a sulfur atom, W$_{1d}$ represents a C$_1$–C$_8$ alkylene group, W$_{2d}$ represents a single bond or a C$_1$–C$_8$ alkylene group, X$_d$ represents (i) a hydrogen atom, (ii) a C$_1$–C$_6$ alkyl group, (iii) a C$_1$–C$_6$ halogenoalkyl group, (iv) a C$_1$–C$_6$ alkoxy group, (v) a halogen atom, (vi) a hydroxyl group, (vii) a cyano group, (viii) a nitro group, (ix) a C$_3$–C$_{10}$ cycloalkyl group, (x) a C$_6$–C$_{10}$ aryl group (optionally having from 1 to 5 substituents β$_d$ mentioned below), (xi) a C$_7$–C$_{16}$ aralkyl group (optionally having from 1 to 5 substituents β$_d$ mentioned below on the aryl moiety), (xii) a C$_1$–C$_7$ aliphatic acyl group, (xiii) a C$_4$–C$_{11}$ cycloalkylcarbonyl group, (xiv) a C$_7$–C$_{11}$ arylcarbonyl group (optionally having from 1 to 5 substituents β$_d$ mentioned below), (xv) a C$_8$–C$_{17}$ aralkylcarbonyl group (optionally having from 1 to 5 substituents β$_d$ mentioned below on the aryl moiety), (xvi) a monocyclic heteroaromatic carbonyl group (optionally having from 1 to 5 substituents β$_d$ mentioned below), (xvii) a carbamoyl group, (xviii) a C$_7$–C$_{11}$ arylaminocarbonyl group (optionally having from 1 to 5 substituents β$_d$ mentioned below on the aryl moiety) or (xix) an amino group (optionally having one or two substituents β$_d$ mentioned below)

Y$_d$ represents an oxygen atom or a S(O)$_p$ group (wherein p is an integer of from 0 to 2), Z$_{2d}$ represents a saturated heterocyclic group (optionally having from 1 to 5 substituents α$_{1d}$ mentioned below) or a C$_6$–C$_{10}$ aryl group (optionally having from 1 to 5 substituents α$_{2d}$ mentioned below), the substituent α$_{1d}$ represents (i) a C$_1$–C$_6$ alkyl group, (ii) a C$_1$–C$_6$ halogenoalkyl group, (iii) a C$_1$–C$_6$ alkoxy group, (iv) a halogen atom, (v) a hydroxyl group, (vi) a cyano group, (vii) a nitro group, (viii) a C$_3$–C$_{10}$ cycloalkyl group, (ix) a C$_6$–C$_{10}$ aryl group (optionally having from 1 to 5 substituents β$_d$ mentioned below), (x) a C$_7$–C$_{16}$ aralkyl group (optionally having from 1 to 5 substituents β$_d$ mentioned below on the aryl moiety), (xi) a C$_1$–C$_7$ aliphatic acyl group, (xii) a C$_4$–C$_{11}$ cycloalkylcarbonyl group, (xiii) a C$_7$–C$_{11}$ arylcarbonyl group (optionally having from 1 to 5 substituents β$_d$ mentioned below), (xiv) a C$_8$–C$_{17}$ aralkylcarbonyl group (optionally having from 1 to 5 substituents β$_d$ mentioned below on the aryl moiety), (xv) a monocyclic heteroaromatic carbonyl group (optionally having from 1 to 5 substituents β$_d$ mentioned below), (xvi) a carbamoyl group, (xvii) a C$_7$–C$_{11}$ arylaminocarbonyl group (optionally having from 1 to 5 substituents β$_d$ mentioned below on the aryl moiety), (xviii) an amino group (optionally having one or two substituents β$_d$ mentioned below) or (xix) a carboxyl group, the substituent α$_{2d}$ represents (i) a C$_3$–C$_{10}$ cycloalkyl group, (ii) a C$_6$–C$_{10}$ aryl group (optionally having from 1 to 5 substituents β$_d$ mentioned below), (iii) a C$_7$–C$_{16}$ aralkyl group (optionally having from 1 to 5 substituents β$_d$ mentioned below on the aryl moiety), (iv) a C$_1$–C$_7$ aliphatic acyl group, (v) a C$_4$–C$_{11}$ cycloalkylcarbonyl group, (vi) a C$_7$–C$_{11}$ arylcarbonyl group (optionally having from 1 to 5 substituents β$_d$ mentioned below), (vii) a C$_8$–C$_{17}$ aralkylcarbonyl group (optionally having from 1 to 5 substituents β$_d$ mentioned below on the aryl moiety), (viii) a monocyclic heteroaromatic carbonyl group (optionally having from 1 to 5 substituents β$_d$ mentioned below) or (ix) a C$_7$–C$_{11}$ arylaminocarbonyl group (optionally having from 1 to 5 substituents β$_d$ mentioned below on the aryl moiety), the substituent β$_d$ represents (i) a C$_1$–C$_{10}$ alkyl group, (ii) a halogen atom, (iii) a C$_6$–C$_{10}$ aryl group (optionally having from 1 to 5 substituents γ$_d$ mentioned below), (iv) a C$_7$–C$_{16}$ aralkyl group (optionally having from 1 to 5 substituents γ$_d$ mentioned below on the aryl moiety), (v) a C$_1$–C$_7$ aliphatic acyl group, (vi) a C$_7$–C$_{11}$ arylcarbonyl group (optionally having from 1 to 5 substituents γ$_d$ mentioned below), (vii) a C$_8$–C$_{17}$ aralkylcarbonyl group (optionally having from 1 to 5 substituents γ$_d$ mentioned below on the aryl moiety), (viii) a C$_4$–C$_{11}$ cycloalkylcarbonyl group, (ix) a monocyclic heteroaromatic carbonyl group (optionally having from 1 to 5 substituents γ$_d$ mentioned below), (x) a carbamoyl group or (xi) a C$_7$–C$_{11}$ arylaminocarbonyl group (optionally having from 1 to 5 substituents γ$_d$ mentioned below on the aryl moiety) and the substituent γ$_d$ represents a C$_1$–C$_6$ alkyl group, a C$_1$–C$_6$ halogenoalkyl group, a halogen atom or a hydroxyl group].

An α-substituted carboxylic acid derivative having the general formula (Ie) below:

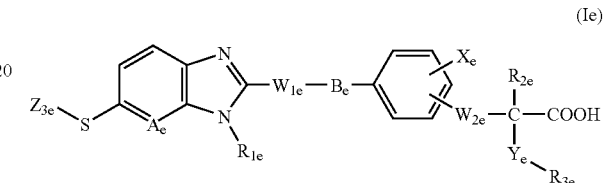

(Ie)

a pharmacologically acceptable ester thereof, a pharmacologically acceptable amide thereof or a pharmacologically acceptable salt thereof

[wherein,

R$_{1e}$, R$_{2e}$ and R$_{3e}$ are the same or different, and each represents (i) a hydrogen atom, (ii) a C$_1$–C$_6$ alkyl group, (iii) a C$_6$–C$_{10}$ aryl group (optionally having from 1 to 5 substituents α$_{1e}$ mentioned below), (iv) a C$_7$–C$_{16}$ aralkyl group (optionally having from 1 to 5 substituents α$_{1e}$ mentioned below on the aryl moiety), (v) a C$_1$–C$_6$ alkylsulfonyl group, (vi) a C$_1$–C$_6$ halogenoalkylsulfonyl group, (vii) a C$_6$–C$_{10}$ arylsulfonyl group (optionally having from 1 to 5 substituents α$_{1e}$ mentioned below) or (viii) a C$_7$–C$_{16}$ aralkylsulfonyl group (optionally having from 1 to 5 substituents α$_{1e}$ mentioned below on the aryl moiety), A$_e$ represents a nitrogen atom or a =CH— group, B$_e$ represents an oxygen atom or a sulfur atom, W$_{1e}$ represents a C$_1$–C$_8$ alkylene group, W$_{2e}$ represents a single bond or a C$_1$–C$_8$ alkylene group, X$_e$ represents (i) a hydrogen atom, (ii) a C$_1$–C$_6$ alkyl group, (iii) a C$_1$–C$_6$ halogenoalkyl group, (iv) a C$_1$–C$_6$ alkoxy group, (v) a halogen atom, (vi) a hydroxyl group, (vii) a cyano group, (viii) a nitro group, (ix) a C$_3$–C$_{10}$ cycloalkyl group, (x) a C$_6$–C$_{10}$ aryl group (optionally having from 1 to 5 substituents β$_e$ mentioned below), (xi) a C$_7$–C$_{16}$ aralkyl group (optionally having from 1 to 5 substituents β$_e$ mentioned below on the aryl moiety), (xii) a C$_1$–C$_7$ aliphatic acyl group, (xiii) a C$_4$–C$_{11}$ cycloalkylcarbonyl group, (xiv) a C$_7$–C$_{11}$ arylcarbonyl group (optionally having from 1 to 5 substituents β$_e$ mentioned below), (xv) a C$_8$–C$_{17}$ aralkylcarbonyl group (optionally having from 1 to 5 substituents β$_e$ mentioned below on the aryl moiety), (xvi) a monocyclic heteroaromatic carbonyl group (optionally having from 1 to 5 substituents β$_e$ mentioned below), (xvii) a carbamoyl group, (xviii) a C$_7$–C$_{11}$ arylaminocarbonyl group (optionally having from 1 to 5 substituents β$_e$ mentioned below on the aryl moiety) or (xix) an amino group (optionally having one or two substituents β$_e$ mentioned below), Y$_e$ represents an oxygen atom or a S(O)$_p$ group (wherein p is an integer of from 0 to 2), $Z_{3e}$ represents (i) a $C_1$–$C_6$ alkyl group, (ii) a $C_6$–$C_{10}$ aryl group (optionally having from 1 to 5 substituents $\alpha_{1e}$ mentioned below), (iii) a $C_7$–$C_{16}$ aralkyl group (optionally having from 1 to 5 substituents $\alpha_{1e}$ mentioned below on the aryl moiety), (iv) a $C_3$–$C_{10}$ cycloalkyl group or (v) a saturated heterocyclic group (optionally having from 1 to 5 substituents $\alpha_{1e}$ mentioned below), the substituent $\alpha_{1e}$ represents (i) a $C_1$–$C_6$ alkyl group, (ii) a $C_1$–$C_6$ halogenoalkyl group, (iii) a $C_1$–$C_6$ alkoxy group, (iv) a halogen atom, (v) a hydroxyl group, (vi) a cyano group, (vii) a nitro group, (viii) a $C_3$–$C_{10}$ cycloalkyl group, (ix) a $C_6$–$C_{10}$ aryl group (optionally having from 1 to 5 substituents $\beta_e$ mentioned below), (x) a $C_7$–$C_{16}$ aralkyl group (optionally having from 1 to 5 substituents $\beta_e$ mentioned below on the aryl moiety), (xi) a $C_1$–$C_7$ aliphatic acyl group, (xii) a $C_4$–$C_{11}$ cycloalkylcarbonyl group, (xiii) a $C_7$–$C_{11}$ arylcarbonyl group (optionally having from 1 to 5 substituents $\beta_e$ mentioned below), (xiv) a $C_8$–$C_{17}$ aralkylcarbonyl group (optionally having from 1 to 5 substituents $\beta_e$ mentioned below on the aryl moiety), (xv) a monocyclic heteroaromatic carbonyl group (optionally having from 1 to 5 substituents $\beta_e$ mentioned below), (xvi) a carbamoyl group, (xvii) a $C_7$–$C_{11}$ arylaminocarbonyl group (optionally having from 1 to 5 substituents $\beta_e$ mentioned below on the aryl moiety), (xviii) an amino group (optionally having one or two substituents $\beta_e$ mentioned below) or (xix) a carboxyl group, the substituent $\beta_e$ represents (i) a $C_1$–$C_{10}$ alkyl group, (ii) a halogen atom, (iii) a $C_6$–$C_{10}$ aryl group (optionally having from 1 to 5 substituents $\gamma_e$ mentioned below), (iv) a $C_7$–$C_{16}$ aralkyl group (optionally having from 1 to 5 substituents $\gamma_e$ mentioned below on the aryl moiety), (v) a $C_1$–$C_7$ aliphatic acyl group, (vi) a $C_7$–$C_{11}$ arylcarbonyl group (optionally having from 1 to 5 substituents $\gamma_e$ mentioned below), (vii) a $C_8$–$C_{17}$ aralkylcarbonyl group (optionally having from 1 to 5 substituents $\gamma_e$ mentioned below on the aryl moiety), (viii) a $C_4$–$C_{11}$ cycloalkylcarbonyl group, (ix) a monocyclic heteroaromatic carbonyl group (optionally having from 1 to 5 substituents $\gamma_e$ mentioned below), (x) a carbamoyl group or (xi) a $C_7$–$C_{11}$ arylaminocarbonyl group (optionally having from 1 to 5 substituents $\gamma_e$ mentioned below on the aryl moiety) and the substituent $\gamma_e$ represents a $C_1$–$C_6$ alkyl group, a $C_1$–$C_6$ halogenoalkyl group, a halogen atom or a hydroxyl group].

Pioglitazone is disclosed in U.S. Pat. No. 4,687,777, rosiglitazone is disclosed in U.S. Pat. No. 5,002,953, JTT-501 is disclosed in U.S. Pat. No. 5,728,720, MCC-555 is disclosed in U.S. Pat. No. 5,594,016, GI-262570 is disclosed in PCT Publication No. WO97/31907, YM-440 is disclosed in U.S. Pat. No. 5,643,931, KRP-297 is disclosed in U.S. Pat. No. 6,030,990, T-174 is disclosed in U.S. Pat. No. 4,897,393, NC-2100 is disclosed in U.S. Pat. No. 5,693,651, BMS-298585 is disclosed in PCT Publication No. WO01/21602, AZ-242 is disclosed in PCT Publication No. WO99/62872 and NN-622 is disclosed in PCT Publication No. WO99/19313.

5-[4-(6-methoxy-1-methyl-1H-benzimidazol-2-yl-methoxy)benzyl]thiazolidine-2,4 dione and pharmacologically acceptable salts thereof can be prepared according to those methods disclosed in Japanese Patent Application Publication No. Hei 9-295970, European Patent Publication No. 0745600, U.S. Pat. No. 5,886,014 and PCT Publication No. WO 00/71540A.

The compounds represented by the general formula (Ia) are disclosed in PCT Publication No. WO 97/37970 and can be prepared by the methods described in it.

The compounds represented by the general formula (Ib) are disclosed in PCT Publication No. WO 99/18066 and can be prepared by the methods described in it.

The compounds represented by the general formulae (Ic), (Id) and (Ie) are disclosed in PCT Publication No. WO 00/59889 and can be prepared by the methods described in it.

In the present invention, there is no particular limitation on the "diuretic", provided that the drug increases the amount of urine excretion. Examples include drugs such as acetazolamide, azosemide, amiloride, isosorbide, etacrynic acid, potassium canrenoate, chlortalidone, cyclopentiazide, spironolactone, torasemide, triamterene, trichlormethiazide, hydrochlorothiazide, hydrbflumethiazide, piretanide, bumetanide, furosemide, benzylhydrochlorothiazide, penflutizide, methyclothiazide, metolazone, mefruside, amiloride, preferably loop diuretics such as furosemide and etacrynic acid, and ENaC(Epitherial $Na^+$ Channels) blockers such as amiloride and triamterene, more preferably ENaC inhibitors.

A "loop diuretic" means a drug which inhibits the $Na^+$—$K^+$-$2Cl^-$ cotransport system in the thick ascending limb of Henle's loop. In the present invention, the loop diuretic is preferably furosemide.

A "ENaC inhibitor" means a drug which blocks Renal Epitherial $Na^+$ Channels. In the present invention, the ENaC inhibitor is preferably amiloride.

In the previous formula (Ia) of the present invention, when $R^{1a}$, $R^{3a}$, $W^a$ and $R^{4a}$ represent a straight- or branched-chain alkyl group having from 1 to 6 carbon atoms, the alkyl group can be, for example, a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group, and is preferably a straight- or branched-chain alkyl group having from 1 to 4 carbon atoms, more preferably a methyl, ethyl, propyl, isopropyl, butyl or isobutyl group. $R^{1a}$, $R^{3a}$ and $R^{4a}$ are still more preferably a straight- or branched-chain alkyl group having from 1 to 3 carbon atoms, most preferably an alkyl having one or two carbon atoms. $W^a$ is still more preferably a propyl or butyl group, most preferably a butyl group.

In the case where $R^{2a}$ represents a straight- or branched-chain alkylene group having from 2 to 6 carbon atoms, the alkylene group can be, for example, an ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group, and is preferably a straight- or branched-chain alkylene group having from 2 to 5 carbon atoms, more preferably a straight- or branched-chain alkylene group having from 2 to 4 carbon atoms, still more preferably an ethylene, methylethylene or trimethylene group, most preferably an ethylene group.

In the case where $Z^a$ represents a straight- or branched-chain alkylene group having from 1 to 6 carbon atoms, the alkylene group can be, for example, a methylene, ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group, and is preferably a straight- or branched-chain alkylene group having from 1 to 4 carbon atoms (for example, a methylene, ethylene, methylethylene, ethylethylene, trimethylene, 1-methyltrimethylene or 2-methyltrimethylene group), more preferably an alkylene group having one or two carbon atoms, most preferably a methylene group.

In the case where $R^{3a}$ and $W^a$ represent a straight- or branched-chain alkoxy group having from 1 to 4 carbon atoms, the alkoxy group can be, for example, a methoxy, ethoxy, propoxy, isopropoxy, butoxy, s-butoxy, t-butoxy or isobutoxy group. $R^{3a}$ is preferably an alkbxy group having one or two carbon atoms, most preferably a methoxy group, and $W^a$ is preferably an alkoxy group having from 1 to 3 carbon atoms, most preferably an ethoxy group.

In the case where $R^{3a}$ and $W^a$ represent a straight- or branched-chain alkylthio group having from 1 to 4 carbon atoms, the alkylthio group can be, for example, a methylthio, ethylthio, propylthio, isopropylthio, butylthio, s-butylthio, t-butylthio or isobutylthio group. $R^{3a}$ is preferably an alkylthio group having one or two carbon atoms, most preferably a methylthio group, and $W^a$ is preferably an alkylthio group having from 1 to 3 carbon atoms, most preferably a methylthio group.

In the case where $R^{3a}$ represents a halogen atom, the halogen atom can be a fluorine, chlorine, bromine or iodine atom, and is preferably a fluorine, chlorine or bromine atom, more preferably a fluorine or chlorine atom.

In the case where $W^a$ represents a straight- or branched-chain monoalkylamino group having from 1 to 4 carbon atoms, the monoalkylamino group can be, for example, a methylamino, ethylamino, propylamino, isopropylamino, butylamino, s-butylamino, t-butylamino or isobutylamino group, and is preferably a straight- or branched-chain monoalkylamino group having from 1 to 3 carbon atoms, most preferably a ethylamino group.

In the case where $R^{3a}$ and $W^a$ represent a straight- or branched-chain dialkylamino group in which the alkyl groups are the same or different from each other and each has from 1 to 4 carbon atoms, the dialkylamino group can be, for example, a dimethylamino, diethylamino, dipropylamino, diisopropylamilno, dibutylamino, N-methyl-N-ethylamino or N-ethyl-N-isopropylamino group, and is preferably a dimethylamino or diethylamino group, most preferably a diethylamino group.

In the case where $R^{3a}$ and $W^a$ represent an aryl group having from 6 to 10 carbon atoms which may have from 1 to 3 substituents $\alpha^a$ mentioned below, the unsubstituted aryl group can be, for example, a phenyl or naphthyl group, and is preferably a phenyl group. The substituted aryl group can be, for example, a 2-methylphenyl, 3-methylphenyl, 4-methylphenyl, 4-ethylphenyl, 4-propylphenyl, 4-isopropylphenyl, 4-trifluorobutylphenyl, 4-hydroxyphenyl, 4-acetoxyphenyl, 4-methoxyphenyl, 3,4-methylenedioxyphenyl, 4-benzyloxyphenyl, 4-methylthiophenyl, 4-methylsulfonylphenyl, 4-fluorophenyl, 4-chlorophenyl, 4-nitrophenyl, 4-dimethylaminophenyl, 4-benzylphenyl, 4-biphenylyl, 4-phenoxyphenyl, 4-phenylthiophenyl, 4-phenylsulfonylphenyl, 4-phenylsulfonylaminophenyl, 4-(2-pyridyl)phenyl, 4-(2-pyridyloxy)phenyl, 4-(2-pyridylthio)phenyl or 4-(2-pyridylsulfonylamino)phenyl group, and is preferably a 4-methylphenyl, 4-ethylphenyl, 4-isopropylphenyl, 4-methoxyphenyl, 4-methylthiophenyl or 4-chlorophenyl group.

In the case where $R^{3a}$ and $W^a$ represent an aralkyl group having from 7 to 12 carbon atoms which may have from 1 to 3 substituents $\alpha^a$ mentioned below, the unsubstituted aralkyl group is a group in which a straight- or branched-chain alkyl group having from 1 to 4 carbon atoms is substituted with the above-mentioned aryl group and can be, for example, a benzyl, phenethyl, 3-phenylpropyl, 4-phenylbutyl, 1-naphthylmethyl or 2-naphthylmethyl group. $R^{3a}$ is preferably a benzyl or phenethyl group, most preferably a benzyl group, and $W^a$ is preferably a benzyl, phenethyl, 3-phenylpropyl or 4-phenylbutyl group, most preferably a phenethyl or 3-phenylpropyl group. The substituted aralkyl group can be, for example, a 4-methylbenzyl, 4-trifluoromethylbenzyl, 4-methoxybenzyl, 3,4-methylenedioxybenzyl, 4-methylthiobenzyl, 4-methylsulfonylbenzyl, 4-fluorobenzyl, 4-chlorobenzyl, 2-(4-methylphenyl)ethyl, 2-(4-methoxyphenyl)ethyl, 3-(4-methylphenyl)propyl, 3-(4-methoxyphenyl)propyl, 4-(4-methylphenyl)butyl or 4-(4-methoxyphenyl)butyl group, and is preferably a 4-methylbenzyl or 2-(4-methylphenyl)ethyl group.

In the case where $W^a$ represents an N-alkyl-N-arylamino group having a straight- or branched-chain alkyl group having from 1 to 4 carbon atoms and an aryl group having from 6 to 10 carbon atoms which may have from 1 to 3 substituents $\alpha^a$ mentioned below on the aryl moiety, the alkyl group of the unsubstituted N-alkyl-N-arylamino group can be, for example, a methyl, ethyl, propyl, isopropyl, butyl, isobutyl, s-butyl or t-butyl group, and is preferably a methyl, ethyl, propyl, isopropyl, butyl or isobutyl group, most preferably a methyl or ethyl group. The aryl group can be, for example, a phenyl or naphthyl group, and is preferably a phenyl group. The unsubstituted N-alkyl-N-arylamino group can be, for example, an N-methyl-N-phenylamino, N-ethyl-N-phenylamino, N-propyl-N-phenylamino, N-isopropyl-N-phenylamino, N-butyl-N-phenylamino, N-isobutyl-N-phenylamino or N-methyl-N-naphthylamino group, and is preferably an N-methyl-N-phenylamino or N-ethyl-N-phenylamino group, most preferably an N-ethyl-N-phenylamino group. The substituted N-alkyl-N-arylamino group can be, for example, an N-methyl-N-(4-methylphenyl)amino, N-ethyl-N-(4-methylphenyl)amino, N-methyl-N-(4-methoxyphenyl)amino or N-ethyl-N-(4-methoxyphenyl)amino group, and is preferably an N-methyl-N-(4-methylphenyl)amino or N-ethyl-N-(4-methylphenyl)amino group.

In the case where $W^a$ represents an aryloxy group having from 6 to 10 carbon atoms which may have from 1 to 3 substituents $\alpha^a$ mentioned below on the aryl moiety, the unsubstituted aryloxy group can be, for example, a phenoxy or naphthyloxy group, and is preferably a phenoxy group. The substituted aryloxy group can be, for example, a 4-methylphenoxy, 4-ethylphenoxy, 4-propylphenoxy, 4-isopropylphenoxy, 4-methoxyphenoxy, 4-ethoxyphenoxy, 4-methylthiophenoxy, 4-ethylthiophenoxy, 4-biphenylyloxy or 4-methylsulfonylphenoxy group, and is preferably a 4-methylphenoxy, 4-ethylphenoxy or 4-isopropylphenoxy group.

In the case where $W^a$ represents an arylthio group having from 6 to 10 carbon atoms which may have from 1 to 3 substituents $\alpha^a$ mentioned below on the aryl moiety, the unsubstituted arylthio group can be, for example, a phenylthio or naphthylthio group, and is preferably a phenylthio group. The substituted arylthio group can be, for example, a 4-methylphenylthio, 4-ethylphenylthio, 4-propylphenylthio, 4-isopropylphenylthio, 4-methoxyphenylthio, 4-ethoxyphenylthio, 4-methylthiophenylthio, 4-ethylthiophenylthio, 4-biphenylylthio or 4-methylsulfonylphenylthio group, and is preferably a 4-methylphenylthio, 4-ethylphenylthio- or 4-isopropylphenylthio group.

In the case where $W^a$ represents an arylamino group having from 6 to 10 carbon atoms which may have from 1 to 3 substituents $\alpha^a$ mentioned below on the aryl moiety, the unsubstituted arylamino group can be, for example, a phenylamino or naphthylamino group, and is preferably a phenylamino group. The substituted arylamino group can be, for example, a 4-methylphenylamino, 4-ethylphenylamino, 4-propylphenylamino, 4-isopropylphenylamino, 4-methoxyphenylamino, 4-ethoxyphenylamino, 4-methylthiophenylamino, 4-ethylthiophenylamino, 4-biphenylylamino or 4-methylsulfonylphenylamino group, and is preferably a 4-methylphenylamino, 4-ethylphenylamino or 4-isopropylphenylamino group.

In the case where $W^a$ represents an aralkyloxy group having from 7 to 12 carbon atoms which may have from 1 to 3 substituents $\alpha^a$ mentioned below on the aryl moiety, the unsubstituted aralkyloxy group is a group in which a straight- or branched-chain alkyloxy group having from 1 to 4 carbon atoms is substituted with the above-mentioned aryl group and can be, for example, a benzyloxy, phenethyloxy, 3-phenylpropyloxy, 4-phenylbutyloxy, 1-naphthylmethyloxy or 2-naphthylmethyloxy group, and is preferably a benzyloxy or phenethyloxy group, most preferably a benzyloxy group. The substituted aralkyloxy group can be, for example, a 4-methylbenzyloxy, 4-methoxybenzyloxy, 2-(4-methylphenyl)ethoxy, 2-(4-methoxyphenyl)ethoxy, 3-(4-methylphenyl)propoxy, 3-(4-methoxyphenyl)propoxy, 4-(4-methylphenyl)butoxy or 4-(4-methoxyphenyl)butoxy group, and is preferably a 4-methylbenzyloxy or 2-(4-methylphenyl)ethoxy group.

In the case where $W^a$ represents an aralkylthio group having from 7 to 12 carbon atoms which may have from 1 to 3 substituents $\alpha^a$ mentioned below on the aryl moiety, the unsubstituted aralkylthio group is a group in which a straight- or branched-chain alkylthio group having from 1 to 4 carbon atoms is substituted with the above-mentioned aryl group and can be, for example, a benzylthio, phenethylthio, 3-phenylpropylthio, 4-phenylbutylthio, 1-naphthylmethylthio or 2-naphthylmethylthio group, and is preferably a benzylthio or phenethylthio group, most preferably a benzylthio group. The substituted aralkylthio group can be, for example, a 4-methylbenzylthio, 4-methoxybenzylthio, 2-(4-methylphenyl)ethylthio, 2-(4-methoxyphenyl)ethylthio, 3-(4-methylphenyl)propylthio, 3-(4-methoxyphenyl)propylthio, 4-(4-methylphenyl)butylthio or 4-(4-methoxyphenyl)butylthio group, and is preferably a 4-methylbenzylthio or 2-(4-methylphenyl)ethylthio group.

In the case where $W^a$ represents an aralkylamino group having from 7 to 12 carbon atoms which may have from 1 to 3 substituents $\alpha^a$ mentioned below on the aryl moiety, the unsubstituted aralkylamino group is a group in which a straight- or branched-chain alkylamino group having from 1 to 4 carbon atoms is substituted with the above-mentioned aryl group and can be, for example, a benzylamine, phenethylamino, 3-phenylpropylamino, 4-phenylbutylamino, 1-naphthylmethylamino or 2-naphthylmethylamino group, and is preferably a benzylamino or phenethylamino group, most preferably a benzylamino group. The substituted aralkylamino group can be, for example, a 4-methylbenzylamino, 4-methoxybenzylamino, 2-(4-methylphenyl)ethylamino, 2-(4-methoxyphenyl)ethylamino, 3-(4-methylphenyl)propylamino, 3-(4-methoxyphenyl)propylamino, 4-(4-methylphenyl)butylamino or 4-(4-methoxyphenyl)butylamino group, and is preferably a 4-methylbenzylamino or 2-(4-methylphenyl)ethylamino group.

In the case where $R^{4a}$ represents a straight- or branched-chain aliphatic acyl group or an aromatic acyl group having from 1 to 8 carbon atoms, the acyl group can be, for example, a formyl, acetyl, propionyl, butyryl, pentanoyl, hexanoyl, heptanoyl or octanoyl group, or a benzoyl or p-toluoyl group, and is preferably a straight- or branched-chain alkanoyl group having from 1 to 8 carbon atoms, more preferably a straight- or branched-chain alkanoyl group having from 2 to 5 carbon atoms, most preferably an acetyl group.

In the case where $X^a$ represents an aryl group having from 6 to 10 carbon atoms which may have from 1 to 3 substituents $\alpha^a$ mentioned below, the unsubstituted aryl group can be, for example, a phenyl or naphthyl group, and is preferably a phenyl group. In the case where $X^a$ represents an aryl group which is substituted with from 1 to 3 substituents $\alpha^a$ mentioned below, the number of substituents is preferably one or two, more preferably one.

In the case where $X^a$ represents a 5- to 10-membered monocyclic or bicyclic heteroaromatic group containing from 1 to 4 heteroatoms selected from the group consisting of oxygen, nitrogen and sulfur atoms which may have from 1 to 3 substituents $\alpha^a$ mentioned below, the unsubstituted heteroaromatic group comprises a monocyclic ring or a bicyclic ring system. In the case where the group is a bicyclic ring system, one of them at least is a heterocyclic ring. In the case of a bicyclic ring system, the group is a condensed ring, and either one ring is a heterocyclic ring and the other is a carbocyclic ring, or both of the rings are heterocyclic rings. The heterocyclic ring is a 5- or 6-membered ring and contains from 1 to 4 heteroatoms selected from the group consisting of nitrogen, oxygen and sulfur atoms. The carbocyclic ring is an aryl group having from 6 to 10 carbon atoms. The monocyclic ring system and the bicyclic ring system are referred to as monocyclic heteroaromatic group and condensed heteroaromatic ring group, respectively. In the case of a ring having four heteroatoms, it is preferred that the four heteroatoms are all nitrogen atoms with no heteroatom selected from the group consisting of oxygen and sulfur atoms. In the case of a ring having three heteroatoms, it is preferred that three, two or one of them are nitrogen atoms and one or two heteroatoms are selected from the group consisting of oxygen and sulfur atoms. In the case of a ring having two heteroatoms, it is preferred that two, one or none of them are nitrogen atoms and none, one or two of the heteroatoms are selected from the group consisting of oxygen and sulfur atoms. In the case where $X^a$ represents a heteroaromatic group which is substituted with from 1 to 3 substituents $\alpha^a$ mentioned below, the number of substituents is preferably one or two, more preferably one.

The unsubstituted monocyclic heteroaromatic group can be, for example, a pyrrolyl group such as 2-pyrrolyl and 3-pyrrolyl; a furyl group such as 2-furyl and 3-furyl; a thienyl group such as 2-thienyl and 3-thienyl; a pyridyl group such as 2-pyridyl, 3-pyridyl and 4-pyridyl; an imidazolyl group such as 2-imidazolyl and 4-imidazolyl; a pyrazolyl group such as 3-pyrazolyl and 4-pyrazolyl; an oxazolyl group such as 2-bxazolyl, 4-oxaz6-yl and 5-oxazolyl; an isoxazolyl group such as 3-isoxazolyl, 4-isoxazolyl and 5-isoxazolyl; a thiazolyl group such as 2-thiazolyl, 4-thiazolyl and 5-thiazolyl; an isothiazolyl group such as 3-isothiazolyl, 4-isothiazolyl and 5-isothiazolyl; a triazolyl group such as 1,2,3-triazol-4-yl and 1,2,4-triazol-3-yl; a thiadiazolyl group such as 1,3,4-thiadiazol-2-yl; an oxadiazolyl group such as 1,3,4-oxadiazol-2-yl; a tetrazolyl group such as 5-tetrazolyl; a pyridazinyl group such as 3-pyridazinyl and 4-pyridazinyl; a pyrimidinyl group such as 2-pyrimidinyl, 4-pyrimidinyl and 5-pyrimidinyl; a pyrazinyl group; an oxazinyl group such as 1,4-oxazin-2-yl and 1,4-oxazin-3-yl; or a thiazinyl group such as 1,4-thiazin-2-yl and 1,4-thiazin-3-yl.

The unsubstituted condensed aromatic heterocyclic ring group can be, for example, an indolyl group such as indol-2-yl, indol-3-yl, indol-4-yl, indol-5-yl, indol-6-yl and indol-7-yl; an indazolyl group such as indazol-2-yl, indazol-3-yl, indazol-4-yl, indazol-5-yl, indazol-6-yl and indazol-7-yl; a benzofuranyl group such as benzofuran-2-yl, benzofuran-3-yl, benzofuran-4-yl, benzofuran-5-yl, benzofuran-6-yl and benzofuran-7-yl; a benzothiophenyl group such as benzothiophen-2-yl, benzothiophen-3-yl, benzothiophen-4-yl, benzothiophen-5-yl, benzothiophen-6-yl and benzothiophen-7-yl; a benzimidazolyl group such as benzimidazol-2-yl, benzimidazol-4-yl, benzimidazol-5-yl, benzimidazol-6-yl and benzimidazol-7-yl; a benzoxazolyl group such as benzoxazol-2-yl, benzoxazol-4-yl, benzoxazol-5-yl, benzoxazol-6-yl and benzoxazol-7-yl; a benzothiazolyl group such as benzothiazol-2-yl, benzothiazol-4-yl, benzothiazol-5-yl, benzothiazol-6-yl and benzothiazol-7-yl; a quinolyl group such as 2-quinolyl, 3-quinolyl, 4-quinolyl, 5-quinolyl, 6-quinolyl, 7-quinolyl and 8-quinolyl; an isoquinolyl group such as 1-isoquinolyl, 3-isoquinolyl, 4-isoquinolyl and 8-isoquinolyl; a benzoxazinyl group such as 1,4-benzoxazin-2-yl and 1,4-benzoxazin-3-yl; a benzothiazinyl group such as 1,4-benzothiazin-2-yl and 1,4-benzothiazin-3-yl; a pyrrolo[2,3-b]pyridyl group such as pyrrolo[2,3-b]pyrid-2-yl and pyrrolo[2,3-b]pyrid-3-yl; a furo[2,3-b]pyridyl group such as furo[2,3-b]pyrid-2-yl and furo[2,3-b]pyrid-3-yl; a thieno[2,3-b]pyridyl group such as thieno[2,3-b]pyrid-2-yl and thieno[2,3-b]pyrid-3-yl; a naphthyridinyl group such as 1,8-naphthyridin-2-yl, 1,8-naphthyridin-3-yl, 1,5-naphthyridin-2-yl and 1,5-naphthyridin-3-yl; an imidazopyridyl group such as imidazo[4,5-b]pyrid-2-yl and imidazo[4,5-b]pyrid-5-yl; an oxazolopyridyl group such as oxazolo[4,5-b]pyrid-2-yl and oxazolo[5,4-b]pyrid-2-yl; or a thiazolopyridyl group such as thiazolo[4,5-b]pyrid-2-yl and thiazolo[4,5-c]pyrid-2-yl.

The monocyclic heteroaromatic group is preferably a 5- or 6-membered ring group having from 1 to 3 heteroatoms selected from the group consisting of nitrogen, oxygen and sulfur atoms, which can be a pyrrolyl, furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl or pyrazinyl group as exemplified above. The condensed heteroaromatic group is preferably a condensed-ring group of a benzene ring with the 5- or 6-membered heteroaromatic ring having from 1 to 3 heteroatoms selected from the group consisting of nitrogen, oxygen and sulfur atoms mentioned above, which can be an indolyl, benzofuranyl, benzothiophenyl, benzoimidazolyl, benzoxazolyl, benzothiazolyl, quinolyl or isoquinolyl group as exemplified above.

Preferred heteroaromatic groups are imidazolyl, oxazolyl, pyridyl, indolyl, quinolyl and isoquinolyl groups, more preferred are pyridyl, indolyl, quinolyl and isoquinolyl groups, still more preferred are pyridyl, quinolyl and isoquinolyl groups, and particularly preferred is pyridyl group.

In the case where the above-mentioned $X^a$ represents an aryl group having from 6 to 10 carbon atoms or a 5- to 10-membered monocyclic or bicyclic heteroaromatic group containing from 1 to 4 heteroatoms selected from the group consisting of oxygen, nitrogen and sulfur atoms, the aryl group and the heteroaromatic group may have from 1 to 3 substituents $\alpha^a$ mentioned above.

Here, in the case where the substituent $\alpha^a$ represents a straight- or branched-chain alkyl group-having from 1 to 6 carbon atoms, a straight- or branched-chain alkoxy group having from 1 to 4 carbon atoms, a straight- or branched-chain alkylthio group having from 1 to 4 carbon atoms, a halogen atom or a straight- or branched-chain dialkylamino group in which the alkyl groups are the same or different from each other and each has from 1 to 4 carbon atoms, these groups include the same groups as exemplified for the above-mentioned $R^{3a}$.

In the case where the substituent $\alpha^a$ represents a straight- or branched-chain halogenated alkyl group having from 1 to 4 carbon atoms, the halogenated alkyl group can be, for example, a chloromethyl, bromomethyl, fluoromethyl, iodomethyl, difluoromethyl, trifluoromethyl, pentafluoroethyl, 2,2,2-trifluoroethyl, 2,2,2-trichloroethyl or trichloromethyl group, and is preferably a methyl group having from 1 to 3 fluorine atoms, most preferably a trifluoromethyl group.

In the case where the substituent $\alpha^a$ represents a straight- or branched-chain aliphatic acyloxy group having from 1 to 4 carbon atoms, the acyloxy group can be, for example, a formyloxy, acetoxy, propionyloxy, butyryloxy, acroyloxy, methacryloyloxy or crotonoyloxy group, and is preferably an alkanoyloxy group, more preferably an alkanoyloxy group having one or two carbon atoms, most preferably an acetoxy group.

In the case where the substituent $\alpha^a$ represents a straight- or branched-chain alkylenedioxy group having from 1 to 4 carbon atoms, the alkylenedioxy group can be, for example, a methylenedioxy, ethylenedioxy, trimethylenedioxy, tetramethylenedioxy or propylenedioxy group, and is preferably a methylenedioxy or ethylenedioxy group, most preferably a methylenedioxy group.

In the case where the substituent $\alpha^a$ represents an aralkyloxy group having from 7 to 12 carbon atoms, the aralkyloxy group is an aralkyloxy group in which the aralkyl moiety is the same aralkyl as mentioned in $R^{3a}$, and can be, for example, a benzyloxy, phenethyloxy, 3-phenylpropoxy, 4-phenylbutoxy-, 1-naphthylmethoxy or 2-naphthylmethoxy group, and is preferably a benzyloxy, phenethyloxy, 1-naphthylmethoxy or 2-naphthylmethoxy group, more preferably a benzyloxy group.

In the case where the substituent $\alpha^a$ represents a straight- or branched-chain alkylsulfonyl group having from 1 to 4 carbon atoms, the alkylsulfonyl group can be, for example, a methylsulfonyl, ethylsulfonyl, propylsulfonyl, isopropylsulfonyl, butylsulfonyl, isobutylsulfonyl, sec-butylsulfonyl or t-butylsulfonyl group, and is preferably a methylsulfonyl, ethylsulfonyl or isopropylsulfonyl group, more preferably an alkylsulfonyl group having one or two carbon atoms.

In the case where the substituent $\alpha^a$ represents an aralkyl group having from 7 to 12 carbon atoms, the aralkyl group has the same meaning as defined in $R^{3a}$ and can be, for example, a benzyl, phenethyl, 3-phenylpropyl, 4-phenylbutyl, 1-naphthylmethyl or 2-naphthylmethyl group, and is preferably a benzyl, phenethyl, 1-naphthylmethyl or 2-naphthylmethyl group, more preferably a benzyl group.

In the case where the substituent $\alpha^a$ represents an aryl group having from 6 to 10 carbon atoms (the aryl group may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy of the substituent of the aryl group have the same meanings as defined above in the substituents of $R^{3a}$ and $X^a$.

The aryl group can be, for example, a phenyl, 1-naphthyl, 2-naphthyl, 4-methylphenyl, 4-trifluoromethylphenyl, 4-methoxyphenyl, 3-ethoxyphenyl, 4-fluorophenyl, 4-chlorophenyl, 3-bromophenyl or 3,4-methylenedioxyphenyl group, and is preferably phenyl, 4-methoxyphenyl or 3,4-methylenedioxyphenyl group.

In the case where the substituent $\alpha^a$ represents an aryloxy group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The aryloxy group can be, for example, a phenoxy, 1-naphthoxy, 2-naphthoxy, 4-methylphenoxy, 4-trifluoromethylphenoxy, 4-methoxyphenoxy, 3-ethoxyphenoxy, 4-chlorophenoxy, 3-bromophenoxy or 3,4-methylenedioxyphenoxy group, and is preferably a phenoxy group.

In the case where the substituent $\alpha^a$ represents an arylthio group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The arylthio group can be, for example, a phenylthio, 4-methylphenylthio, 4-trifluoromethylphenylthio, 4-methoxyphenylthio, 3-ethoxyphenylthio, 4-chlorophenylthio, 3-bromophenylthio, 3,4-methylenedioxyphenylthio, 1-naphthylthio or 2-naphthylthio group, and is preferably a phenylthio group.

In the case where the substituent $\alpha^a$ represents an arylsulfonyl group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The arylsulfonyl group can be, for example, a phenylsulfonyl, 4-methylphenylsulfonyl, 4-trifluoromethylphenylsulfonyl, 4-methoxyphenylsulfonyl, 3-ethoxyphenylsulfonyl, 4-chlorophenylsulfonyl, 3-bromophenylsulfonyl, 3,4-methylenedioxyphenylsulfonyl, 1-naphthylsulfonyl or 2-naphthylsulfonyl group, and is preferably a phenylsulfonyl group.

In the case where the substituent $\alpha^a$ represents an arylsulfonylamino group having from 6 to 10 carbon atoms (the aryl moiety may be substituted with a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms and the nitrogen atom of the amino moiety may be substituted with a straight- or branched-chain alkyl having from 1 to 6 carbon atoms), the alkyl, halogenated alkyl, alkoxy, halogen and alkylenedioxy have the same meanings as defined above.

The arylsulfonylamino group can be, for example, a phenylsulfonylamino, 4-methylphenylsulfonylamino, 4-trifluoromethylphenylsulfonylamino, 4-methoxyphenylsulfonylamino, 3-ethoxyphenylsulfonylamino, 4-chlorophenylsulfonylamino, 3-bromophenylsulfonylamino, 3,4-methylenedioxyphenylsulfonylamino, N-methylphenylsulfonylamino, 1-naphthylsulfonylamino, 2-naphthylsulfonylamino or N-methylnaphthylsulfonylamino group, and is preferably a phenylsulfonylamino or N-methylphenylsulfonylamino group.

In the case where the substituent $\alpha^a$ represents a 5- to 10-membered monocyclic or bicyclic heteroaromatic group containing from 1 to 4 heteroatoms selected from the group consisting of oxygen, nitrogen and sulfur atoms, the group can be, for example, a furyl, thienyl, oxazolyl, isoxazolyl, thiazolyl, imidazolyl, quinolyl, isoquinolyl, indolyl or pyridyl group, and is preferably a imidazolyl, quinolyl or pyridyl group, more preferably a pyridyl group.

In the case where the substituent $\alpha^a$ represents a 5- to 10-membered monocyclic or bicyclic heteroaromatic oxy group containing from 1 to 4 heteroatoms selected from the group consisting of oxygen, nitrogen and sulfur atoms, the heteroaromatic oxy group can be, for example, a furyloxy, thienyloxy, oxazolyloxy, isoxazolyloxy, thiazolyloxy, imidazolyloxy, quinolyloxy, isoquinolyloxy, indolyloxy or pyridyloxy group, and is preferably a isoxazolyloxy or pyridyloxy group, more preferably a pyridyloxy group.

In the case where the substituent $\alpha^a$ represents a 5- to 10-membered monocyclic or bicyclic heteroaromatic thio group containing from 1 to 4 heteroatoms selected from the group consisting of oxygen, nitrogen and sulfur atoms, the heteroaromatic thio group can be, for example, a furylthio, thienylthio, oxazolylthio, isoxazolylthio, thiazolylthio, imidazolylthio, quinolylthio, isoquinolylthio, indolylthio or pyridylthio group, and is preferably a isoxazolylthio or pyridylthio group, more preferably a pyridylthio group.

In the case where the substituent $\alpha^a$ represents a 5- to 10-membered monocyclic or bicyclic heteroaromatic sulfonyl group containing from 1 to 4 heteroatoms selected from the group consisting of oxygen, nitrogen and sulfur atoms, the heteroaromatic sulfonyl group can be, for example, a furylsulfonyl, thienylsulfonyl, oxazolylsulfonyl, isoxazolylsulfonyl, thiazolylsulfonyl, imidazolylsulfonyl, quinolylsulfonyl, isoquinolylsulfonyl, indolylsulfonyl or pyridylsulfonyl group, and is preferably a imidazolylsulfonyl, isoxazolylsulfonyl or pyridylsulfonyl group, more preferably a pyridylsulfonyl group.

In the case where the substituent $\alpha^a$ represents a 5- to 10-membered monocyclic or bicyclic heteroaromatic sulfonylamino group containing from 1 to 4 heteroatoms selected from the group consisting of oxygen, nitrogen and sulfur atoms (the nitrogen atom of the amino moiety may be substituted with a straight- or branched-chain alkyl having from 1 to 6 carbon atoms), the heteroaromatic sulfonylamino group can be, for example, a furylsulfonylamino, thienylsulfonylamino, oxazolylsulfonylamino, isoxazolylsulfonylamino, thiazolylsulfonylamino, imidazolylsulfonylamino, N-methylimidazolylsulfonylamino, quinolylsulfonylamino, isoquinolylsulfonylamino, indolylsulfonylamino, pyridylsulfonylamino or N-methylpyridylsulfonylamino group, and is preferably a imidazolylsulfonylamino, N-methylimidazolylsulfonylamino, pyridylsulfonylamino or N-methylpyridylsulfonylamino group, more preferably a pyridylsulfonylamino or N-methylpyridylsulfonylamino group.

Therefore, in the case where $X^a$ represents a substituted or unsubstituted aryl group having from 6 to 10 carbon atoms or a substituted or unsubstituted 5- to 10-membered monocyclic or bicyclic heteroaromatic group containing from 1 to 4 heteroatoms selected from the group consisting of oxygen, nitrogen and sulfur atoms, preferred examples are phenyl, 1-naphthyl, 2-naphthyl, m-tolyl, p-tolyl, 3-ethylphenyl, 4-ethylphenyl, 3-isopropylphenyl, 4-isopropylphenyl, 3-t- butylphenyl, 4-t-butylphenyl, 4-chloromethylphenyl, 4-bromomethylphenyl, 4-fluoromethylphenyl, 4-iodomethylphenyl, 3-difluoromethylphenyl, 4-trifluoromethylphenyl, 4-pentafluoroethylphenyl, 4-trichloromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, phenethyloxyphenyl, 1-naphthylmethoxyphenyl, 3-methylthiophenyl, 4-methylthiophenyl, 3-ethylthiophenyl, 4-ethylthiophenyl, 3-isopropylthiophenyl, 4-isopropylthiophenyl, 3-methylsulfonylphenyl, 4-methylsulfonylphenyl, 3-ethylsulfonylphenyl, 4-ethylsulfonylphenyl, 3-isopropylsulfonylphenyl, 4-isopropylsulfonylphenyl, 3-chlorophenyl, 4-chlorophenyl, 3-bromophenyl, 4-bromophenyl, 4-nitrophenyl, 4-aminophenyl, 3-methylaminophenyl, 4-ethylaminophenyl, 3-propylaminophenyl, 4-butylaminophenyl, 3-dimethylaminophenyl, 4-diethylaminophenyl, 3-dipropylaminophenyl, 4-dibutylaminophenyl, 3-benzylphenyl, 4-benzylphenyl, 3-phenethylphenyl, 4-(1-naphthylmethyl)phenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 3-(4-methoxyphenyl)phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl)phenyl, 4-(3-chlorophenyl)phenyl, 4-(4-chlorophenyl)phenyl, 4-(3-bromophenyl)phenyl, 4-(4-bromophenyl)phenyl, 3-(3,4-methylenedioxyphenyl)phenyl, 4-(3,4-methylenedioxyphenyl)phenyl, 3-benzylphenyl, 4-benzylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(imidazol-i-yl)phenyl, 4-(imidazol-1-yl)phenyl, 3-(1-methylimidazol-4-yl)phenyl, 4-(1-methylimidazol-4-yl)phenyl, 3-(2-furyl)phenyl, 4-(2-furyl)phenyl, 3-(2-thienyl)phenyl, 4-(2-thienyl)phenyl, 3-(3-thienyl)phenyl, 4-(3-thienyl)phenyl, 3-(2-pyridyl)phenyl, 4-(2-pyridyl)phenyl, 3- (3-pyridyl)phenyl, 4-(3-pyridyl)phenyl, 3-(4-pyridyl)phenyl, 4-(4-pyridyl)phenyl, 4-(imidazol-1-ylthio)phenyl, 4-(2-furylthio)phenyl, 4-(2-thienylthio)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino)phenyl, 3-(N-methyl-3-pyridylsulfonylamino)phenyl, 4-(3-pyridylsulfonylamino)phenyl, 4-(N-methyl-3-pyridylsulfonylamino)phenyl, 3-(oxazol-2-yl)phenyl, 4-(oxazol-2-yl)phenyl, 3-(oxazol-4-yl)phenyl, 4-(oxazol-4-yl)phenyl, 3-(oxazol-5-yl)phenyl, 4-(oxazol-5-yl)phenyl, 3-(thiazol-2-yl)phenyl, 4-(thiazol-2-yl)phenyl, 3-(thiazol-4-yl)phenyl, 4-(thiazol-4-yl)phenyl, 3-(thiazol-5-yl)phenyl, 4-(thiazol-5-yl)phenyl, 1-methyl-2-pyrrolyl, 1-phenyl-2-pyrrolyl, 1-benzyl-2-pyrrolyl, 5-methyl-2-furyl, 5-phenyl-2-furyl, 5-methyl-2-thienyl, 5-phenyl-2-thienyl, 5-methyl-3-thienyl, 5-phenyl-3-thienyl, 1-methyl-3-pyrazolyl, 1-phenyl-3-pyrazolyl, 1-methyl-2-imidazolyl, 1-phenyl-2-imidazolyl, 1-methyl-4-imidazolyl, 1-phenyl-4-imidazolyl, 1-methyl-2-phenyl-4-imidazolyl, 1,5-dimethyl-2-phenyl-4-imidazolyl, 1,4-dimethyl-2-phenyl-5-imidazolyl, 4-oxazolyl, 5-oxazolyl, 2-methyl-4-oxazolyl, 2-phenyl-4-oxazolyl, 2-methyl-5-oxazolyl, 2-phenyl-5-oxazolyl, 4-methyl-2-phenyl-5-oxazolyl, 5-methyl-2-phenyl-4-oxazolyl, 4-thiazolyl, 5-thiazolyl, 2-methyl-4-thiazolyl, 2-phenyl-4-thiazolyl, 2-methyl-5-thiazolyl, 2-phenyl-5-thiazolyl, 4-methyl-2-phenyl-5-thiazolyl, 5-methyl-2-phenyl-4-thiazolyl, 1-methyl-3-pyrazolyl, 1-phenyl-3-pyrazolyl, 3-methyl-5-isoxazolyl, 3-phenyl-5-isoxazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-isopropylthio-5-pyridyl, 2-methylsulfonyl-5-pyridyl, 2-ethylsulfonyl-5-pyridyl, 2-isopropylsulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-methyl-4-pyrimidinyl, 2-phenyl-4-pyrimidinyl, 2-methoxy-4-pyrimidinyl, 2-ethoxy-4-pyrimidinyl, 2-isopropoxy-4-pyrimidinyl, 2-methylthio-4-pyrimidinyl, 2-ethylthio-4-pyrimidinyl, 2-isopropylthio-4-pyrimidinyl, 2-phenylthio-4-pyrimidinyl, 2-methylsulfonyl-4-pyrimidinyl, 2-ethylsulfonyl-4-pyrimidinyl, 2-isopropylsulfonyl-4-pyrimidinyl, 2-phenylsulfonyl-4-pyrimidinyl, 2-methyl-5-pyrimidinyl, 2-phenyl-5-pyrimidinyl, 2-methoxy-5-pyrimidinyl, 2-ethoxy-5-pyrimidinyl, 2-isopropoxy-5-pyrimidinyl, 2-methylthio-5-pyrimidinyl, 2-ethylthio-5-pyrimidinyl, 2-isopropylthio-5-pyrimidinyl, 2-phenylthio-5-pyrimidinyl, 2-methylsulfonyl-5-pyrimidinyl, 2-ethylsulfonyl-5-pyrimidinyl, 2-isopropylsulfonyl-5-pyrimidinyl, 2-phenylsulfonyl-5-pyrimidinyl, 2-indolyl, 3-indolyl, 1-methyl-2-indolyl, 1-methyl-3-indolyl,-2-benzimidazolyl, 1-methyl-2-benzimidazolyl, 2-benzoxazolyl, 2-benzothiazolyl, 2-quinolyl, 3-quinolyl, 4-quinolyl, 1-isoquinolyl, 3-isoquinolyl, 4-isoquinolyl and 8-isoquinolyl groups, more preferably phenyl, 1-naphthyl, 2-naphthyl, m-tolyl, p-tolyl, 3-ethylphenyl, 4-ethylphenyl, 3-isopropylphenyl, 4-isopropylphenyl, 4-trifluoromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, 3-methylthiophenyl, 4-methylthiophenyl, 3-ethylthiophenyl, 4-ethylthiophenyl, 3-methylsulfonylphenyl, 4-methylsulfonylphenyl, 3-ethylsulfonylphenyl, 4-ethylsulfonylphenyl, 3-chlorophenyl, 4-chlorophenyl, 3-benzylphenyl, 4-benzylphenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 3-(4-methoxyphenyl)phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl)phenyl, 4-(3-chlorophenyl)phenyl, 4-(4-chlorophenyl)phenyl, 3-(3,4-methylenedioxyphenyl)phenyl, 4-(3,4-methylenedioxyphenyl)phenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino) phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino)phenyl, 3-(N-methyl-3-pyridylsulfonylamino)phenyl, 4-(3-pyridylsulfonylamino)phenyl, 4-(N-methyl-3-pyridylsulfonylamino)phenyl, 2-pyridyl, 3-pyridyl, 4-pyridyl, 3-methyl-5-pyridyl 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-isopropylthio-5-pyridyl, 2-methylsulfonyl-5-pyridyl, 2-ethylsulfonyl-5-pyridyl, 2-isopropylsulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-quinolyl, 3-quinolyl, 4-quinolyl, 1-isoquinolyl, 3-isoquinolyl, 4-isoquinolyl and 8-isoquinolyl groups, most preferably phenyl, m-tolyl, p-tolyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-chlorophenyl, 4-chlorophenyl, 3-benzylphenyl, 4-benzylphenyl, 3-biphenylyl, 4-biphenylyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 3-(3-pyridyl) phenyl, 4-(3-pyridyl)phenyl, 3-(4-pyridyl)phenyl, 4-(4-pyridyl)phenyl, 4-(2-pyridyloxy)phenyl, 4-(4-pyridyloxy) phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 2-pyridyl, 3-pyridyl, 4-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-methylsulfonyl-5-pyridyl, 2-ethylsulfonyl-5-pyridyl, 2-benzyl-5-pyridyl, 2-phenyl-5-pyridyl, 3-phenyl-5-pyridyl, 2-phenyl-6-pyridyl, 3-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl and 2-(N-methylphenylsulfonylamino)-5-pyridyl groups.

In the case where $Y^a$ represents a group of formula >N—$R^{4a}$ (wherein $R^{4a}$ represents a hydrogen atom, a straight- or branched-chain alkyl group having from 1 to 6 carbon atoms (which has the same meaning as defined above in $R^{3a}$) or a straight- or branched-chain aliphatic acyl group having from 1 to 8 carbon atoms (which includes an alkanoyl group having from 1 to 8 carbon atoms and an alkenoyl group having from 3 to 8 carbon atoms) or an aromatic acyl group), the group of formula >N—$R^{4a}$ can be, for example, an imino, methylimino, ethylimino, propylimino, isopropylimino, butylimino, isobutylimino, s-butylimino, t-butylimino, pentylimino, 1-methylbutylimino, 2-methylbutylimino, 3-methylbutylimino, 1,1-dimethylpropylimino, 1,2-dimethylpropylimino, 2,2-dimethylpropylimino, 1-ethylpropylimino, hexylimino, 1-methylpentylimino, 2-methylpentylimino, 3-methylpentylimino, 4-methylpentylimino, 1,1-dimethylbutylimino, 1,2-dimethylbutylimino, 1,3-dimethylbutylimino, 2,2-dimethylbutylimino, 2,3-dimethylbutylimino, 3,3-dimethylbutylimino, 1-ethylbutylimino, 1,1,2-trimethylpropylimino, 1,2,2-trimethylpropylimino, acetylimino, propionylimino, butyrylimino, pentanoylimino, hexanoylimino, heptanoylimino, octanoylimino, benzoylimino or p-toluoylimino group, and is preferably an imino, straight- or branched-chain alkylimino having from 1 to 4 carbon atoms, or acetylimino group, more preferably an imino, methylimino, ethylimino or acetylimino group.

The phenylalkylcarboxylic acid derivatives of formula (Ia) of the present invention can be converted into acid addition salts according to conventional methods when they have a basic group. Such salts can be, for example, salts of hydrohalogenic acids such as hydrofluoric acid, hydrochloric acid, hydrobromic acid and hydroiodic acid; inorganic acid salts such as nitrate, perchlorate, sulfate and phosphate; salts of lower alkanesulfonic acids such as methanesulfonic acid, trifluoromethanesulfonic acid and ethanesulfonic acid; salts of arylsulfonic acids such as benzenesulfonic acid and p-toluenesulfonic acid; salts of amino acids such as glutamic acid and aspartic acid; and salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid; and are preferably salts of hydrohalogenic acids.

Furthermore, the compounds of formula (Ia) can be converted into metal salts according to conventional methods when they have a carboxyl group. Such salts can be, for example, salts of alkali metals such as lithium, sodium and potassium; salts of alkaline earth metal such as calcium, barium and magnesium; aluminum salts; and the like; and are preferably the salts of alkali metals.

The phenylalkylcarboxylic acid derivatives of formula (Ia) can be converted into pharmacologically acceptable esters according to conventional methods. The pharmacologically acceptable esters of the phenylalkylcarboxylic acid derivatives of formula (I) are not particularly limited as long as they can be used medically and their pharmacological acceptability is comparable with that of the phenylalkylcarboxylic acids of formula (I).

The ester of the phenylalkylcarboxylic acid of formula (Ia) of the present invention can be, for example, a straight- or branched-chain alkyl group having from 1 to 6 carbon atoms, an aralkyl group having from 7 to 19 carbon atoms, a straight- or branched-chain alkyl group having from 1 to 5 carbon atoms which is substituted with a straight- or branched-chain alkanoyloxy group having from 1 to 6 carbon atoms, a straight- or branched-chain alkyl group having from 1 to 5 carbon atoms which is substituted with a straight- or branched-chain alkyloxycarbonyloxy group having from 1 to 6 carbon atoms, a straight- or branched-chain alkyl group having from 1 to 5 carbon atoms which is substituted with a cycloalkylcarbonyloxy group having from 5 to 7 carbon atoms, a straight- or branched-chain alkyl group having from 1 to 5 carbon atoms which is substituted with a cycloalkyloxycarbonyloxy group having from 5 to 7 carbon atoms, a straight- or branched-chain alkyl group having from 1 to 5 carbon atoms which is substituted with a arylcarbonyloxy group having from 6 to 10 carbon atoms, a straight- or branched-chain alkyl group having from 1 to 5 carbon atoms which is substituted with a aryloxycarbonyloxy group having from 6 to 10 carbon atoms, or a 2-oxo-1,3-dioxolen-4-yl group having a straight- or branched-chain alkyl group having from 1 to 6 carbon atoms as a substituent at the 5-position.

Here, the straight- or branched-chain alkyl group having from 1 to 4 carbon atoms and the straight- or branched-chain alkyl group having from 1 to 6 carbon atoms can be, for example, a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group, and is preferably a straight- or branched-chain alkyl group having from 1 to 4 carbon atoms, more preferably a methyl, ethyl, propyl, isopropyl, butyl or isobutyl group, most preferably a methyl or ethyl group.

The aralkyl group having from 7 to 19 carbon atoms can be, for example, a benzyl, phenethyl, 3-phenylpropyl, 4-phenylbutyl, 1-naphthylmethyl, 2-naphthylmethyl or diphenylmethyl group, and is preferably a benzyl group.

The cycloalkyl group having from 5 to 7 carbon atoms can be, for example, a cyclopentyl, cyclohexyl or cycloheptyl group, and is preferably a cyclohexyl group.

The aryl group having from 6 to 10 carbon atoms can be, for example, a phenyl or-naphthyl group, and is preferably a phenyl group.

Examples of preferred ester residual groups include, for example, methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl and 5-methyl-2-oxo-1,3-dioxolen-4-yl groups.

Incidentally, the compound of formula (Ia) has various isomers. For example, there are optical isomers derived from the asymmetry of the carbon at the $\alpha^a$-position of the carboxylic group. In the formula (Ia), stereoisomers based on the asymmetric carbon atom and equal and unequal weight mixtures of these stereoisomers all are represented by the single formula. Therefore, the present invention includes all these isomers and mixtures of these isomers.

Furthermore, in the phenylalkylcarboxylic acid derivatives of formula (Ia), cis-isomers and trans-isomers based on geometrical isomerism can exist in the oxime moiety. In the formula (Ia), both isomers based on the geometrical isomerism and equal and unequal weight mixtures of these isomers are all represented by the single formula. Therefore, the present invention includes all these isomers and mixtures of these isomers.

Furthermore, in the case where the phenylalkylcarboxylic acid of formula (Ia) or salt thereof forms solvates (for example, hydrates), the present invention includes all these compounds.

Furthermore, the present invention includes all compounds which are metabolized in vivo to be converted to the phenylalkylcarboxylic acid derivatives of formula (Ia) or salts thereof, for example, amide derivatives, i.e. prodrugs.

In the previous formula (Ib) of the present invention, when $R^{1b}$, $R^{3b}$, $R^{4b}$, $R^{5b}$ and $W^b$ represent a straight- or branched chain alkyl group having from 1 to 6 carbon atoms, the alkyl group can be, for example, a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group; preferably, each of $R^{1b}$, $R^{3b}$, $R^{4b}$ and $R^{5b}$ is a straight- or branched-chain alkyl group having from 1 to 4 carbon atoms, and $W^b$ is a straight- or branched-chain alkyl group having from 2 to 6 carbon atoms; more preferably, each of $R^{1b}$, $R^{3b}$, $R^{4b}$ and $R^{5b}$ is a methyl, ethyl, propyl, isopropyl, butyl or isobutyl group, and $W^b$ is an ethyl, propyl, isopropyl, butyl, isobutyl or pentyl group. Most preferably, each of $R^{1b}$ and $R^{5b}$ is an alkyl group having one or two carbon atoms (particularly a methyl group), $R^{3b}$ is a methyl, ethyl or isopropyl group (particularly a methyl or isopropyl group), $R^{4b}$ is an alkyl group having one or two carbon atoms (particularly a methyl group), and $W^b$ is a propyl, butyl or pentyl group (particularly a propyl or butyl group).

In the case where $R^{1b}$ represents an aralkyl group having from 7 to 12 carbon atoms, the aralkyl group is a group in which a straight- or branched-chain alkyl group having from 1 to 4 carbon atoms is substituted with an aryl group and can be, for example, a benzyl, phenethyl, 3-phenylpropyl, 4-phenylbutyl, 5-phenylpentyl, 6-phenylhexyl, 1-naphthylmethyl or 2-naphthylmethyl group, and is preferably a benzyl, phenethyl or 3-phenylpropyl group, more preferably a 3-phenylpropyl group.

In the case where $R^{2b}$ and $Z^b$ represent a straight- or branched-chain alkylene group having from 1 to 6 carbon atoms, the alkylene group can be, for example, a methylene, ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group. $R^{2b}$ is preferably a straight- or branched-chain alkylene group having from 2 to 5 carbon atoms, more preferably $R^{2b}$ is a straight- or branched-chain alkylene group having from 2 to 4 carbon atoms, still more preferably $R^{2b}$ is an ethylene, trimethylene or methylethylene group, most preferably $R^{2b}$ is an ethylene group. $Z^b$ is preferably a straight- or branched-chain alkylene group having from 1 to 4 carbon atoms (for example, a methylene, ethylene, methylethylene, ethylethylene, trimethylene, 1-methyltrimethylene or 2-methyltrimethylene group), more preferably an alkylene group having one or two carbon atoms, most preferably a methylene group.

In the case where $R^{3b}$ and $W^b$ represent a straight- or branched-chain alkoxy group having from 1 to 4 carbon atoms, the alkoxy group can be, for example, a methoxy, ethoxy, propoxy, isopropoxy,-butoxy, s-butoxy, t-butoxy or isobutoxy group. $R^{3b}$ is preferably an alkoxy group having from 1 to 3 carbon atoms (particularly a methoxy, ethoxy or isopropoxy group); more preferably an alkoxy group having one or two carbon atoms (particularly a methoxy group). $W^b$ is preferably an alkoxy group having from 1 to 3 carbon atoms, more preferably an ethoxy group.

In the case where $R^{3b}$ and $W^b$ represent a straight- or branched-chain alkylthio group having from 1 to 4 carbon atoms, the alkylthio group can be, for example, a methylthio, ethylthio, propylthio, isopropylthio, butylthio, s-butylthio, t-butylthio or isobutylthio group. $R^{3b}$ is preferably an alkylthio group having one or two carbon atoms; more preferably a methylthio group. $W^b$ is preferably an alkylthio group having from 1 to 3 carbon atoms (for example, a methylthio, ethylthio, propylthio or isopropylthio group); more preferably a methylthio group.

In the case where $R^{3b}$ represents a halogen atom, the halogen atom can be a fluorine, chlorine, bromine or iodine atom, and is preferably a fluorine, chlorine or bromine atom, more preferably a fluorine or chlorine atom.

In the case where $R^{3b}$ and $W^b$ represent a straight- or branched-chain dialkylamino group in which each alkyl group may be the same or different and each has from 1 to 4 carbon atoms, the dialkylamino group can be, for example, a dimethylamino, diethylamino, dipropylamino, diisopropylamino, dibutylamino, N-methyl-N-ethylamino or N-ethyl-N-isopropylamino group, and is preferably a dimethylamino or diethylamino group, more preferably a diethylamino group.

In the case where $R^{3b}$ and $W^b$ represent an aryl group having from 6 to 10 carbon atoms which may have from 1 to 5 substituents, mentioned below, the unsubstituted aryl group can be, for example, a phenyl or naphthyl group, and is preferably a phenyl group. The substituted aryl group can be, for example, a methylphenyl, ethylphenyl, propylphenyl, isopropylphenyl, trifluoromethylphenyl, hydroxyphenyl, acetylphenyl, methoxyphenyl, methylenedioxyphenyl, benzyloxyphenyl, methylthiophenyl, methanesulfonylphenyl, fluorophenyl, difluorophenyl, chlorophenyl, dichlorophenyl, nitrophenyl, (dimethylamino)phenyl, benzylphenyl, biphenylyl, phenoxyphenyl, phenylthiophenyl, phenylsulfonylphenyl, (phenylsulfonylamino)phenyl, pyridylphenyl, pyridyloxyphenyl, pyridylthiophenyl, (pyridylsulfonylamino)phenyl, methylnaphthyl, trifluoronaphthyl, hydroxynaphthyl, methoxynaphthyl, fluoronaphthyl, chloronaphthyl or pyridylnaphthyl group, and is preferably an aryl group having from 6 to 10 carbon atoms which may have from 1 to 3 substituents $\alpha^b$ mentioned below, more preferably a methylphenyl, ethylphenyl, isopropylphenyl, methoxyphenyl, methylthiophenyl or chlorophenyl group.

In the case where $R^{3b}$ and $W^b$ represent an aralkyl group having from 7 to 12 carbon atoms which may have from 1 to 5 substituents $\alpha^b$ mentioned below on the aryl moiety, the aralkyl group is a group in which a straight- or branched-chain alkyl group having from 1 to 4 carbon atoms is substituted with the above aryl group and can be, for example, a benzyl, phenethyl, 3-phenylpropyl, 4-phenylbutyl, 5-phenylpentyl, 6-phenylhexyl, naphthylmethyl, methylbenzyl, trifluoromethylbenzyl, methoxybenzyl, methylenedioxybenzyl, methylthiobenzyl, methanesulfonylbenzyl, fluorobenzyl, chlorobenzyl, 2-(methylphenyl)ethyl, 2-(methoxyphenyl)ethyl, 3-(methylphenyl)propyl, 3-(methoxyphenyl)propyl, 4-(methylphenyl)butyl or 4-(methoxyphenyl)butyl group. $R^{3b}$ is preferably a benzyl or phenethyl group, more preferably a benzyl group. $W^b$ is preferably an aralkyl group having from 7 to 12 carbon atoms which may have from 1 to 3 substituents $\alpha^a$ mentioned below on the aryl moiety, more preferably an aralkyl group having from 7 to 10 carbon atoms (for example, a benzyl, phenethyl, 3-phenylpropyl or 4-phenylbutyl group), most preferably a 3-phenylpropyl or 4-phenylbutyl group (particularly a 3-phenylpropyl group).

In the case where $R^{3b}$ represents a straight- or branched-chain aliphatic acyl group having from 1 to 5 carbon atoms, the aliphatic acyl group can be, for example, a formyl, acetyl, propionyl, butyryl, isobutyryl, pentanoyl or pivaloyl group, and is preferably a formyl, acetyl or pivaloyl group, most preferably a formyl or acetyl group.

In the case where $W^b$ represents an aryloxy group having from 6 to 10 carbon atoms which may have from 1 to 5 substituents a mentioned below on the aryl moiety, the unsubstituted aryloxy group can be, for example, a phenoxy or naphthyloxy group, and is preferably a phenoxy group. The substituted aryloxy group can be, for example, a methylphenoxy, ethylphenoxy, propylphenoxy, isopropylphenoxy, t-butylphenoxy, trifluoromethylphenoxy, methoxyphenoxy, ethoxyphenoxy, isopropoxyphenoxy, trifluoromethoxyphenoxy, methylthiophenoxy, ethylthiophenoxy, cyanophenoxy, formylphenoxy, fluorophenoxy, difluorophenoxy, trifluorophenoxy, pentafluorophenoxy, chlorophenoxy, dichlorophenoxy, trichlorophenoxy, pyridylphenoxy, biphenylyloxy, methanesulfonylphenoxy, methylnaphthyloxy, ethylnaphthyloxy, propylnaphthyloxy, isopropylnaphthyloxy, t-butylnaphthyloxy, trifluoromethylnaphthyloxy, methoxynaphthyloxy, ethoxynaphthyloxy, isopropoxynaphthyloxy, trifluoromethoxynaphthyloxy, methylthionaphthyloxy, ethylthionaphthyloxy, cyanonaphthyloxy, formylnaphthyloxy, fluoronaphthyloxy, difluoronaphthyloxy, trifluoronaphthyloxy, pentafluoronaphthyloxy, chloronaphthyloxy, dichloronaphthyloxy, trichloronaphthyloxy, pyridylnaphthyloxy, biphenylyloxy or methanesulfonylnaphthyloxy group, and is preferably an aryloxy group having from 6 to 10 carbon atoms which may have from 1 to 3 substituents $\alpha^a$ mentioned below on the aryl moiety, more preferably a phenoxy group which may have from 1 to 3 substituents $\alpha^b$ mentioned below on the phenyl moiety (particularly a phenoxy group which may have one substituent $\alpha^b$ mentioned below on the phenyl moiety), most preferably a methylphenoxy, ethylphenoxy, isopropylphenoxy, t-butylphenoxy, trifluoromethylphenoxy, methoxyphenoxy, ethoxyphenoxy, trifluoromethoxyphenoxy, cyanophenoxy, formylphenoxy, fluorophenoxy, difluorophenoxy, trifluorophenoxy, pentafluorophenoxy, chlorophenoxy, dichlorophenoxy, trichlorophenoxy, pyridylphenoxy or methanesulfonylphenoxy group; still most preferably a methylphenoxy, ethylphenoxy, isopropylphenoxy, t-butylphenoxy, trifluoromethylphenoxy, methoxyphenoxy, ethoxyphenoxy, trifluoromethoxyphenoxy, cyanophenoxy, formylphenoxy, fluorophenoxy, difluorophenoxy, trifluorophenoxy, pentafluorophenoxy, chlorophenoxy, dichlorophenoxy, trichlorophenoxy or methanesulfonylphenoxy group, particularly most preferably a 4-methylphenoxy, 4-isopropylphenoxy, 4-t-butylphenoxy, 4-methoxyphenoxy, 4-trifluoromethoxyphenoxy, 3-fluorophenoxy, 4-fluorophenoxy or 4-chlorophenoxy group.

In the case where $W^b$ represents an arylthio group having from 6 to 10 carbon atoms which may have from 1 to 5 substituents $\alpha^b$ mentioned below on the aryl moiety, the unsubstituted arylthio group can be, for example, a phenylthio or naphthylthio group, and is preferably a phenylthio group. The substituted arylthio group can be, for example, a methylphenylthio, ethylphenylthio, propylphenylthio, isopropylphenylthio, methoxyphenylthio, ethoxyphenylthio, methylthiophenylthio, ethylthiophenylthio, biphenylylthio, 4-methanesulfonylphenylthio, methylnaphthylthio, ethylnaphthylthio, propylnaphthylthio, isopropylnaphthylthio, methoxynaphthylthio, ethoxynaphthylthio, methylthionaphthylthio, ethylthionaphthylthio or 4-methanesulfonylnaphthylthio group, and is preferably an arylthio group having 6 to 10 carbon atoms which may have from 1 to 3 substituents $\alpha^b$ mentioned below, more preferably a phenylthio group which may have from 1 to 3 substituents $\alpha^b$ mentioned below on the phenyl moiety, most preferably a methylphenylthio, isopropylphenylthio or methoxyphenylthio group.

In the case where $W^b$ represents an aralkyloxy group having from 7 to 12 carbon atoms which may have from 1 to 5 substituents $\alpha^b$ mentioned below on the aryl moiety, the unsubstituted aralkyloxy group is a group in which a straight- or branched-chain alkyloxy group having from 1 to 4 carbon atoms is substituted with the above aryl group and can be, for example, a benzyloxy, phenethyloxy, 3-phenylpropyloxy, 4-phenylbutyloxy, 1-naphthylmethyloxy or 2-naphthylmethyloxy group, and is preferably an aralkyloxy group having from 7 to 10 carbon atoms, more preferably a benzyloxy or phenethyloxy group (particularly a benzyloxy group). The substituted aralkyloxy group can be, for example, a methylbenzyloxy, methoxybenzyloxy, 2-(methylphenyl)ethoxy, 2-(methoxyphenyl)ethoxy, 3-(methylphenyl)propoxy, 3-(methoxyphenyl)propoxy, 4-(methylphenyl)butoxy or 4-(methoxyphenyl)butoxy group, and is preferably an aralkyloxy group having from 7 to 12 carbon atoms which may have from 1 to 3 substituents $\alpha^b$ mentioned below on the aryl moiety, more preferably a methylbenzyloxy or 2-(methylphenyl)ethoxy group.

In the case where $W^b$ represents an aralkylthio group having from 7 to 12 carbon atoms which may have from 1 to 5 substituents $\alpha^b$ mentioned below on the aryl moiety, the unsubstituted aralkylthio group is a group in which a straight- or branched-chain alkylthio group having from 1 to 4 carbon atoms is substituted with the above aryl group and can be, for example, a benzylthio, phenethylthio, 3-phenylpropylthio, 4-phenylbutylthio, 1-naphthylmethylthio or 2-naphthylmethylthio group, and is preferably a benzylthio or phenethylthio group, more preferably a benzylthio group. The substituted aralkylthio group can be, for example, a methylbenzylthio, methoxybenzylthio, 2-(methylphenyl)ethylthio, 2-(methoxyphenyl)ethylthio, 3-(methylphenyl)propylthio, 3-(methoxyphenyl)propylthio, 4-(methylphenyl)butylthio or 4-(methoxyphenyl)butylthio group, and is preferably an aralkylthio group having from 7 to 12 carbon atoms which may have from 1 to 3 substituents $\alpha^b$ mentioned below on the aryl moiety; more preferably a methylbenzylthio or 2-(methylphenyl)ethylthio group.

In the case where $W^b$ represents an aryloxyalkyl group in which the aryl moiety is an aryl group having from 6 to 10 carbon atoms which may have from 1 to 5 substituents $\alpha^b$ mentioned below and the alkyl moiety is a straight- or branched-chain alkyl group having from 1 to 4 carbon atoms, the aryloxyalkyl group can be, for example, a phenoxymethyl, 2-phenoxyethyl, 3-phenoxypropyl, 4-phenoxybutyl, naphthyloxymethyl, 2-naphthyloxyethyl, 3-naphthyloxypropyl or 4-naphthyloxybutyl group, and is preferably an aryloxyalkyl group in which the aryl moiety is an aryl group having from 6 to 10 carbon atoms which may have from 1 to 3 substituents $\alpha^b$ mentioned below and the alkyl moiety is a straight- or branched-chain alkyl group having from 1 to 4 carbon atoms, more preferably an aryloxyalkyl group in which the aryl moiety has from 6 to 10 carbon atoms and the alkyl moiety is a straight- or branched-chain and has from 1 to 4 carbon atoms, still more preferably a phenoxymethyl, 2-phenoxyethyl, 3-phenoxypropyl or 4-phenoxybutyl group, most preferably a 2-phenoxyethyl or 3-phenoxypropyl group (particularly a 2-phenoxyethyl group).

In the case where $W^b$ represents a 5- to 10-membered monocyclic or bicyclic heteroaromatic group containing from 1 to 4 heteroatoms selected from the group consisting of oxygen, nitrogen and sulfur atoms, the group can be, for example, a furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, quinolyl or benzoxazolyl group, and is preferably a pyrrolyl, imidazolyl, furyl, thienyl or pyridyl group, more preferably a pyrrolyl or imidazolyl group.

In the case where $W^b$ represents a 5- to 10-membered monocyclic or bicyclic heteroaromatic oxy group containing from 1 to 4 heteroatoms selected from the group consisting of oxygen, nitrogen and sulfur atoms, the group can be, for example, a furyloxy, thienyloxy, pyrrolyloxy, azepinyloxy, pyrazolyloxy, imidazolyloxy, oxazolyloxy, isoxazolyloxy, thiazolyloxy, isothiazolyloxy, 1,2,3-oxadiazolyloxy, triazolyloxy, tetrazolyloxy, thiadiazolyloxy, pyranyloxy, pyridyloxy, pyridazinyloxy, pyrimidinyloxy, pyrazinyloxy or benzoxazolyloxy group, and is preferably a furyloxy, thienyloxy, pyrrolyloxy, imidazolyloxy, thiazolyloxy or pyridyloxy group, more preferably a pyridyloxy group.

In the case where $W^b$ represents a 5- to 10-membered monocyclic or bicyclic heteroaromatic thio group containing from 1 to 4 heteroatoms selected from the group consisting of oxygen, nitrogen and sulfur atoms, the group can be, for example, a furylthio, thienylthio, pyrrolylthio, azepinylthio, pyrazolylthio, imidazolylthio, oxazolylthio, isoxazolylthio, thiazolylthio, isothiazolylthio, 1,2,3-oxadiazolylthio, triazolylthio, tetrazolylthio, thiadiazolylthio, pyranylthio, pyridylthio, pyridazinylthio, pyrimidinylthio, pyrazinylthio or benzoxazoylthio group, and is preferably a furylthio, thienylthio, pyrrolylthio, imidazolylthio, thiazolylthio, pyridylthio or benzoxazoylthio group, more preferably a benzoxazoylthio group.

In the case where $W^b$ represents a saturated 5- to 10-membered monocyclic or bicyclic heteroaromatic group containing from 1 to 4 heteroatoms selected from the group consisting of oxygen, nitrogen and sulfur atoms, the group can be, for example, a morpholinyl, thiomorpholinyl, pyrrolidinyl, pyrrolinyl, imidazolidinyl, imidazolinyl, pyrazolidinyl, pyrazolinyl, piperidyl or piperazinyl group, and is preferably a morpholinyl, thiomorpholinyl, pyrrolidinyl, imidazolinyl, piperidyl or piperazinyl group.

In the case where $W^b$ represents a straight- or branched-chain monoalkylamino group in which the alkyl moiety has from 1 to 4 carbon atoms, the monoalkylamino group can be, for example, a methylamino, ethylamino, propylamino, isopropylamino, butylamino, s-butylamino, t-butylamino or isobutylamino group, and is preferably a straight- or branched-chain monoalkylamino group having from 1 to 3 carbon atoms, more preferably a propylamino group.

In the case where $W^b$ represents an N-alkyl-N-arylamino group having a straight- or branched-chain alkyl group having from 1 to 4 carbon atoms and an aryl group having from 6 to 10 carbon atoms which may have from 1 to 5 substituents $\alpha^b$ mentioned below on the aryl moiety, the alkyl-group of the unsubstituted N-alkyl-N-arylamino group can be, for example, a methyl, ethyl, propyl, isopropyl, butyl, isobutyl, s-butyl or t-butyl group, and is preferably a methyl, ethyl, propyl, isopropyl, butyl or isobutyl group, more preferably a methyl or ethyl group. The aryl group can be, for example, a phenyl or naphthyl group, and is preferably a phenyl group. The unsubstituted N-alkyl-N-arylamino group can be, for example, an N-methyl-N-phenylamino, N-ethyl-N-phenylamino, N-propyl-N-phenylamino, N-isopropyl-N-phenylamino, N-butyl-N-phenylamino, N-isobutyl-N-phenylamino or N-methyl-N-naphthylamino group, and is preferably an N-methyl-N-phenylamino or N-ethyl-N-phenylamino group, more preferably an N-ethyl-N-phenylamino group. The substituted N-alkyl-N-arylamino group can be, for example, an N-methyl-N-(methylphenyl)amino, N-ethyl-N-(methylphenyl)amino, N-methyl-N-(methoxyphenyl)amino or N-ethyl-N-(methoxyphenyl)amino group, and is preferably an N-methyl-N-(methylphenyl)amino or N-ethyl-N-(methylphenyl)amino group.

In the case where $W^b$ represents an arylamino group having from 6 to 10 carbon atoms which may have from 1 to 5 substituents $\alpha^b$ mentioned below on the aryl moiety, the unsubstituted arylamino group can be, for example, a phenylamino or naphthylamino group, and is preferably a phenylamino group. The substituted arylamino group can be, for example, a (methylphenyl)amino, (ethylphenyl)amino, (propylphenyl)amino, (isopropylphenyl)amino, (methoxyphenyl)amino, (ethoxyphenyl)amino, (methylthiophenyl)amino, (ethylthiophenyl)amino, biphenylylamino or (methanesulfonylphenyl)amino group, and is preferably a (methylphenyl)amino, (isopropylphenyl)amino or (methoxyphenyl)amino group.

In the case where $W^b$ represents an aralkylamino group having from 7 to 12 carbon atoms which may have from 1 to 5 substituents $\alpha^b$ mentioned below on the aryl moiety, the unsubstituted aralkylamino group is a group in which a straight- or branched-chain alkylamino group having from 1 to 4 carbon atoms is substituted with the above-mentioned aryl group and can be, for example, a benzylamino, phenethylamino, (3-phenylpropyl)amino, (4-phenylbutyl)amino, (1-naphthylmethyl)amino or (2-naphthylmethyl)amino group, and is preferably a benzylamino or phenethylamino group, more preferably a benzylamino group. The substituted aralkylamino group can be, for example, a (methylbenzyl)amino, (methoxybenzyl)amino, [2-(methylphenyl)ethyl]amino, [2-(methoxyphenyl)ethyl]amino, [3-(methylphenyl)propyl]amino, [3-(methoxyphenyl)propyl]amino, [4-(methylphenyl)butyl]amino or [4-(methoxyphenyl)butyl]amino group, and is preferably a (methylbenzyl)amino or [2-(methylphenyl)ethyl]amino group.

In the case where $W^b$ represents an aralkyloxycarbonylamino group having from 7 to 12 carbon atoms which may have from 1 to 5 substituents $\alpha^b$ mentioned below on the aryl moiety, the group can be, for example, a benzyloxycarbonyl group.

In the case where $W^b$ represents an amino group, a straight- or branched-chain monoalkylamino group in which the alkyl group has from 1 to 4 carbon atoms, a straight- or branched-chain dialkylamino group in which the alkyl groups may be the same or different and each has from 1 to 4 carbon atoms, an N-alkyl-N-arylamino group having a straight- or branched-chain alkyl group having from 1 to 4 carbon atoms and an aryl group having from 6 to 10 carbon atoms which may have from 1 to 5 substituents $\alpha^b$ mentioned below on the aryl moiety, an arylamino group having from 6 to 10 carbon atoms which may have from 1 to 5 substituents $\alpha^b$ mentioned below on the aryl moiety, an aralkylamino group having from 7 to 12 carbon atoms which may have from 1 to 5 substituents $\alpha^b$ mentioned below on the aryl moiety or an aralkyloxycarbonylamino group having from 7 to 12 carbon atoms which may have from 1 to 5 substituents $\alpha^b$ mentioned below on the aryl moiety, $W^b$ is preferably: an amino group; a straight- or branched-chain monoalkylamino group in which the alkyl group has from 1 to 4 carbon atoms; a straight- or branched-chain dialkylamino group in which the alkyl groups may be the same or different and each has from 1 to 4 carbon atoms; an N-alkyl-N-arylamino group having a straight- or branched-chain alkyl group having from 1 to 4 carbon atoms and an aryl group having from 6 to 10 carbon atoms which may have from 1 to 5 substituents $\alpha^b$ mentioned below on the aryl moiety; an arylamino group having from 6 to 10 carbon atoms which may have from 1 to 5 substituents $\alpha^b$ mentioned below on the aryl moiety; or an aralkylamino group having from 7 to 12 carbon atoms which may have from 1 to 5 substituents $\alpha^b$ mentioned below on the aryl moiety.

In the case where $R^{5b}$ represents a straight- or branched-chain aliphatic acyl group having from 1 to 8 carbon atoms or an aromatic acyl group having from 7 to 11 carbon atoms, the acyl group can be, for example, a formyl, acetyl, propionyl, butyryl, pentanoyl, hexanoyl, heptanoyl, octanoyl, benzoyl or p-toluoyl group, and is preferably a straight- or branched-chain aliphatic acyl group having from 1 to 8 carbon atoms, more preferably a straight- or branched-chain aliphatic acyl group having from 2 to 5 carbon atoms, most preferably an acetyl group.

In the case where $X^b$ represents an aryl group having from 6 to 10 carbon atoms which may have from 1 to 3 substituents $\alpha^b$ mentioned below, the unsubstituted aryl group can be, for example, a phenyl or naphthyl group, and is preferably a phenyl group. In the case where $X^b$ represents an aryl group which is substituted with from 1 to 3 substituents $\alpha^b$ mentioned below, the number of the substituents is preferably one or two, more preferably one.

In the case where $X^b$ represents a 5- to 10-membered monocyclic or bicyclic heteroaromatic group containing from 1 to 4 heteroatoms selected from the group consisting of oxygen, nitrogen and sulfur atoms which may have from 1 to 3 substituents $\alpha^b$ mentioned below, the unsubstituted heteroaromatic group comprises a monocyclic ring or a bicyclic ring system. In the case where the group is a bicyclic ring system, one of them at least is a heterocyclic ring. In the case of a bicyclic ring system, the group is a condensed ring, and either one ring is a heterocyclic ring and the other is a carbocyclic ring, or both of the rings are heterocyclic rings. The heterocyclic ring is a 5- or 6-membered ring and contains from 1 to 4 heteroatoms selected from the group consisting of nitrogen, oxygen and sulfur atoms. The carbocyclic ring is an aryl group having from 6 to 10 carbon atoms. The monocyclic ring system and the bicyclic ring system are referred to as monocyclic heteroaromatic group and condensed heteroaromatic ring group, respectively. In the case of a ring having four heteroatoms, it is preferred that the four heteroatoms are all nitrogen atoms with no heteroatom selected from the group consisting of oxygen and sulfur atoms. In the case of a ring having three heteroatoms, it is preferred that three, two or one of them are nitrogen atoms and one or two heteroatoms are selected from the group consisting of oxygen and sulfur atoms. In the case of a ring having two heteroatoms, it is preferred that two, one or none of them are nitrogen atoms and none, one or two of the heteroatoms are selected from the group consisting of oxygen and sulfur atoms. In the case where $X^b$ represents a heteroaromatic group which is substituted with from 1 to 3 substituents $\alpha^b$ mentioned below, the number of substituents is preferably one or two, more preferably one.

The unsubstituted monocyclic heteroaromatic group can be, for example, a pyrrolyl group such as 2-pyrrolyl and 3-pyrrolyl; a furyl group such as 2-furyl and 3-furyl; a thienyl group such as 2-thienyl and 3-thienyl; a pyridyl group such as 2-pyridyl, 3-pyridyl and 4-pyridyl; an imidazolyl group such as 2-imidazolyl and 4-imidazolyl; a pyrazolyl group such as 3-pyrazolyl and 4-pyrazolyl; an oxazolyl group such as 2-oxazolyl, 4-oxazolyl and 5-oxazolyl; an isoxazolyl group such as 3-isoxazolyl, 4-isoxazolyl and 5-isoxazolyl; a thiazolyl group such as 2-thiazolyl, 4-thiazolyl and 5-thiazolyl; an isothiazolyl group such as 3-isothiazolyl, 4-isothiazolyl and 5-isothiazolyl; a triazolyl group such as 1,2,3-triazol-4-yl and 1,2,4-triazol-3-yl; a thiadiazolyl group such as 1,3,4-thiadiazol-2-yl; an oxadiazolyl group such as 1,3,4-oxadiazol-2-yl; a tetrazolyl group such as 5-tetrazolyl; a pyridazinyl group such as 3-pyridazinyl and 4-pyridazinyl; a pyrimidinyl group such as 2-pyrimidinyl, 4-pyrimidinyl and 5-pyrimidinyl; a pyrazinyl group; an oxazinyl group such as 1,4-oxazin-2-yl and 1,4-oxazin-3-yl; or a thiazinyl group such as 1,4-thiazin-2-yl and 1,4-thiazin-3-yl.

The unsubstituted condensed aromatic heterocyclic ring group can be, for example, an indolyl group such as indol-2-yl, indol-3-yl, indol-4-yl, indol-5-yl, indol-6-yl and indol-7-yl; an indazolyl group such as indazol-2-yl, indazol-3-yl, indazol-4-yl, indazol-5-yl, indazol-6-yl and indazol-7-yl; a benzofuranyl group such as benzofuran-2-yl, benzofuran-3-yl, benzofuran-4-yl, benzofuran-5-yl, benzofuran-6-yl and benzofuran-7-yl; a benzothiophenyl group such as benzothiophen-2-yl, benzothiophen-3-yl, benzothiophen-4-yl, benzothiophen-5-yl, benzothiophen-6-yl and benzothiophen-7-yl; a benzimidazolyl group such as benzimidazol-2-yl, benzimidazol-4-yl, benzimidazol-5-yl, benzimidazol-6-yl and benzimidazol-7-yl; a benzoxazolyl group such as benzoxazol-2-yl, benzoxazol-4-yl, benzoxazol-5-yl, benzoxazol-6-yl and benzoxazol-7-yl; a benzothiazolyl group such as benzothiazol-2-yl, benzothiazol-4-yl, benzothiazol-5-yl, benzothiazol-6-yl and benzothiazol-7-yl; a quinolyl group such as 2-quinolyl, 3-quinolyl, 4-quinolyl, 5-quinolyl, 6-quinolyl, 7-quinolyl and 8-quinolyl; an isoquinolyl group such as 1-isoquinolyl, 3-isoquinolyl, 4-isoquinolyl and 8-isoquinolyl; a benzoxazinyl group such as 1,4-benzoxazin-2-yl and 1,4-benzoxazin-3-yl; a benzothiazinyl group such as 1,4-benzothiazin-2-yl and 1,4-benzothiazin-3-yl; a pyrrolo[2,3-b]pyridyl group such as pyrrolo[2,3-b]pyrid-2-yl and pyrrolo[2,3-b]pyrid-3-yl; a furo[2,3-b]pyridyl group such as furo[2,3-b]pyrid-2-yl and furo[2,3-b]pyrid-3-yl; a thieno[2,3-b]pyridyl group such as thieno[2,3-b]pyrid-2-yl and thieno[2,3-b]pyrid-3-yl; a naphthyridinyl group such as 1,8-naphthyridin-2-yl, 1,8-naphthyridin-3-yl, 1,5-naphthyridin-2-yl and 1,5-naphthyridin-3-yl; an imidazopyridyl group such as imidazo[4,5-b]pyrid-2-yl and imidazo[4,5-b]pyrid-5-yl; an oxazolopyridyl group such as oxazolo[4,5-b]pyrid-2-yl and oxazolo[5,4-b]pyrid-2-yl; or a thiazolopyridyl group-such as thiazolo[4,5-b]pyrid-2-yl and thiazolo[4,5-c]pyrid-2-yl.

The monocyclic heteroaromatic group is preferably a 5- or 6-membered ring group having from 1 to 3 heteroatoms selected from the group consisting of nitrogen, oxygen and sulfur atoms, which can be a pyrrolyl, furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl or pyrazinyl group as exemplified above. The condensed heteroaromatic group is preferably a condensed-ring group of a benzene ring with the 5- or 6-membered heteroaromatic ring having from 1 to 3 heteroatoms selected from the group consisting of nitrogen, oxygen and sulfur atoms mentioned above, which can be an indolyl, benzofuranyl, benzothiophenyl, benzoimidazolyl, benzoxazolyl, benzothiazolyl, quinolyl or isoquinolyl group as exemplified above.

Preferred heteroaromatic groups are imidazolyl, oxazolyl, pyridyl, indolyl, quinolyl and isoquinolyl groups, more preferred are pyridyl, indolyl, quinolyl and isoquinolyl groups, still more preferred are pyridyl, quinolyl and isoquinolyl groups, and particularly preferred is pyridyl group.

In the case where the above-mentioned $X^b$ represents an aryl group having from 6 to 10 carbon atoms or a 5- to 10-membered monocyclic or bicyclic heteroaromatic group containing from 1 to 4 heteroatoms selected from the group consisting of oxygen, nitrogen and sulfur atoms, the aryl group and the heteroaromatic group may have from 1 to 3 substituents $\alpha^b$ mentioned above.

In the case where the substituent $\alpha^b$ represents a straight- or branched-chain alkyl group having from 1 to 6 carbon atoms, a straight- or branched-chain alkoxy group having from 1 to 4 carbon atoms, a straight- or branched-chain alkylthio group having from 1 to 4 carbon atoms, a halogen atom or a straight- or branched-chain dialkylamino group in which the alkyl groups are the same or different from each other and each has from 1 to 4 carbon atoms, these groups include the same groups as exemplified for the above-mentioned $R^{3b}$. However, in the case where the substituent $\alpha^b$ represents a straight- or branched-chain alkyl group having from 1 to 6 carbon atoms, the alkyl group is preferably a methyl, ethyl, propyl, isopropyl, butyl or t-butyl group, more preferably a methyl, isopropyl or t-butyl group.

In the case where the substituent $\alpha^b$ represents an aralkyloxycarbonylamino group in which the aralkyl moiety has from 7 to 12 carbon atoms, the group can be, for example, a benzyloxycarbonylamino group.

In the case where the substituent $\alpha^b$ represents a straight- or branched-chain halogenated alkyl group having from 1 to 4 carbon atoms, the halogenated alkyl group can be, for example, a chloromethyl, bromomethyl, fluoromethyl, iodomethyl, difluoromethyl, trifluoromethyl, pentafluoroethyl, 2,2,2-trifluoroethyl, 2,2,2-trichloroethyl or trichloromethyl group, and is preferably a fluoromethyl group having from 1 to 3 fluorine atoms, more preferably a trifluoromethyl group.

In the case where the substituent $\alpha^b$ represents a straight- or branched-chain aliphatic acyloxy group having from 1 to 5 carbon atoms, the acyloxy group can be, for example, a formyloxy, acetoxy, propionyloxy, butyryloxy, acroyloxy, methacryloyloxy or crotonoyloxy group, and is preferably an alkanoyloxy group having from 1 to 4 carbon atoms, more preferably an alkanoyloxy group having one or two carbon atoms, most preferably an acetoxy group.

In the case where the substituent $\alpha^b$ represents a straight- or branched-chain halogenated alkoxy group having from 1 to 4 carbon atoms, the halogenated alkoxy group can be, for example, a chloromethoxy, bromomethoxy, fluoromethoxy, iodomethoxy, difluoromethoxy, trifluoromethoxy, pentafluoroethoxy, 2,2,2-trifluoroethoxy, 2,2,2-trichloroethoxy, trichloromethoxy or 2,2,3,3-tetrafluoropropoxy group, and is preferably a straight- or branched-chain halogenated alkoxy group having from 1 to 3 carbon atoms, more preferably a methoxy group having from 1 to 3 fluorine atoms or a 2,2,3,3-tetrafluoropropoxy group, most preferably a trifluoromethoxy or 2,2,3,3-tetrafluoropropoxy group (particularly a 2,2,3,3-tetrafluoropropoxy group).

In the case where the substituent $\alpha^b$ represents a straight- or branched-chain aliphatic acyl group having from 1 to 5 carbon atoms, the acyl group can be, for example, a formyl, acetyl, propionyl, butyryl, acroyl, methacroyl or crotonoyl group, and is preferably a straight- or branched-chain aliphatic acyl group having two or three carbon atoms, more preferably an acetyl group.

In the case where the substituent $\alpha^b$ represents a straight- or branched-chain alkylenedioxy group having from 1 to 4 carbon atoms, the alkylenedioxy group can be, for example, a methylenedioxy, ethylenedioxy, trimethylenedioxy, tetramethylenedioxy or propylenedioxy group, and is preferably a methylenedioxy or ethylenedioxy group, more preferably a methylenedioxy group.

In the case where the substituent $\alpha^b$ represents a straight- or branched-chain alkylsulfonyl group having from 1 to 4 carbon atoms, the alkylsulfonyl group can be, for example, a methanesulfonyl, ethanesulfonyl, propanesulfonyl, isopropanesulfonyl, butanesulfonyl, isobutanesulfonyl, s-butanesulfonyl or t-butanesulfonyl group, and is preferably a methanesulfonyl, ethanesulfonyl or isopropanesulfonyl group, more preferably an alkylsulfonyl group having one or two carbon atoms (particularly a methanesulfonyl group). In the case where the substituent $\alpha^b$ represents a straight- or branched-chain monoalkylamino group in which the alkyl group has from 1 to 4 carbon atoms, the group can be, for example, a methylamino, ethylamino, propylamino, isopropylamino, butylamino, isobutylamino, s-butylamino or t-butylamino group, and is preferably a methylamino, ethylamino, isopropylamino or t-butylamino group, more preferably a methylamino group.

In the case where the substituent $\alpha^b$ represents a 5- to 10-membered monocyclic or bicyclic saturated heterocyclic group containing 1 to 4 heteroatoms selected from the group consisting of oxygen, nitrogen and sulfur atoms, the saturated heterocyclic group can be, for example, a morpholinyl, thiomorpholinyl, pyrrolidinyl, pyrrolinyl, imidazolidinyl, imidazolinyl, pyrazolidinyl, pyrazolinyl, piperidyl or piperazinyl group, and is preferably a morpholinyl, thiomorpholinyl, pyrrolidinyl, piperidyl or piperazinyl group (particularly a piperidyl group).

In the case where $X^b$ represents a substituted or unsubstituted aryl group having from 6 to 10 carbon atoms or a 5- to 10-membered monocyclic or bicyclic substituted or unsubstituted heteroaromatic group containing 1 to 4 heteroatoms selected from the group consisting of oxygen, nitrogen and sulfur atoms, specific preferred examples of these groups are phenyl, 1-naphthyl, 2-naphthyl, m-tolyl, p-tolyl, 3-ethylphenyl, 4-ethylphenyl, 3-isopropylphenyl, 4-isopropylphenyl, 3-t-butylphenyl, 4-t-butylphenyl, 4-chloromethylphenyl, 4-bromomethylphenyl, 4-fluoromethylphenyl, 4-iodomethylphenyl, 3-difluoromethylphenyl, 4-trifluoromethylphenyl, 4-pentafluoroethylphenyl, 4-trichloromethylphenyl, 3-hydroxyphenyl, 4-hydroxyphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, phenethyloxyphenyl, 1-naphthylmethoxyphenyl, 3-methylthiophenyl, 4-methylthiophenyl, 3-ethylthiophenyl, 4-ethylthiophenyl, 3-isopropylthiophenyl, 4-isopropylthiophenyl, 3-methanesulfonylphenyl, 4-methanesulfonylphenyl, 3-ethanesulfonylphenyl, 4-ethanesulfonylphenyl, 3-isopropanesulfonylphenyl, 4-isopropanesulfonylphenyl, 3-fluorophenyl, 4-fluorophenyl, 3-chlorophenyl, 4-chlorophenyl, 3-bromophenyl, 4-bromophenyl, 3-nitrophenyl, 4-aminophenyl, 3-methylaminophenyl, 4-ethylaminophenyl, 3-propylaminophenyl, 4-butylaminophenyl, 3-dimethylaminophenyl, 4-diethylaminophenyl, 3-dipropylaminophenyl, 4-dibutylaminophenyl, 3-benzylaminophenyl, 4-benzylphenyl, 3-phenethylphenyl, 4-(1-naphthylmethyl)phenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(4-hydroxy-3,5-dimethylphenyl)phenyl, 3-(4-methoxyphenyl)phenyl, 4-(2-methoxyphenyl)phenyl, 4-(3-methoxyphenyl)phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl)phenyl, 4-(3-hydroxymethylphenyl)phenyl, 4-(4-hydroxymethylphenyl)phenyl, 4-(3-fluorophenyl)phenyl, 4-(4-fluorophenyl)phenyl, 4-(3-chlorophenyl)phenyl, 4-(4-chlorophenyl)phenyl, 4-(3-bromophenyl)phenyl, 4-(4-bromophenyl)phenyl, 3-(3,4-methylenedioxyphenyl)phenyl, 4-(3,4-methylenedioxyphenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl) phenyl, 4-(3-N,N-dimethylaminomethylphenyl)phenyl, 4-(4-N,N-dimethylaminomethylphenyl)phenyl, 3-benzylphenyl, 4-benzylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(imidazol-1-yl)phenyl, 4-(imidazol-1-yl)phenyl, 3-(1-methylimidazol-4-yl)phenyl, 4-(1-methylimidazol-4-yl)phenyl, 3-(2-furyl)phenyl, 4-(2-furyl)phenyl, 3-(2-thienyl)phenyl, 4-(2-thienyl)phenyl, 3-(3-thienyl)phenyl, 4-(3-thienyl)phenyl, 3-(2-pyridyl)phenyl, 4-(2-pyridyl)phenyl, -4-(2-trifluoromethylpyridin-5-yl)phenyl, 4-(2-methoxypyridin-5-yl)phenyl, 4-(2-nitropyridin-5-yl)phenyl, 4-(2-N,N-dimethylaminopyridin-5-yl)phenyl, 3-(3-pyridyl)phenyl, 4-(3-pyridyl)phenyl, 3-(4-pyridyl)phenyl, 4-(4-pyridyl)phenyl, 4-(imidazol-1-ylthio)phenyl, 4-(2-furylthio)phenyl, 4-(2-thienylthio)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino) phenyl, 4-(N-methyl-2-pyridylsulfonylamino)phenyl, 3-(3-pyridylsulfonylamino)phenyl, 3-(N-methyl-3-pyridylsulfonylamino)phenyl, 4-(3-pyridylsulfonylamino) phenyl, 4-(N-methyl-3-pyridylsulfonylamino)phenyl, 3-(oxazol-2-yl)phenyl, 4-(oxazol-2-yl)phenyl, 3-(oxazol-4-yl)phenyl, 4-(oxazol-4-yl)phenyl, 3-(oxazol-5-yl)phenyl, 4-(oxazol-5-yl)phenyl, 3-(thiazol-2-yl)phenyl, 4-(thiazol-2-yl)phenyl, 3-(thiazol-4-yl)phenyl, 4-(thiazol-4-yl)phenyl, 3-(thiazol-57yl)phenyl, 4-(thiazol-5-yl)phenyl, 4-(piperidin-1-yl)phenyl, 1-methyl-2-pyrrolyl, 1-phenyl-2-pyrrolyl, 1-benzyl-2-pyrrolyl, 5-methyl-2-furyl, 5-phenyl-2-furyl, 5-methyl-2-thienyl, 5-phenyl-2-thienyl, 5-methyl-3-thienyl, 5-phenyl-3-thienyl, 1-methyl-3-pyrazolyl, 1-phenyl-3-pyrazolyl, 3-imidazolyl, 1-methyl-2-imidazolyl, 1-phenyl-2-imidazolyl, 1-methyl-4-imidazolyl, 1-phenyl-4-imidazolyl, 1-methyl-2-phenyl-4-imidazolyl, 1,5-dimethyl-2-phenyl-4-imidazolyl, 1,4-dimethyl-2-phenyl-5-imidazolyl, 4-oxazolyl, 5-oxazolyl, 2-methyl-4-oxazolyl, 2-phenyl-4-oxazolyl, 2-methyl-5-oxazolyl, 2-phenyl-5-oxazolyl, 4-methyl-2-phenyl-5-oxazolyl, 5-methyl-2-phenyl-4-oxazolyl, 4-thiazolyl, 5-thiazolyl, 2-methyl-4-thiazolyl, 2-phenyl-4-thiazolyl, 2-methyl-5-thiazolyl, 2-phenyl-5-thiazolyl, 4-methyl-2-phenyl-5-thiazolyl, 5-methyl-2-phenyl-4-thiazolyl, 1-methyl-3-pyrazolyl, 1-phenyl-3-pyrazolyl, 3-methyl-5-isoxazolyl, 3-phenyl-5-isoxazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-(4-methoxyphenyl)-5-pyridyl, 2-(4-fluorophenyl)-5-pyridyl, 2-hydroxy-5-pyridyl, 2-methoxy-5-pyridyl, 2-ethoxy-5-pyridyl, 2-isopropoxy-5-pyridyl, 2-(2,2,3,3-tetrafluoropropoxyphenyl)-5-pyridyl, 2-benzyloxy-5-pyridyl, 2-methylthio-5-pyridyl, 2-ethylthio-5-pyridyl, 2-isopropylthio-5-pyridyl, 2-methanesulfonyl-5-pyridyl, 2-ethanesulfonyl-5-pyridyl, 2-isopropanesulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-methyl-4-pyrimidinyl, 2-phenyl-4-pyrimidinyl, 2-methoxy-4-pyrimidinyl, 2-ethoxy-4-pyrimidinyl, 2-isopropoxy-4-pyrimidinyl, 2-methylthio-4-pyrimidinyl, 2-ethylthio-4-pyrimidinyl, 2-isopropylthio-4-pyrimidinyl, 2-phenylthio-4-pyrimidinyl, 2-methanesulfonyl-4-pyrimidinyl, 2-ethanesulfonyl-4-pyrimidinyl, 2-isopropylsulfonyl-4-pyrimidinyl, 2-phenylsulfonyl-4-pyrimidinyl, 2-methyl-5-pyrimidinyl, 2-phenyl-5-pyrimidinyl, 2-methoxy-5-pyrimidinyl, 2-ethoxy-5-pyrimidinyl, 2-isopropoxy-5-pyrimidinyl, 2-methylthio-5-pyrimidinyl, 2-ethylthio-5-pyrimidinyl, 2-isopropylthio-5-pyrimidinyl, 2-phenylthio-5-pyrimidinyl, 2-methanesulfonyl-5-pyrimidinyl, 2-ethanesulfonyl-5-pyrimidinyl, 2-isopropylsulfonyl-5-pyrimidinyl, 2-phenylsulfonyl-5-pyrimidinyl, 2-indolyl, 3-indolyl, 1-methyl-2-indolyl, 1-methyl-3-indolyl, 2-benzimidazolyl, 1-methyl-2-benzimidazolyl, 2-benzoxazolyl, 2-benzothiazolyl, 2-quinolyl, 3-quinolyl, 4-quinolyl, 1-isoquinolyl, 3-isoquinolyl, 4-isoquinolyl and 8-isoquinolyl groups;

preferably phenyl, 1-naphthyl, 2-naphthyl, m-tolyl, p-tolyl, 3-ethylphenyl, 4-ethylphenyl, 3-isopropylphenyl, 4-isopropylphenyl, 4-trifluoromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, 3-methylthiophenyl, 4-methylthiophenyl, 3-ethylthiophenyl, 4-ethylthiophenyl, 3-methanesulfonylphenyl, 4-methanesulfonylphenyl, 3-ethanesulfonylphenyl, 4-ethanesulfonylphenyl, 3-fluorophenyl, 4-fluorophenyl, 3-chlorophenyl, 4-chlorophenyl, 4-diethylaminophenyl, 3-benzylphenyl, 4-benzylphenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(4-hydroxy-3,5-dimethylphenyl)phenyl, 3-(4-methoxyphenyl)phenyl, 4-(2-methoxyphenyl)phenyl, 4-(3-methoxyphenyl)phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl)phenyl, 4-(3-hydroxymethylphenyl)phenyl, 4-(4-hydroxymethylphenyl)phenyl, 4-(3-fluorophenyl)phenyl, 4-(4-fluorophenyl)phenyl, 4-(3-chlorophenyl)phenyl, 4-(4-chlorophenyl)phenyl, 3-(3,4-methylenedioxyphenyl)phenyl, 4-(3,4-methylenedioxyphenyl)phenyl, 2-formylphenyl, 3-formylphenyl, 4-formylphenyl, 3-carboxyphenyl, 4-carboxyphenyl, 3-N,N-dimethylaminomethylphenyl, 4-N,N-dimethylaminomethylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 4-(2-trifluoromethylpyridin-5-yl)phenyl, 4-(2-methoxypyridin-5-yl)phenyl, 4-(2-nitropyridin-5-yl)phenyl, 4-(2-N,N-dimethylaminopyridin-5-yl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino)phenyl, 3-(N-methyl-3-pyridylsulfonylamino)phenyl, 4-(3-pyridylsulfonylamino)phenyl, 4-(N-methyl-3-pyridylsulfonylamino)phenyl, 4-(1-piperidinyl)phenyl, 3-imidazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-isopropylthio-5-pyridyl, 2-methanesulfonyl-5-pyridyl, 2-ethanesulfonyl-5-pyridyl, 2-isopropanesulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 2-(4-methoxyphenyl)-5-pyridyl, 2-(4-fluorophenyl)-5-pyridyl, 3-methyl-6-pyridyl, 3-phenyl-6-pyridyl, 2-methyl-6-pyridyl, 2-phenyl-6-pyridyl, 2-quinolyl, 3-quinolyl, 4-quinolyl, 1-isoquinolyl, 3-isoquinolyl, 4-isoquinolyl and 8-isoquinolyl groups;

more preferably phenyl, m-tolyl, p-tolyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-chlorophenyl, 4-chlorophenyl, 3-benzylphenyl, 4-benzylphenyl, 3-biphenylyl, 4-biphenylyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(2-methoxyphenyl)phenyl, 4-(3-methoxyphenyl)phenyl, 4-(4-methoxyphenyl)phenyl, 4-(4-hydroxy-3,5-dimethylphenyl)phenyl, 4-(4-fluorophenyl)phenyl, 4-(4-chlorophenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl)phenyl, 4-(3-hydroxymethylphenyl)phenyl, 4-(4-hydroxymethylphenyl)phenyl, 4-(3-N,N-dimethylaminomethylphenyl)phenyl, 4-(4-N,N-dimethylaminomethylphenyl)phenyl, 3-phenoxyphenyl, 4-phenoxyphenyl, 3-phenylthiophenyl, 4-phenylthiophenyl 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridylphenyl, 4-(3-trifluoromethylpyridin-6-yl)phenyl, 4-(3-methoxypyridin-6-yl)phenyl, 4-(3-nitropyridin-6-yl)phenyl, 4-(3-N,N-dimethylaminopyridin-6-yl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridyithio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 2-pyridyl, 3-pyridyl, 4-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-methanesulfonyl-5-pyridyl, 2-ethanesulfonyl-5-pyridyl, 2-benzyl-5-pyridyl, 2-phenyl-5-pyridyl, 2-(4-methoxyphenyl)-5-pyridyl, 2-(4-fluorophenyl)-5-pyridyl, 3-phenyl-5-pyridyl, 2-phenyl-6-pyridyl, 3-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 2-methyl-5-pyridyl, 3-quinolyl, 3-methyl-5-pyridyl, 3-quinolyl and 3-indolyl groups;

most preferably phenyl, p-tolyl, 4-fluorophenyl, 4-benzylphenyl, 4-biphenylyl, 4-(4-trifluoromethylphenyl)phenyl, 4-(2-hydroxyphenyl)phenyl, 4-(3-hydroxyphenyl)phenyl, 4-(4-hydroxyphenyl)phenyl, 4-(2-methoxyphenyl)phenyl, 4-(3-methoxyphenyl)phenyl, 4-(4-methoxyphenyl)phenyl, 4-(4-hydroxy-3,5-dimethylphenyl)phenyl, 4-(4-fluorophenyl)phenyl, 4-(4-chlorophenyl)phenyl, 4-(2-formylphenyl)phenyl, 4-(3-formylphenyl)phenyl, 4-(4-formylphenyl)phenyl, 4-(3-carboxyphenyl)phenyl, 4-(4-carboxyphenyl)phenyl, 4-(3-hydroxymethylphenyl)phenyl, 4-(4-hydroxymethylphenyl)phenyl, 4-(3-N,N-dimethylaminomethylphenyl)phenyl, 4-(4-N,N-dimethylaminomethylphenyl)phenyl, 4-phenoxyphenyl, 4-phenylthiophenyl, 4-phenylsulfonylphenyl, 4-(phenylsulfonylamino)phenyl, 4-(2-pyridyl)phenyl, 4-(3-trifluoromethylpyridin-6-yl)phenyl, 4-(3-methoxypyridin-6-yl)phenyl, 4-(3-nitropyridin-6-yl)phenyl, 4-(3-N,N-dimethylaminopyridin-6-yl)phenyl, 4-(3-pyridyl)phenyl, 4-(4-pyridyl)phenyl, 2-pyridyl, 3-pyridyl, 4-pyridyl, 2-methoxy-5-pyridyl, 2-ethoxy-5-pyridyl, 2-isopropoxy-5-pyridyl, 2-(2,2,3,3-tetrafluoropropoxy)-5-pyridyl, 2-benzyloxy-5-pyridyl, 2-methylthio-5-pyridyl, 2-ethylthio-5-pyridyl, 2-methanesulfonyl-5-pyridyl, 2-ethanesulfonyl-5-pyridyl, 2-benzyl-5-pyridyl, 2-phenyl-5-pyridyl, 3-phenyl-5-pyridyl, 3-phenyl-6-pyridyl, 2-(4-methoxyphenyl)-5-pyridyl, 2-(4-fluorophenyl)-5-pyridyl, 2-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 2-methyl-5-pyridyl and 3-methyl-5-pyridyl groups.

In the case where $Y^b$ represents a group of the formula: >N—$R^{5b}$ (wherein $R^{5b}$ represents a hydrogen atom, a straight- or branched-chain alkyl group having from 1 to 6 carbon atoms (the alkyl group has the same meaning as described above in the definition of $R^{3b}$) or a straight- or branched-chain aliphatic acyl group having from 1 to 8 carbon atoms (the aliphatic acyl group can be, for example, an alkanoyl group having from 1 to 8 carbon atoms or an alkenoyl group having from 3 to 8 carbon atoms) or an aromatic acyl group having from 7 to 11 carbon atoms), the group of the formula: >N—$R^{5b}$ can be, for example, an imino, methylimino, ethylimino, propylimino, isopropylimino, butylimino, isobutylimino, s-butylimino, t-butylimino, pentylimino, 1-methylbutylimino, 2-methylbutylimino, 3-methylbutylimino, 1,1-dimethylpropylimino, 1,2-dimethylpropylimino, 2,2-dimethylpropylimino, 1-ethylpropylimino, hexylimino, 1-methylpentylimino, 2-methylpentylimino, 3-methylpentylimino, 4-methylpentylimino, 1,1-dimethylbutylimino, 1,2-dimethylbutylimino, 1,3-dimethylbutylimino, 2,2-dimethylbutylimino, 2,3-dimethylbutylimino, 3,3-dimethylbutylimino, 1-ethylbutylimino, 1,1,2-trimethylpropylimino, 1,2,2-trimethylpropylimino, acetylimino, propionylimino, butyrylimino, pentanoylimino, hexanoylimino, heptanoylimino, octanoylimino, benzoylimino or p-toluoylimino group, and is preferably an imino, straight- or branched-chain alkylimino having from 1 to 4 carbon atoms or acetylimino group, most preferably an imino, methylimino, ethylimino or acetylimino group.

The amidocarboxylic acid derivatives of general formula (Ib) of the present invention can be converted into acid addition salts according to conventional methods in the case where they have a basic group. Such salts can be salts of hydrohalogenic acids such as hydrofluoric acid, hydrochloric acid, hydrobromic acid and hydroiodic acid; inorganic acid salts such as nitrate, perchlorate, sulfate and phosphate; salts of lower alkanesulfonic acids such as methanesulfonic acid, trifluoromethanesulfonic acid and ethanesulfonic acid; salts of arylsulfonic acids such as benzenesulfonic acid and p-toluenesulfonic acid; salts of amino acids such as glutamic acid and aspartic acid; and salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid; and are preferably salts of hydrohalogenic acids.

Furthermore, the amidocarboxylic acid derivatives of the formula (Ib) can be converted into metal salts according to conventional methods since they have a carboxyl group. Such salts can be alkali metal salts such as lithium, sodium and potassium; alkaline earth metal salts such as calcium, barium and magnesium; aluminum salts; and the like; and are preferably alkali metal salts.

The amidocarboxylic acid derivatives of the general formula (Ib) of the present invention can be converted into pharmacologically acceptable esters according to conventional methods. The pharmacologically acceptable esters of the amidocarboxylic acid derivatives of formula (Ib) are not particularly limited as long as they can be used medically and their pharmacological acceptability is comparable with that of the amidocarboxylic acids of formula (Ib).

The ester of the amidocarboxylic acid derivatives of formula (Ib) of the present invention can be a straight- or branched-chain alkyl group having from 1 to 6 carbon atoms; an aralkyl group having from 7 to 19 carbon atoms; a straight- or branched-chain alkyl group having from 1 to 5 carbon atoms which is substituted with a straight- or branched-chain alkanoyloxy group having from 1 to 6 carbon atoms; a straight- or branched-chain alkyl group having from 1 to 5 carbon atoms which is substituted with a straight- or branched-chain alkyloxycarbonyloxy group having from 1 to 6 carbon atoms; a straight- or branched-chain alkyl group having from 1 to 5 carbon atoms which is substituted with a cycloalkylcarbonyloxy group having from 5 to 7 carbon atoms; a straight- or branched-chain alkyl group having from 1 to 5 carbon atoms which is substituted with a cycloalkyloxycarbonyloxy group having from 5 to 7 carbon atoms; a straight- or branched-chain alkyl group having from 1 to 5 carbon atoms which is substituted with an arylcarbonyloxy group having from 6 to 10 carbon atoms; a straight- or branched-chain alkyl group having from 1 to 5 carbon atoms which is substituted with an aryloxycarbonyloxy group having from 6 to 10 carbon atoms; or a 2-oxo-1,3-dioxolen-4-ylmethyl group having a straight- or branched-chain alkyl group having from 1 to 6 carbon atoms as a substituent at the 5-position.

The straight- or branched-chain alkyl group having from 1 to 4 carbon atoms and the straight or branched chain alkyl group having from 1 to 6 carbon atoms can be a methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group, and are preferably a straight- or branched-chain alkyl group having from 1 to 4 carbon atoms, more preferably a methyl, ethyl, propyl, isopropyl, butyl or isobutyl group, most preferably a methyl or ethyl group.

The aralkyl group having from 7 to 19 carbon atoms can be a benzyl, phenethyl, 3-phenylpropyl, 4-phenylbutyl, 1-naphthylmethyl, 2-naphthylmethyl or diphenylmethyl group, and is preferably a benzyl group.

The cycloalkyl group having from 5 to 7 carbon atoms can be a cyclopentyl, cyclohexyl or cycloheptyl group, and is preferably a cyclohexyl group.

The aryl group having from 6 to 10 carbon atoms can be a phenyl or naphthyl group, and is preferably a phenyl group.

Specific examples of the preferred ester residues include methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethlyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopenxtanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl and 5-methyl-2-oxo-1,3-dioxolen-4-ylmethyl groups.

Incidentally, the amidocarboxylic acid derivatives of the general formula (Ib), pharmacologically acceptable salts thereof and pharmacologically acceptable esters thereof have various isomers. For example, optical isomers derived from the asymmetric carbon at the $\alpha^b$-position of the carboxylic acid exist. In the formula (Ib), all of the stereoisomers based on the asymmetric carbon atom and equal and unequal mixtures of these isomers are shown by a single formula. Therefore, the present invention includes all of these isomers and mixtures of these isomers. Moreover, in the present invention, in the case where the amidocarboxylic acid derivatives of the formula (Ib), pharmacologically acceptable salts thereof and pharmacologically acceptable esters thereof form solvates (for example, hydrates), the present invention includes all of these solvates.

Furthermore, the present invention includes all compounds which are metabolized in vivo to be converted to the amidocarboxylic acid derivatives of the formula (Ib) or salts thereof, for example, so-called prodrugs such as amide derivatives.

In the above general formulae (Ic), (Id) and (Ie) of the invention, when $R_{1c}$, $R_{1d}$, $R_{1e}$, $R_{2c}$, $R_{2d}$, $R_{2e}$, $R_{3c}$, $R_{3d}$, $R_{3e}$, $X_c$, $X_d$, $X_e$, $Z_{1c}$, $Z_{1d}$, $Z_{1e}$, $Z_{3c}$, $Z_{3d}$, $Z_{3e}$, $\alpha_{1c}$, $\alpha_{1d}$, $\alpha_{1e}$, $\gamma_{1c}$, $\gamma_{1d}$ and $\gamma_{1e}$ represent a "$C_1$–$C_6$ alkyl group", said group means a straight- or branched-chain alkyl group having from 1 to 6 carbon atoms. Examples of said group are methyl, ethyl, propyl, isopropyl, butyl, isobutyl, s-butyl, t-butyl, pentyl, s-pentyl, isopentyl, 2-methylbutyl, neopentyl, 1-ethylpropyl, hexyl, 4-methylpentyl (isohexyl), 3-methylpentyl, 2-methylpentyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. $C_1$–$C_4$ alkyl groups are preferred, and $C_1$–$C_2$ alkyl groups are more preferred.

In the case where $R_{1c}$, $R_{1d}$, $R_{1e}$, $R_{2c}$, $R_{2d}$, $R_{2e}$, $R_{3c}$, $R_{3d}$, $R_{3e}$, $Z_{1c}$, $Z_{1d}$, $Z_{1e}$, $Z_{3c}$, $Z_{3d}$ and $Z_{3e}$ represent a "$C_6$–$C_{10}$ aryl group (optionally having from 1–5 substituting moieties $\alpha_{1c}$, $\alpha_{1d}$ and $\alpha_{1e}$ described hereafter)", in the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_6$–$C_{10}$ aryl group (optionally having from 1–5 substituting moieties $\beta_{1c}$, $\beta_{1d}$ and $\beta_{1e}$ hereafter described)", in the case where $\beta_{1c}$, $\beta_{1d}$ and $\beta_{1e}$ represent a "$C_6$–$C_{10}$ aryl group (optionally having from 1–5 substituting moieties $\gamma_{1c}$, $\gamma_{1d}$ and $\gamma_{1e}$ hereafter described)", and in the case where $Z_{2c}$, $Z_{2d}$ and $Z_{2e}$ represent a "$C_6$–$C_{10}$ aryl group (optionally having from 1–5 substituting moieties $\alpha_{2c}$, $\alpha_{2d}$ and $\alpha_{2e}$ described hereafter)", said $C_6$–$C_{10}$ aryl group illustratively includes phenyl, indenyl or naphthyl group.

In the case where $R_{1c}$, $R_{1d}$, $R_{1e}$, $R_{2c}$, $R_{2d}$, $R_{2e}$, $R_{3c}$, $R_{3d}$, $R_{3e}$, $Z_{1c}$, $Z_{1d}$, $Z_{1e}$, $Z_{3c}$, $Z_{3d}$ and $Z_{3e}$ represent a "$C_7$–$C_{16}$ aralkyl group (optionally having from 1–5 substituting moieties $\alpha_{1c}$, $\alpha_{1d}$ and $\alpha_{1e}$ hereafter described on the aryl moiety thereof)", in the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_7$–$C_{16}$ aralkyl group (optionally having from 1–5 substituting moieties $\beta_{1c}$, $\beta_{1d}$ and $\beta_{1e}$ hereafter described on the aryl moiety thereof)" and in the case where $\beta_{1c}$, $\beta_{1d}$ and $\beta_{1e}$ represent a "$C_7$–$C_{16}$ aralkyl group (optionally having from 1–5 substituting moieties $\gamma_{1c}$, $\gamma_{1d}$ and $\gamma_{1e}$ hereafter described on the aryl moiety thereof)", said $C_7$–$C_{16}$ aralkyl group means a $C_1$–$C_6$ alkyl group which is substituted with said $C_6$–$C_{10}$ aryl group. Examples of said aralkyl group are benzyl, naphthylmethyl, indenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 5-phenylpentyl, 5-naphthylpentyl, 6-phenylhexyl and 6-naphthylhexyl groups.

In the case where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_1$–$C_6$ alkylsulfonyl group", said group means a group in which said $C_1$–$C_6$ alkyl group is bonded to a sulfonyl moiety. Examples of said group are methanesulfonyl, ethanesulfonyl, propanesulfonyl, isopropanesulfonyl, butanesulfonyl, isobutanesulfonyl, s-butanesulfonyl, t-butanesulfonyl, pentanesulfonyl, isopentanesulfonyl, 2-methylbutanesulfonyl, neopentanesulfonyl, 1-ethylpropanesulfonyl, hexanesulfonyl, 4-methylpentanesulfonyl, 3-methylpentanesulfonyl, 2-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, 2,3-dimethylbutanesulfonyl and 2-ethylbutanesulfonyl groups. $C_1$–$C_4$ alkylsulfonyl groups are preferred, $C_1$–$C_2$ alkylsulfonyl groups are more preferred, and methanesulfonyl group is the most preferred.

In the case where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_1$–$C_6$ halogenoalkylsulfonyl group", said group means a group in which the alkyl moiety of said $C_1$–$C_6$ alkylsulfonyl group is substituted with one or more halogen atoms. Examples of said group are trifluoromethanesulfonyl, trichloromethanesulfonyl, difluoromethanesulfonyl, dichloromethanesulfonyl, dibromomethanesulfonyl, fluoromethanesulfonyl, 2,2,2-trifluoroethanesulfonyl, 2,2,2-trichloroethanesulfonyl, 2-bromoethanesulfonyl, 2-chloroethanesulfonyl, 2-fluoroethanesulfonyl, 2-iodoethanesulfonyl, 3-chloropropanesulfonyl, 4-fluorobutanesulfonyl, 6-iodohexanesulfonyl and 2,2-dibromethanesulfonyl groups.

$C_1$–$C_4$ halogenoalkylsulfonyl groups are preferred, $C_1$–$C_2$ halogenoalkylsulfonyl groups are more preferred, and trifluoromethanesulfonyl group is the most preferred.

In the case where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_6$–$C_{10}$ arylsulfonyl group (optionally having from 1–5 substituting moieties $\alpha_{1c}$, $\alpha_{1d}$ and $\alpha_{1e}$ hereafter described)", said $C_6$–$C_{10}$ arylsulfonyl group means a group in which said $C_6$–$C_{10}$ aryl group is bonded to a sulfonyl moiety. Examples of said $C_6$–$C_{10}$ arylsulfonyl group are phenylsulfonyl, indenylsulfonyl and naphthylsulfonyl groups.

In the case where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_7$–$C_{16}$ aralkylsulfonyl group (optionally having from 1–5 substituting moieties $\alpha_{1c}$, $\alpha_{1d}$ and $\alpha_{1e}$ hereafter described on the aryl moiety thereof)", said $C_7$–$C_{16}$ aralkylsulfonyl group free of the substituting moiety means a group in which said $C_7$–$C_{16}$ aralkyl is bonded to a sulfonyl moiety. Examples of said $C_7$–$C_{16}$ aralkylsulfonyl group are benzylsulfonyl, naphthylmethylsulfonyl, indenylmethylsulfonyl, 1-phenethylsulfonyl, 2-phenethylsulfonyl, 1-naphthylethylsulfonyl, 2-naphthylethylsulfonyl, 1-phenylpropylsulfonyl, 2-phenylpropylsulfonyl, 3-phenylpropylsulfonyl, 1-naphthylpropylsulfonyl, 2-naphthylpropylsulfonyl, 3-naphthylpropylsulfonyl, 1-phenylbutylsulfonyl, 2-phenylbutylsulfonyl, 3-phenylbutylsulfonyl, 4-phenylbutylsulfonyl, 1-naphthylbutylsulfonyl, 2-naphthylbutylsulfonyl, 3-naphthylbutylsulfonyl, 4-naphthylbutylsulfonyl, 5-phenylpentylsulfonyl, 5-naphthylpentylsulfonyl, 6-phenylhexylsulfonyl and 6-naphthylhexylsulfonyl groups.

In the case where $W_{1c}$, $W_{1d}$, $W_{1e}$, $W_{2c}$, $W_{2d}$ and $W_{2e}$ represent a "$C_1$–$C_8$ alkylene group", said group means a straight- or branched-chain alkylene group containing 1 to 8 carbon atoms. Examples of said group are methylene, methylmethylene, ethylene, propylene, trimethylene, 1-methylethylene, tetramethylene, 1-methyltrimethylene, 2-methyltrimethylene, 3-methyltrimethylene, 1-methylpropylene, 1,1-dimethylethylene, pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, hexamethylene, 1-methylpentamethylene, 2-methylpentamethylene, 3-methylpentamethylene, 4-methylpentamethylene, 5-methylpentamethylene, 1,1-dimethyltetramethylene, 2,2-dimethyltetramethylene, 3,3-dimethyltetramethylene, 4,4-dimethyltetramethylene, heptamethylene, 1-methylhexamethylene, 2-methylhexamethylene, 5-methylhexamethylene, 3-ethylpentamethylene, octamethylene, 2-methylheptamethylene, 5-methylheptamethylene, 2-ethylhexamethylene, 2-ethyl-3-methylpentamethylene and 3-ethyl-2-methylpentamethylene groups. Straight-chain type $C_1$–$C_6$ alkylene groups are preferred, straight-chain type $C_1$–$C_4$ alkylene groups are more preferred, and straight-chain type $C_1$–$C_2$ alkylene groups are the most preferred.

In the case where $X_c$, $X_d$, $X_e$, $\alpha_{1c}$, $\alpha_{1d}$, $\alpha_{1e}$, $\gamma_{1c}$, $\gamma_{1d}$ and $\gamma_{1e}$ represent a "$C_1$–$C_6$ halogenoalkyl group", said group means a group in which said $C_1$–$C_6$ alkyl group is substituted with one or more halogen atoms. Examples of said group are trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl and 2,2-dibromethyl groups. $C_1$–$C_4$ halogenoalkyl groups are preferred, $C_1$–$C_2$ halogenoalkyl groups are more preferred, and trifluoromethyl group is the most preferred.

In the case where $X_c$, $X_d$, $X_e$, $Z_{1c}$, $Z_{1d}$, $Z_{1e}$, $\alpha_{1c}$, $\alpha_{1d}$ and $\alpha_{1e}$ represent a "$C_1$–$C_6$ alkoxy group", said group means a group in which said $C_1$–$C_6$ alkyl group is bonded to an oxygen atom. Examples of said group are methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups. $C_1$–$C_4$ alkoxy groups are preferred, $C_1$–$C_2$ alkoxy groups are more preferred, and methoxy group is the most preferred.

In the case where $X_c$, $X_d$, $X_e$, $Z_{1c}$, $Z_{1d}$, $Z_{1e}$, $\alpha_{1c}$, $\alpha_{1d}$, $\alpha_{1e}$, $\beta_{1c}$, $\beta_{1d}$, $\beta_{1e}$, $\gamma_{1c}$, $\gamma_{1d}$ and $\gamma_{1e}$ represent a "halogen atom", said group means illustratively a fluorine atom, chlorine atom, bromine atom or iodine atom. Fluorine atom, chlorine atom and bromine atom are preferred, and fluorine atom and chlorine atom are more preferred.

In the case where $X_c$, $X_d$, $X_e$, $Z_{3c}$, $Z_{3d}$, $Z_{3e}$, $\alpha_{1c}$, $\alpha_{1d}$, $\alpha_{1e}$, $\alpha_{2c}$, $\alpha_{2d}$ and $\alpha_{2e}$ represent a "$C_3$–$C_{10}$ cycloalkyl group", said group means a 3 to 10-membered saturated cyclic hydrocarbon. Examples of said group are cyclopropyl, cyclobutyl, cyclopentyl, cyclohexyl, cycloheptyl, norbornyl and adamantyl groups. Cyclopropyl, cyclohexyl and adamantyl groups are preferred, and adamantyl group is more preferred.

In the case where $X_c$, $X_d$, $X_e$, $\alpha_{1c}$, $\alpha_{1d}$, $\alpha_{1e}$, $\alpha_{2c}$, $\alpha_{2d}$, $\alpha_{2e}$, $\beta_{1c}$, $\beta_{1d}$ and $\beta_{1e}$ represent a "$C_1$–$C_7$ aliphatic acyl group", said group involves illustratively formyl, acetyl, propionyl, butyryl, isobutyryl, valeryl, isovaleryl, pivaloyl, hexanoyl, acryloyl, methacryloyl and crotonoyl groups. $C_1$–$C_5$ aliphatic acyl groups are preferred, $C_1$–$C_3$ aliphatic acyl groups are more preferred, and acetyl group is the most preferred.

In the case where $X_c$, $X_d$, $X_e$, $\alpha_{1c}$, $\alpha_{1d}$, $\alpha_{1e}$, $\alpha_{2c}$, $\alpha_{2d}$, $\alpha_{2e}$, $\beta_{1c}$, $\beta_{1d}$ and $\beta_{1e}$ represent a "$C_4$–$C_{11}$ cycloalkylcarbonyl group", said group means a group in which said $C_3$–$C_{10}$ cycloalkyl group is bonded to a carbonyl group. Examples of said group are cyclopropylcarbonyl, cyclobutylcarbonyl, cyclopentylcarbonyl, cyclohexylcarbonyl, cycloheptylcarbonyl, norbornylcarbonyl and adamantylcarbonyl groups. $C_4$–$C_7$ cycloalkylcarbonyl groups are preferred.

In the case where $X_c$, $X_d$, $X_e$, $Z_{2c}$, $Z_{2d}$, $Z_{2e}$, $\alpha_{1c}$, $\alpha_{1d}$, $\alpha_{1e}$, $\alpha_{2c}$, $\alpha_{2d}$ and $\alpha_{2e}$ represent a "$C_7$–$C_{11}$ arylcarbonyl, group (optionally having from 1–5 substituting moieties $\beta_{1c}$, $\beta_{1d}$ and $\beta_{1e}$ hereafter described)", and in the case where $\beta_{1c}$, $\beta_{1d}$ and $\beta_{1e}$ represent a "$C_7$–$C_{11}$ arylcarbonyl group (optionally having from 1–5 substituting moieties $\gamma_{1c}$, $\gamma_{1d}$ and $\gamma_{1e}$ hereafter described)", said $C_7$–$C_{11}$ arylcarbonyl group means a group in which said $C_6$–$C_{10}$ aryl group is bonded to a carbonyl group. Examples of said $C_7$–$C_{11}$ arylcarbonyl group are benzoyl, 1-indanecarbonyl, 2-indanecarbonyl and 1- or 2-naphthoyl groups.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_8$–$C_{17}$ aralkylcarbonyl group (optionally having from 1–5 substituting moieties $\beta_{1c}$, $\beta_{1d}$ and $\beta_{1e}$ hereafter described on the aryl moiety thereof)" and in the case where $\beta_{1c}$, $\beta_{1d}$ and $\beta_{1e}$ represent "$C_8$–$C_{17}$ aralkylcarbonyl group (optionally having from 1–5 substituting moieties $\gamma_{1c}$, $\gamma_{1d}$ and $\gamma_{1e}$ hereafter described on the aryl moiety thereof)", said $C_8$–$C_{17}$ aralkylcarbonyl group means a group in which said $C_7$–$C_{16}$ aralkyl group is bonded to a carbonyl group. Examples of said $C_8$–$C_{17}$ aralkylcarbonyl group are phenylacetyl, 3-phenylpropionyl, 4-phenylbutyryl, 5-phenylpentanoyl, 6-phenylhexanoyl, naphthylacetyl, 4-naphthylbutyryl and 6-naphthylhexanoyl groups.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "monocyclic type heteroaromatic ring-carbonyl group (optionally having from 1–5 substituting moieties $\beta_{1c}$, $\beta_{1d}$ and $\beta_{1e}$ hereafter described)" and in the case where $\beta_{1c}$, $\beta_{1d}$ and $\beta_{1e}$ represent a "monocyclic type heteroaromatic ring-carbonyl group (optionally having from 1–5 substituting moieties $\gamma_{1c}$, $\gamma_{1d}$ and $\gamma_{1e}$ hereafter described)", said monocyclic type heteroaromatic ring-carbonyl group means a group in which a 5–7 membered heteroaromatic ring containing 1–3 heteroatoms selected from the group consisting of oxygen, nitrogen and sulfur atoms is bonded to a carbonyl group. Examples of said monocyclic type heteroaromatic ring-carbonyl group are 5-membered heteroaromatic ring-carbonyl groups such as furylcarbonyl, thienylcarbonyl, pyrrolylcarbonyl, pyrazolylcarbonyl, imidazolylcarbonyl, oxazolylcarbonyl, isoxazolylcarbonyl, thiazolylcarbonyl, isothiazolylcarbonyl, 1,2,3-oxadiazolylcarbonyl, triazolylcarbonyl, thiadiazolylcarbonyl, and the like; 6-membered heteroaromatic ring-carbonyl groups such as pyranylcarbonyl, nicotinoyl, isonicotinoyl, pyridazinylcarbonyl, pyrimidinylcarbonyl, pyrazinylcarbonyl, and the like; and 7-membered heteroaromatic ring-carbonyl groups such as azepinylcarbonyl, etc.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_7$–$C_{11}$ arylaminocarbonyl group (optionally having from 1–5 substituting moieties $\beta_{1c}$, $\beta_{1d}$ and $\beta_{1e}$ hereafter described on the aryl moiety thereof)" and in the case where $\beta_{1c}$, $\beta_{1d}$ and $\beta_{1e}$ represent a "$C_7$–$C_{11}$ arylaminocarbonyl group (optionally having from 1–5 substituting moieties $\gamma_{1c}$, $\gamma_{1d}$ and $\gamma_{1e}$ hereafter described on the aryl moiety thereof)", said $C_7$–$C_{11}$ arylaminocarbonyl group means a group in which the amino group of an aminocarbonyl group is substituted with said $C_6$–$C_{10}$ aryl group. Examples of said $C_7$–$C_{11}$ arylaminocarbonyl group are phenylaminocarbonyl, indenylaminocarbonyl and naphthylaminocarbonyl groups.

In the case where $Z_{1c}$, $Z_{1d}$ and $Z_{1e}$ represent a "$C_1$–$C_6$ alkylthio group", said $C_1$–$C_6$ alkylthio group means a group in which said $C_1$–$C_6$ alkyl group is bonded to a sulfur atom. Examples of said group are methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups. $C_1$–$C_4$ alkylthio groups are preferred, $C_1$–$C_2$ alkylthio groups are more preferred, and methylthio group is the most preferred.

In the case where $Z_{1c}$, $Z_{1d}$ and $Z_{1e}$ represent a "$C_6$–$C_{10}$ aryloxy group (optionally having from 1–5 substituting moieties $\alpha_{1c}$, $\alpha_{1d}$ and $\alpha_{1e}$ hereafter described)", said $C_6$–$C_{10}$ aryloxy group means a group in which said $C_6$–$C_{10}$ aryl group is substituted with an oxygen atom. Examples thereof are phenoxy, indenyloxy and naphthyloxy groups.

In the case where $Z_{1c}$, $Z_{1d}$ and $Z_{1e}$ represent a "$C_7$–$C_{16}$ aralkyloxy group (optionally having from 1–5 substituting moieties $\alpha_{1c}$, $\alpha_{1d}$ and $\alpha_{1e}$ hereafter described on the aryl moiety thereof)", said $C_7$–$C_{16}$ aralkyloxy group means a group in which said $C_7$–$C_{16}$ aralkyl group is substituted with an oxygen atom. Examples of said $C_7$–$C_{16}$ aralkyloxy group are benzyloxy, naphthylmethyloxy, indenylmethyloxy, 1-phenethyloxy, 2-phenethyloxy, 1-naphthylethyloxy, 2-naphthylethyloxy, 1-phenylpropyloxy, 2-phenylpropyloxy, 3-phenylpropyloxy, 1-naphthylpropyloxy, 2-naphthylpropyloxy, 3-naphthylpropyloxy, 1-phenylbutyloxy, 2-phenylbutyloxy, 3-phenylbutyloxy, 4-phenylbutyloxy, 1-naphthylbutyloxy, 2-naphthylbutyloxy, 3-naphthylbutyloxy, 4-naphthylbutyloxy, 5-phenylpentyloxy, 5-naphthylpentyloxy, 6-phenylhexyloxy and 6-naphthylhexyloxy groups.

In the case where $Z_{1c}$, $Z_{1d}$ and $Z_{1e}$ represent a "$C_3$–$C_{10}$ cycloalkyloxy group", said group means a group in which said $C_3$–$C_{10}$ cycloalkyl group is substituted with an oxygen atom. Examples of said group are cyclopropyloxy, cyclobutyloxy, cyclopentyloxy, cyclohexyloxy, cycloheptyloxy, norbornyloxy and adamantyloxy groups. $C_3$–$C_6$ cycloalkyloxy groups are preferred, and $C_5$–$C_6$ cycloalkyloxy groups are more, preferred.

In the case where $Z_{1c}$, $Z_{1d}$ and $Z_{1e}$ represent a "$C_3$–$C_{10}$ cycloalkylthio group", said group means a group in which said $C_3$–$C_{10}$ cycloalkyl group is substituted with a sulfur atom. Examples of said group are cyclopropylthio, cyclobutylthio, cyclopentylthio, cyclohexylthio, cycloheptylthio, norbornylthio and admantylthio groups. $C_3$–$C_6$ cycloalkylthio groups are preferred, and $C_5$–$C_6$ cycloalkylthio groups are more preferred.

In the case where $Z_{2c}$, $Z_{2d}$, $Z_{2e}$, $Z_{3c}$, $Z_{3d}$ and $Z_{3e}$ represent a "saturated heterocyclic ring group (optionally having from 1–5 substituting moieties $\alpha_{1c}$, $\alpha_{1d}$ and $\alpha_{1e}$ hereafter described)", said saturated heterocyclic ring group means a group in which a 4–7 membered saturated heterocyclic ring group contains at least one ring atom selected from nitrogen, oxygen and sulfur atoms. Examples of said saturated heterocyclic ring group are 4-membered saturated heterocyclic rings such as azetidyl, etc.; 5-membered saturated heterocyclic rings such as pyrrolidyl, tetrahydrofuranyl, tetrahydrothiophenyl, imidazolidyl, oxazolidyl, isoxazolidyl, thiazolidyl, isothiazolidyl, etc.; 6-membered saturated heterocyclic rings such as piperidino, tetrahydropyranyl, tetrahydrothiopyranyl, piperazino, morpholino, thiomorpholino, etc.; and 7-membered saturated heterocyclic ring groups such as homopiperazino, etc.

In the case where $Z_{1c}$, $Z_{1d}$ and $Z_{1e}$ represent a "saturated heterocyclic ring-oxy group (optionally having from 1–5 substituting moieties $\alpha_{1c}$, $\alpha_{1d}$ and $\alpha_{1e}$ hereafter described)", said saturated heterocyclic ring-oxy group means a group in which said saturated heterocyclic ring is bonded to an oxygen atom. Examples of said saturated heterocyclic ring-oxy group are 4-membered saturated heterocyclic ring-oxy groups such as azetidyloxy, etc.; 5-membered saturated heterocyclic ring-oxy groups such as pyrrolidyloxy, tetrahydrofuranyloxy, tetrahydrothiophenyloxy, imidazolidyloxy, oxazolidyloxy, isoxazolidyloxy, thiazolidyloxy, isothiazolidyloxy, etc.; 6-membered saturated heterocyclic ring-oxy groups such as piperidinoxy, tetrahydropyranyloxy, tetrahydrothiopyranyloxy, piperazinoxy, morpholinoxy, thiomorpholinoxy, etc.; and 7-membered saturated heterocyclic ring-oxy groups such as homopiperazinoxy, etc.

In the case where $Z_{1c}$, $Z_{1d}$, $Z_{1e}$, $Z_{3c}$, $Z_{3d}$ and $Z_{3e}$ represent a "monocyclic type heteroaromatic ring-oxy group (optionally having from 1–5 substituting moieties $\alpha_{1c}$, $\alpha_{1d}$ and $\alpha_{1e}$ hereafter described)" said monocyclic heteroaromatic ring-oxy group means a group in which said 5–7 membered heteroaromatic ring containing 1–3 heteroatom(s) selected from the group consisting of oxygen, nitrogen and sulfur atoms is bonded to an oxygen atom. Examples of said saturated heterocyclic ring-oxy moiety are 5-membered heteroaromatic ring-oxy groups such as furyloxy, thienyloxy, pyrrolyloxy, pyrazolyloxy, imidazolyloxy, oxazolyloxy, isoxazolyloxy, thiazolyloxy, isothiazolyloxy, 1,2,3-oxadiazolyloxy, triazolyloxy, tetrazolyloxy, thiadiazolyloxy, etc.; 6-membered heteroaromatic ring-oxy groups such as pyranyloxy, pyridyloxy, pyridazinyloxy, pyrimidinyloxy, pyrazinyloxy, etc.; and 7-membered heterocyclic ring-oxy groups such as azepinyloxy, etc.

In the case where $Z_{1c}$, $Z_{1d}$ and $Z_{1e}$ represent a "$C_6$–$C_{10}$ arylthio group (optionally having from 1–5 substituting moieties $\alpha_{1c}$, $\alpha_{1d}$ and $\alpha_{1e}$ hereafter described)", said $C_6$–$C_{10}$ arylthio moiety means a group in which said $C_6$–$C_{10}$ aryl group is substituted with a sulfur atom. Examples of said $C_6$–$C_{10}$ arylthio group are phenylthio, indenylthio and naphthylthio groups.

In the case where $Z_{1c}$, $Z_{1d}$ and $Z_{1e}$ represent a "$C_7$–$C_{16}$ aralkylthio group (optionally having from 1–5 substituting moieties $\alpha_{1c}$, $\alpha_{1d}$ and $\alpha_{1e}$ hereafter described on the aryl moiety thereof)", said $C_7$–$C_{16}$ aralkylthio group means a group in which said $C_7$–$C_{16}$ aralkyl group is substituted with a sulfur atom. Examples of said $C_7$–$C_{16}$ aralkylthio group are benzylthio, naphthylmethylthio, indenylmethylthio, 1-phenethylthio, 2-phenethylthio, 1-naphthylethylthio, 2-naphthylethylthio, 1-phenylpropylthio, 2-phenylpropylthio, 3-phenylpropylthio, 1-naphthylpropylthio, 2-naphthylpropylthio, 3-naphthylpropylthio, 1-phenylbutylthio, 2-phenylbutylthio, 3-phenylbutylthio, 4-phenylbutylthio, 1-naphthylbutylthio, 2-naphthylbutylthio, 3-naphthylbutylthio, 4-naphthylbutylthio, 5-phenylpentylthio, 5-naphthylpentylthio, 6-phenylhexylthio and 6-naphthylhexylthio groups.

In the case where $Z_{1c}$, $Z_{1d}$ and $Z_{1e}$ represent a "saturated heterocyclic ring-thio group (optionally having from 1–5 substituting moieties $\alpha_{1c}$, $\alpha_{1d}$ and $\alpha_{1e}$ hereafter described)", said saturated heterocyclic ring-thio group means a group in which said saturated heterocyclic ring is bonded to a sulfur atom. Examples of said saturated heterocyclic ring-thio group are 4-membered saturated heterocyclic ring-oxy groups such as azetidylthio, etc.; 5-membered saturated heterocyclic ring-thio groups such as pyrrolidylthio, tetrahydrofuranylthio, imidazolidylthio, oxazolidylthio, isoxazolidylthio, thiazolidylthio, isothiazolidylthio, etc.; 6-membered saturated heterocyclic ring-thio groups such as piperidinylthio, tetrahydropyranylthio, tetrahydrothiopyranylthio, piperazinylthio, morpholylthio, thiomorpholylthio, etc.; and 7-membered saturated heterocyclic ring-thio groups such as homopiperazinothio, etc.

In the case where $Z_{1c}$, $Z_{1d}$ and $Z_{1e}$ represent a "monocyclic type heteroaromatic ring-thio group (optionally having from 1–5 substituting moieties $\alpha_{1c}$, $\alpha_{1d}$ and $\alpha_{1e}$ hereafter described)", said monocyclic heteroaromatic ring-thio group means a group in which said 5–7 membered heteroaromatic ring containing 1–3 heteroatom(s) selected from the group consisting of oxygen, nitrogen and sulfur atoms is bonded to a sulfur atom. Examples of said saturated heterocyclic ring-thio group are 5-membered heteroaromatic ring-thio groups such as furylthio, thienylthio, pyrrolylthio, pyrazolylthio, imidazolylthio, oxazolylthio, isoxazolylthio, thiazolylthio, isothiazolylthio, 1,2,3-oxadiazolylthio, triazolylthio, tetrazolylthio, thiadiazolylthio, etc.; 6-membered heteroaromatic ring-thio groups such as pyranylthio, pyridylthio, pyridazinylthio, pyrimidinylthio, pyrazinylthio, etc.; and 7-membered heterocyclic ring-thio groups such as azepinylthio, etc.

In the case where the substituting moieties $\beta_{1c}$, $\beta_{1d}$ and $\beta_{1e}$ represent a "$C_1$–$C_{10}$ alkyl group", said group means a straight- or branched-chain alkyl group of 1–10 carbon atoms. In addition to those illustrated in the definition of said $C_1$–$C_6$ alkyl group, examples of said group are heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl and 7,7-dimethyloctyl groups. $C_1$–$C_6$ alkyl groups are preferred, $C_1$–$C_4$ alkyl groups are more preferred, and $C_1$–$C_2$ alkyl groups are the most preferred.

In the case where the substituting moieties $\beta_{1c}$, $\beta_{1d}$ and $\beta_{1e}$ represent a "$C_6$–$C_{10}$ aryl group (optionally having from 1–5 substituting moieties $\gamma_{1c}$, $\gamma_{1d}$ and $\gamma_{1e}$)", in view of the definition of said substituting moieties $\gamma_{1c}$, $\gamma_{1d}$ and $\gamma_{1e}$, examples of said group having the substituting moieties $\gamma_{1c}$, $\gamma_{1d}$ and $\gamma_{1e}$ are 4-methylphenyl, 4-methylnaphthyl, 3,4-dimethylphenyl, 2,3,4-trimethylphenyl, 4-propylphenyl, 4-propylnaphthyl, 2-, 3- or 4-trifluoromethylphenyl, 2-, 3- or 4-trifluoromethylnaphthyl, 3,4-ditrifluoromethylphenyl, 2,3,4-tritrifluoromethylphenyl, 4-tetrafluoropropylphenyl, 4-tetrafluoropropylnaphthyl, 4-fluorophenyl, 4-fluoronaphthyl, 3,4-difluorophenyl, 2,3,4-trifluorophenyl, 4-hydroxyphenyl, 4-hydroxynaphthyl, 3,4-dihydroxyphenyl and 2,3,4-trihydroxyphenyl groups. As to said group, $C_6$–$C_{10}$ aryl groups (optionally having from 1–3 substituting moieties $\gamma_{1c}$, $\gamma_{1d}$ and $\gamma_{1e}$) are preferred, phenyl groups (optionally having from 1–3 substituting moieties $\gamma_{1c}$, $\gamma_{1d}$ and $\gamma_{1e}$) are more preferred, and phenyl and 4-trifluoromethylphenyl groups are the most preferred.

In the case where the substituting moieties $\beta_{1c}$, $\beta_{1d}$ and $\beta_{1e}$ represent a "$C_7$–$C_{16}$ aralkyl group (optionally having from 1–5 substituting moieties $\gamma_{1c}$, $\gamma_{1d}$ and $\gamma_{1e}$ on the aryl moiety thereof)", examples of said group having such a substituting moiety are 4-methylbenzyl, 2,3,4-trimethylbenzyl, 4-methylphenethyl, 2,3,4-trimethylphenethyl, 4-(4-methylphenyl)butyl, 2-, 3- or 4-trifluoromethylbenzyl, 3,4-ditrifluoromethylbenzyl, 2,3,4-tritrifluoromethylbenzyl, 4-tetrafluoropropylbenzyl, 4-trifluoromethylphenethyl, 3,4-ditrifluoromethylphenethyl, 2,3,4-tritrifluoromethylphenethyl, 4-tetrafluoropropylphenethyl, 4-(4-trifluoromethylphenyl)butyl, 4-(4-tetrafluoropropyl)butyl, 6-(4-trifluoromethylphenyl)hexyl, 6-(4-tetrafluoropropylphenyl)hexyl, 2-, 3- or 4-trifluoromethylnaphthylmethyl, 4-tetrafluoropropylnaphthylmethyl, 4-(4-trifluoromethylnaphthyl)butyl, 4-(4-tetrafluoropropylnaphthyl)butyl, 4-fluorobenzyl, 2,3,4-trifluorobenzyl, 4-fluorophenethyl, 2,3,4-trifluorophenethyl, 4-(4-fluorophenyl)butyl, 4-hydroxy-benzyl, 2,3,4-trihydroxybenzyl, 4-hydroxyphenethyl, 2,3,4-trihydroxyphenethyl and 4-(4-hydroxyphenyl)butyl groups. As to said group, $C_7$–$C_{16}$ aralkyl groups (optionally having from 1–3 substituting moieties $\gamma_{1c}$, $\gamma_{1d}$ and $\gamma_{1e}$ on the aryl moiety thereof) are preferred, phenyl-$C_1$–$C_6$ alkyl groups (optionally having from 1–3 substituting moieties $\gamma_{1c}$, $\gamma_{1d}$ and $\gamma_{1e}$ on the phenyl moiety) are more preferred, further phenyl-$C_1$–$C_6$ alkyl groups (optionally having one trifluoromethyl group on the phenyl moiety) are yet more preferred, and phenyl-$C_1$–$C_2$ alkyl groups (optionally having one trifluoromethyl group on the phenyl moiety) are the most preferred.

In the case where the substituting moieties $\beta_{1c}$, $\beta_{1d}$ and $\beta_{1e}$ represent a "$C_7$–$C_{11}$ arylcarbonyl group (optionally having from 1–5 substituting moieties $\gamma_{1c}$, $\gamma_{1d}$ and $\gamma_{1e}$)", examples of said group having such a substituting moiety are 4-methylbenzoyl, 1- or 2-(5-methyl)naphthoyl, 4-trifluoromethylbenzoyl, 4-tetrafluoropropylbenzoyl, 1-(5-trifluoromethylindane)carbonyl, 2-(5-trifluoromethylindane)carbonyl, 2-(6-trifluoromethylindane)carbonyl, 1- or 2-(5- trifluoromethyl)naphthoyl, 4-fluorobenzoyl, 1- or 2-(5-fluoro)naphthoyl, 4-hydroxybenzoyl and 1- or 2-(5-hydroxy)naphthoyl groups. As to said group, $C_7$–$C_{11}$ arylcarbonyl groups (optionally having from 1–3 substituting moieties $\gamma_{1c}$, $\gamma_{1d}$ and $\gamma_{1e}$) are preferred, benzoyl groups (optionally having from 1–3 substituting moieties $\gamma_{1c}$, $\gamma_{1d}$ and $\gamma_{1e}$) are more preferred, further benzoyl groups (optionally having one substituting moiety $\gamma_{1c}$, $\gamma_{1d}$ or $\gamma_{1e}$) are yet more preferred, and benzoyl groups (optionally having one substituting moiety, trifluoromethyl) are the most preferred.

In the case where the substituting moieties $\beta_{1c}$, $\beta_{1d}$ and $\beta_{1e}$ represent a "$C_8$–$C_{17}$ aralkylcarbonyl group (optionally having from 1–5 substituting moieties $\gamma_{1c}$, $\gamma_{1d}$ and $\gamma_{1e}$ on the aryl moiety thereof", examples of said group having such a substituting moiety are 4-methylphenylacetyl, 4-(4-methyl) phenylbutyryl, 6-(methylnaphthyl)hexanoyl, 2-, 3- or 4-trifluoromethylphenylacetyl, 4-tetrafluoropropylphenylacetyl, 4-(4-trifluoromethyl)phenylbutyryl, 6-(4-trifluoromethyl) phenylhexanoyl, 4-trifluoromethylnaphthylacetyl, 6-(trifluoromethylnaphthyl)hexanoyl, 4-fluorophenylacetyl, 4-(4-fluoro)phenylbutyryl, 6-(fluoronaphthyl)hexanoyl, 4-hydroxyphenylacetyl, 4-(4-hydroxy)phenylbutyryl and 6-(hydroxynaphthyl)hexanoyl groups. As to said group, $C_8$–$C_{17}$ aralkylcarbonyl groups (optionally having from 1–3 substituting moieties $\gamma_{1c}$, $\gamma_{1d}$ or $\gamma_{1e}$ on the aryl moiety) are preferred, phenyl-$C_1$–$C_6$ alkylcarbonyl groups (optionally having from 1–3 substituting moieties $\gamma_{1c}$, $\gamma_{1d}$ and $\gamma_{1e}$ on the aryl moiety) are more preferred, further phenyl-$C_1$–$C_6$ alkylcarbonyl groups (optionally having one substituting moiety, $C_1$–$C_6$ halogenoalkyl, on the aryl moiety) are still more preferred, furthermore phenyl-$C_1$–$C_6$ alkylcarbonyl groups (optionally having one substituting moiety, trifluoromethyl, on the aryl moiety) are yet more preferred, and phenylacetyl and 4-trifluoromethylphenylacetyl groups are the most preferred.

In the case where the substituting moieties $\beta_{1c}$, $\beta_{1d}$ and $\beta_{1e}$ represent a "monocyclic type heteroaromatic ring-carbonyl group (optionally having from 1–5 substituting moieties $\gamma_{1c}$, $\gamma_{1d}$ and $\gamma_{1e}$)", examples of the group having such a substituting moiety are methylfurylcarbonyl, methylthienylcarbonyl, methylpyrrolylcarbonyl, methylnicotinoyl, trifluoromethylfurylcarbonyl, trifluoromethylthienylcarbonyl, trifluoromethylpyrrolylcarbonyl, trifluoromethyloxazolylcarbonyl, trifluoromethylthiazolylcarbonyl, trifluoromethylnicotinoyl, tetrafluoropropylfurylcarbonyl, tetrafluoropropylthienylcarbonyl, tetrafluoropropylpyrrolylcarbonyl, fluorofurylcarbonyl, fluorothienylcarbonyl, fluoropyrrolylcarbonyl, fluoronicotinoyl, hydroxyfurylcarbonyl, hydroxythienylcarbonyl, hydroxypyrrolylcarbonyl and hydroxynicotinoyl groups. As to said group, monocyclic type heteroaromatic ring-carbonyl groups (optionally having from 1–3 substituting moieties $\gamma_{1c}$, $\gamma_{1d}$ and $\gamma_{1e}$) are preferred, monocyclic type heteroaromatic ring-carbonyl groups (optionally having one substituting moiety $\gamma_{1c}$, $\gamma_{1d}$ or $\gamma_{1e}$) are more preferred, further monocyclic type heteroaromatic ring-carbonyl groups (optionally having one substituting moiety, trifluoromethyl) are still more preferred, furthermore 5- or 6-member monocyclic type heteroaromatic ring-carbonyl groups (optionally having one substituting moiety, trifluoromethyl) are yet more preferred, and furylcarbonyl, thienylcarbonyl, pyrrolylcarbonyl and nicotinoyl groups are the most preferred.

In the case where the substituting moieties $\beta_{1c}$, $\beta_{1d}$ and $\beta_{1e}$ represent a "$C_7$–$C_{11}$ arylaminocarbonyl group (optionally having from 1–5 substituting moieties $\gamma_{1c}$, $\gamma_{1d}$ and $\gamma_{1e}$ on the aryl moiety thereof)", examples of said group having such a substituting moiety are 4-methylphenylcarbamoyl, 2,3,4-trimethylphenylcarbamoyl, 1- or 2-(6- or 7-methylnaphthyl)carbamoyl, 2-, 3- or 4-trifluoromethylphenylcarbamoyl, 4-tetrafluoropropylphenylcarbamoyl, 3,4-difluoromethylphenylcarbamoyl, 2,3,4-tritrifluoromethylphenylcarbamoyl, 1- or 2-(6- or 7-trifluoromethylnaphthyl)carbamoyl, 2-(6-tetrafluoropropylnaphthyl)carabamoyl, 4-fluorophenylcarbamoyl, 2,3,4-trifluorophenylcarbamoyl, 1- or 2-(6- or 7-fluoronaphthyl) carbamoyl, 4-hydroxyphenylcarbamoyl, 2,3,4-trihydroxyphenylcarbamoyl and 1- or 2-(6- or 7-hydroxynaphthyl)carbamoyl groups. As to said group, $C_7$–$C_{11}$ arylaminocarbonyl groups (optionally having from 1–3 substituting moieties $\gamma_{1c}$, $\gamma_{1d}$ and $\gamma_{1e}$ on the aryl moiety) are preferred, phenylaminocarbonyl groups (optionally having from 1–3 substituting moieties $\gamma_{1c}$, $\gamma_{1d}$ and $\gamma_{1e}$ on the phenyl moiety) are more preferred, further phenylaminocarbonyl groups (optionally having from 1–3 $C_1$–$C_6$ halogenoalkyl groups as the substituting moieties $\gamma_{1c}$, $\gamma_{1d}$ and $\gamma_{1e}$ on the phenyl moiety) are more preferred, and furthermore phenylaminocarbonyl groups (optionally having one trifluoromethyl group as the substituting moiety) are the most preferred.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{1e}$ represent a "$C_6$–$C_{10}$ aryl group (optionally having from 1–5 substituting moieties $\beta_{1c}$, $\beta_{1d}$ and $\beta_{1e}$)", in view of the definition of said $\beta_{1c}$, $\beta_{1d}$ and $\beta_{1e}$, examples of said group having such a substituting moiety are methylphenyl, acetylphenyl, benzoylphenyl, biphenylyl, methylbiphenylyl, methylnaphthyl, acetylnaphthyl and benzoylnaphthyl groups. As to said group, $C_6$–$C_{10}$ aryl groups (optionally having from 1–3 substituting moieties $\beta_{1c}$, $\beta_{1d}$ and $\beta_{1e}$) are preferred, phenyl groups (optionally having from 1–3 substituting moieties $\beta_{1c}$, $\beta_{1d}$ and $\beta_{1e}$) are more preferred, further phenyl groups (optionally having one or two substituting moieties $\beta_{1c}$, $\beta_{1d}$ and $\beta_{1e}$) are yet more preferred, and furthermore phenyl groups (optionally having one substituting moiety $\beta_{1c}$, $\beta_{1d}$ or $\beta_{1e}$) are the most preferred.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_7$–$C_{16}$ aralkyl group (optionally having from 1–5 substituting moieties $\beta_{1c}$, $\beta_{1d}$ and $\beta_{1e}$ on the aryl moiety)", examples of said group having such a substituting moiety are methylbenzyl, acetylbenzyl, benzoylbenzyl, biphenylylmethyl, methylbiphenylylmethyl, methylnaphthylmethyl, acetylnaphthylmethyl, benzoylnaphthylmethyl, methylphenethyl, acetylphenethyl, methylnaphthylethyl, acetylnaphthylethyl, methylphenylbutyl, acetylphenylbutyl, methylnaphthylbutyl and acetylnaphthylbutyl groups. As to said group, $C_7$–$C_{16}$ aralkyl groups (optionally having from 1–3 substituting moieties $\beta_{1c}$, $\beta_{1d}$ and $\beta_{1e}$ on the aryl moiety) are preferred, phenyl-$C_1$–$C_6$ alkyl groups (optionally having from 1–3 substituting moieties $\beta_{1c}$, $\beta_{1d}$ and $\beta_{1e}$ on the phenyl moiety) are more preferred, further phenyl-$C_1$–$C_4$ alkyl groups (optionally having one or two substituting moieties $\beta_{1c}$, $\beta_{1d}$ and $\beta_{1e}$ on the phenyl moiety) are yet more preferred, and furthermore benzyl or phenethyl groups (optionally having one substituting moiety $\beta_{1c}$, $\beta_{1d}$ or $\beta_{1e}$) are the most preferred.

In the case where $X_c$, $X_d$, $X_e$, $\alpha_{1c}$, $\alpha_{1d}$, $\alpha_{2c}$, $\alpha_{2d}$ and $\alpha_{2e}$ represent a "$C_7$–$C_{11}$ arylcarbonyl group (optionally having from 1–5 substituting moieties $\beta_{1c}$, $\beta_{1d}$ or $\beta_{1e}$)", examples of said group having such a substituting moiety are methylbenzoyl, biphenylylcarbonyl, acetylbenzoyl, carbamoylbenzoyl, 4-trifluoromethylphenylcarbamoylbenzoyl and trifluoronaphthylcarbonyl groups. As to said group, $C_7$–$C_{11}$ arylcarbonyl groups (optionally having from 1–3 substituting moieties $\beta_{1c}$, $\beta_{1d}$ and $\beta_{1e}$) are preferred, benzoyl groups (optionally having from 1–3 substituting moieties $\beta_{1c}$, $\beta_{1d}$ and $\beta_{1e}$) are more preferred, further benzoyl groups (optionally having one or two substituting moieties $\beta_{1c}$, $\beta_{1d}$ and $\beta_{1e}$) are yet more preferred, and furthermore benzoyl groups (optionally having one substituting moiety $\beta_{1c}$, $\beta_{1d}$ or $\beta_{1e}$) are the most preferred.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_8$–$C_{17}$ aralkylcarbonyl group (optionally having from 1–5 substituting moieties $\beta_{1c}$, $\beta_{1d}$ and $\beta_{1e}$ on the aryl moiety thereof), examples of said group having such a substituting moiety are methylphenylacetyl, acetylphenylacetyl, benzoylphenylacetyl, biphenylylacetyl, carbamoylphenylacetyl, (4-trifluoromethylphenylcarbamoyl)phenylacetyl, 4-(methylphenyl)butyryl, 4-[(4-trifluoromethylphenylcarbamoyl)phenyl]butyryl, methylnaphthylacetyl and carbamoylnaphthylacetyl groups. As to said group, $C_8$–$C_{17}$ aralkylcarbonyl groups (optionally having from 1–3 substituting moieties $\beta_{1c}$, $\beta_{1d}$ and $\beta_{1e}$ on the aryl moiety) are preferred, phenyl-$C_2$–$C_7$ alkylcarbonyl groups (optionally having from 1–3 substituting moieties $\beta_{1c}$, $\beta_{1d}$ and $\beta_{1e}$ on the phenyl moiety) are more preferred, further phenyl-$C_2$–$C_7$ alkylcarbonyl groups (optionally having one substituting moiety $\beta_{1c}$, $\beta_{1d}$ or $\beta_{1e}$ on the phenyl moiety) are yet more preferred, and furthermore phenylacetyl groups (optionally having one substituting moiety $\beta_{1c}$, $\beta_{1d}$ or $\beta_{1e}$ on the phenyl moiety) are the most preferred.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "monocyclic type heteroaromatic ring-carbonyl group (optionally having from 1–5 substituting moieties $\beta_{1c}$, $\beta_{1d}$ and $\beta_{1e}$ hereafter described)", examples of said group are methylfurylcarbonyl, methylthienylcarbonyl, methylpyrrolylcarbonyl, methyloxazolylcarbonyl, methylthiazolylcarbonyl, methyltriazolylcarbonyl, methylpyranylcarbonyl, methylnicotinoyl, methylpyridazinylcarbonyl, methylpyrimidinylcarbonyl, acetylfurylcarbonyl, acetylthienylcarbonyl, acetylpyrrolylcarbonyl, acetyloxazolylcarbonyl, acetylthiazolylcarbonyl, acetylnicotinoyl, carbamoylfurylcarbonyl, carbamoylthienylcarbonyl, carbamoylpyrrolylcarbonyl, carbamoyloxazolylcarbonyl, carbamoylthiazolylcarbonyl and carbamoylnicotinoyl groups. As to said group, monocyclic type heteroaromatic ring-carbonyl groups (optionally having from 1–3 substituting moieties $\beta_{1c}$, $\beta_{1d}$ and $\beta_{1e}$) are preferred, further monocyclic type heteroaromatic ring-carbonyl groups (optionally having one or two substituting moieties $\beta_{1c}$, $\beta_{1d}$ and $\beta_{1e}$) are more preferred, furthermore 5- or 6-membered monocyclic type heteroaromatic ring-carbonyl groups (optionally having one or two substituting moieties $\beta_{1c}$, $\beta_{1d}$ and $\beta_{1e}$) are yet more preferred, and 5- or 6-membered monocyclic type heteroaromatic ring-carbonyl groups (optionally having one substituting moiety $\beta_{1c}$, $\beta_{1d}$ or $\beta_{1e}$) are the most preferred.

In the case where $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ represent a "$C_7$–$C_{11}$ arylaminocarbonyl group (optionally having from 1–5 substituting moieties $\beta_{1c}$, $\beta_{1d}$ and $\beta_{1e}$ hereafter described on the aryl moiety thereof)", examples of said group having such a substituting moiety are methylphenylcarbonyl, biphenylylcarbamoyl, acetylphenylcarbamoyl, methylnaphthylcarbamoyl and acetylnaphthylcarbamoyl groups. As to said group, $C_7$–$C_{11}$ arylaminocarbonyl groups (optionally having from 1–3 substituting moieties $\beta_{1c}$, $\beta_{1d}$ and $\beta_{1e}$ on the aryl moiety) are preferred, further phenylaminocarbonyl groups (optionally having from 1–3 substituting moieties $\beta_{1c}$, $\beta_{1d}$ and $\beta_{1e}$ on the phenyl moiety) are more preferred, and phenylaminocarbonyl groups (optionally having one substituting moiety $\beta_{1c}$, $\beta_{1d}$ or $\beta_{1e}$ on the phenyl moiety) are the most preferred.

In the case where $X_c$, $X_d$, $X_e$, $\alpha_{1c}$, $\alpha_{1d}$ and $\alpha_{1e}$ represent an "amino group optionally having one or two substituting moieties $\beta_{1c}$, $\beta_{1d}$ and $\beta_{1e}$", examples of said group are amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylamino, 1- or 2-indenylamino, 1- or 2-naphthylamino, benzylamino, 1- or 2-naphthylmethylamino, 1-indenylmethylamino, 1- or 2-phenethylamino, 1-, 2- or 3-phenylpropylamino, 4-phenylbutylamino, 1-phenylbutylamino, 5-phenylpentylamino, 6-phenylhexylamino, dibenzylamino, formylamino, acetylamino, propionylamino, butyrylamino, isobutyrylamino, valerylamino, isovalerylamino, pivaloylamino, hexanoylamino, acryloylamino, methacryloylamino, crotonoylamino, benzoylamino, 1-indanecarbonylamino, 1- or 2-naphthoylamino, phenylacetylamino, 3-phenylpropionylamino, 4-phenylbutyrylamino, 5-phenylpentanoylamino, 6-phenylhexanoylamino, cyclopropionylamino, cyclobutyrylamino, cyclopentanoylamino, cyclohexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonylamino, pyrimidinylcarbonylamino, pyridazinylcarbonylamino, thiazolylcarbonylamino, oxazolylcarbonylamino, oxadiazolylcarbonylamino, thiadiazolylcarbonylamino, N,N-diacetylamino, N-formyl-N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-hexyl-N-1-naphthoylamino, N-hexyl-N-2-naphthoylamino, N-hexyl-N-phenylacetylamino, N-isobutyl-N-cycloheptanoylamino, N-butyl-N-nicotinoylamino, N-hexyl-N-nicotinoylamino, N-isonicotinoyl-N-hexylamino and 4-trifluoromethylphenylcarbamoylamino groups. As to said group, amino groups optionally having one or two substituting moieties selected from $C_1$–$C_{10}$ alkyl, $C_1$–$C_7$ aliphatic acyl and phenylaminocarbonyl group (optionally having from 1–3 substituting moieties $\gamma_{1c}$, $\gamma_{1d}$ and $\gamma_{1e}$ on the phenyl moiety) are preferred, further amino groups optionally having one or two substituting moieties selected from $C_1$–$C_6$ alkyl, $C_1$–$C_2$ aliphatic acyl and phenylaminocarbonyl group (optionally having one substituting moiety $\gamma_{1c}$, $\gamma_{1d}$ or $\gamma_{1e}$ on the phenyl moiety) are more preferred, and furthermore amino groups optionally substituted with one phenylaminocarbonyl groups (optionally having one substituting moiety $\gamma_{1c}$, $\gamma_{1d}$ or $\gamma_{1e}$ on the phenyl moiety) are the most preferred.

In the case where $R_{1c}$, $R_{1d}$, $R_{1e}$, $R_{2c}$, $R_{2d}$, $R_{2e}$, $R_{3c}$, $R_{3d}$, $R_{3e}$, $Z_{1c}$, $Z_{1d}$, $Z_{1e}$, $Z_{3c}$, $Z_{3d}$ and $Z_{3e}$ represent a "$C_6$–$C_{10}$ aryl group (optionally having from 1–5 substituting moieties $\alpha_{1c}$, $\alpha_{1d}$ and $\alpha_{1e}$)", in view of the definition of $X_c$, $X_d$, $X_e$, $\alpha_{1c}$, $\alpha_{1d}$, $\alpha_{1e}$, $\alpha_{2c}$, $\alpha_{2d}$ and $\alpha_{2e}$ described above, examples of said group having such a substituting moiety are methylphenyl, trifluoromethylphenyl, hydroxyphenyl, 4-hydroxy-2,3,5-trimethylphenyl, 3,5-di-t-butyl-4-hydroxyphenyl, adamantylphenyl, 4-amino-3,5-dimethylphenyl, acetylphenyl, methoxyphenyl, benzoylphenyl, fluorophenyl, difluorophenyl, chlorophenyl, dichlorophenyl, bromophenyl, nitrophenyl, (dimethylamino)phenyl, biphenylyl, methylbiphenylyl, methylnaphthyl, trifluoronaphthyl, hydroxynaphthyl, methoxynaphthyl, fluoronaphthyl and chloronaphthyl groups. As to said group, $C_6$–$C_{10}$ aryl groups (optionally having from 1–3 substituting moieties $\alpha_{1c}$, $\alpha_{1d}$ and $\alpha_{1e}$) are preferred, further phenyl groups (optionally having from 1–3 substituting moieties $\alpha_{1c}$, $\alpha_{1d}$ and $\alpha_{1e}$) are more preferred, furthermore phenyl groups (optionally having one or two substituting moieties $\alpha_{1c}$, $\alpha_{1d}$ and $\alpha_{1e}$) are yet more preferred, and phenyl groups (optionally having one substituting moiety $\alpha_{1c}$, $\alpha_{1d}$ or $\alpha_{1e}$) are the most preferred.

In the case where $Z_{2c}$, $Z_{2d}$ and $Z_{2e}$ represent a "$C_6$–$C_{10}$ aryl group (optionally having from 1–5 substituting moieties $\alpha_{1c}$, $\alpha_{1d}$ and $\alpha_{1e}$)", examples of said group are adamantylphenyl, biphenylyl, methylbiphenylyl, benzylphenyl, acetylphenyl, cyclohexylcarbonylphenyl, benzoylphenyl, benzylcarbonylphenyl, pyridinecarbonylphenyl and phenylaminocarbonyl groups. As to said group, $C_6$–$C_{10}$ aryl groups (optionally having from 1–3 substituting moieties $\alpha_{1c}$, $\alpha_{2d}$ and $\beta_{2e}$) are preferred, further phenyl groups (optionally having from 1–3 substituting moieties $\alpha_{2e}$, $\alpha_{2d}$ and $\alpha_{2e}$) are more preferred, furthermore phenyl groups (optionally having one or two substituting moieties $\alpha_{2c}$, $\alpha_{2d}$ and $\alpha_{2e}$) are yet more preferred, and phenyl groups (optionally having one substituting moiety $\alpha_{2c}$, $\alpha_{2d}$ or $\alpha_{2e}$) are the most preferred.

In the case where $R_{1c}$, $R_{1d}$, $R_{1e}$, $R_{2c}$, $R_{2d}$, $R_{2e}$, $R_{3c}$, $R_{3d}$, $R_{3e}$, $Z_{1c}$, $Z_{1d}$, $Z_{1e}$, $Z_{3c}$, $Z_{3d}$ and $Z_{3e}$ represent a "$C_7$–$C_{16}$ aralkyl group (optionally having from 1–5 substituting moieties $\alpha_{1c}$, $\alpha_{1d}$ and $\alpha_{1e}$ on the aryl moiety thereof)", examples of said group having such a substituting moiety are methylbenzyl, trifluoromethylbenzyl, hydroxybenzyl, 4-hydroxy-2,3,5-trimethylbenzyl, 3,5-di-t-butyl-4-hydroxybenzyl, adamantylbenzyl, 4-amino-3,5-dimethylbenzyl, acetylbenzyl, methoxybenzyl, benzoylbenzyl, fluorobenzyl, difluorobenzyl, chlorobenzyl, dichlorobenzyl, nitrobenzyl, (dimethylamino)benzyl, biphenylylmethyl, methylbiphenylylmethyl, methylphenethyl, trifluoromethylphenethyl, hydroxyphenethyl, 4-hydroxy-2,3,5-trimethylphenethyl, 3,5-di-t-butyl-4-hydroxyphenethyl, adamantylphenethyl, 4-amino-3,5-dimethylphenethyl, acetylphenethyl, methoxyphenethyl, benzoylphenethyl, fluorophenethyl, difluorophenethyl, chlorophenethyl, nitrophenethyl, (dimethylamino)phenethyl, biphenylylethyl, methylbiphenylyl, methylphenylbutyl, trifluoromethylphenylbutyl, hydroxyphenylbutyl, 4-hydroxy-2,3,5-trimethylphenylbutyl, 3,5-di-t-butyl-4-hydroxyphenylbutyl, adamantylphenylbutyl, 4-amino-3,5-dimethylphenylbutyl, acetylphenylbutyl, methoxyphenylbutyl, fluorophenylbutyl, chlorophenylbutyl, nitrophenylbutyl, (dimethyl)phenylbutyl, biphenylylbutyl, methylnaphthylmethyl, trifluoronaphthylmethyl, hydroxynaphthylmethyl, methoxynaphthylmethyl, fluoronaphthylmethyl and chloronaphthylmethyl groups. As to said group, $C_7$–$C_{16}$ aralkyl groups (optionally having from 1–3 substituting moieties $\alpha_{1c}$, $\alpha_{1d}$ and $\alpha_{1e}$ on the aryl moiety) are preferred, further phenyl-$C_1$–$C_6$ alkyl groups (optionally having from 1–3 substituting moieties $\alpha_{1c}$, $\alpha_{1d}$ and $\alpha_{1e}$ on the phenyl moiety) are more preferred, further phenyl-$C_1$–$C_6$ alkyl groups (optionally having one substituting moiety $\alpha_{1c}$, $\alpha_{1d}$ or $\alpha_{1e}$ on the phenyl moiety) are yet more preferred, phenyl-$C_1$–$C_4$ alkyl groups (optionally having one substituting moiety $\alpha_{1c}$, $\alpha_{1d}$ or $\alpha_{1e}$ on the phenyl moiety) are still further preferred, and further phenyl-$C_1$–$C_2$ alkyl groups (optionally having one substituting moiety $\alpha_{1c}$, $\alpha_{1d}$ or $\alpha_{1e}$ on the phenyl moiety) are the most preferred.

In the case where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_6$–$C_{10}$ arylsulfonyl group (optionally having 1–5 substituting moieties $\alpha_{1c}$, $\alpha_{1d}$ and $\alpha_{1e}$)", examples of said group having such a substituting moiety are methylphenylsulfonyl, acetylphenylsulfonyl, benzoylphenylsulfonyl, biphenylylsulfonyl, methylbiphenylylsulfonyl, methylnaphthylsulfonyl, acetylnaphthylsulfonyl and benzoylnaphthylsulfonyl groups. As to said group, $C_6$–$C_{10}$ arylsulfonyl groups (optionally having from 1–3 substituting moieties $\alpha_{1c}$, $\alpha_{1d}$ and $\alpha_{1e}$) are preferred, further phenylsulfonyl groups (optionally having from 1–3 substituting moieties $\alpha_{1c}$, $\alpha_{1d}$ and $\alpha_{1e}$) are more preferred, and furthermore phenylsulfonyl groups (optionally having one substituting moiety $\alpha_{1c}$, $\alpha_{1d}$ or $\alpha_{1e}$) are the most preferred.

In the case-where $R_{1c}$, $R_{1d}$, $R_{1e}$, $R_{2c}$, $R_{2d}$, $R_{2e}$, $R_{3c}$, $R_{3d}$ and $R_{3e}$ represent a "$C_7$–$C_{16}$ aralkylsulfonyl group (optionally having from 1–5 substituting moieties $\alpha_{1c}$, $\alpha_{1d}$ and $\alpha_{1e}$ on the aryl moiety thereof)", examples of said group having such a substituting moiety are methylbenzylsulfonyl, acetylbenzylsulfonyl, benzoylbenzylsulfonyl, biphenylylmethylsulfonyl, methylbiphenylylmethylsulfonyl, methylnaphthylmethylsulfonyl, acetylnaphthylmethylsulfonyl, benzoylnaphthylmethylsulfonyl, methylphenethylsulfonyl, acetylphenethylsulfonyl, methylnaphthylethylsulfonyl, acetylnaphthylethylsulfonyl, methylphenylbutylsulfonyl, acetylphenylbutylsulfonyl, methylnaphthylbutylsulfonyl and acetylnaphthylbutylsulfonyl groups. As to said group, $C_7$–$C_{16}$ aralkylsulfonyl groups (optionally having from 1–3 substituting moieties $\alpha_{1c}$, $\alpha_{1d}$ and $\alpha_{1e}$ on the aryl moiety) are preferred, further phenyl-$C_1$–$C_6$ alkylsulfonyl groups (optionally having from 1–3 substituting moieties $\alpha_{1c}$, $\alpha_{1d}$ and $\alpha_{1e}$ on the phenyl moiety) are more preferred, furthermore phenyl-$C_1$–$C_4$ alkylsulfonyl groups (optionally having one substituting moiety $\alpha_{1c}$, $\alpha_{1d}$ or $\alpha_{1e}$ on the phenyl moiety) are yet more preferred, and benzylsulfonyl and phenethylsulfonyl groups (optionally having one substituting moiety $\alpha_{1c}$, $\alpha_{1d}$ or $\alpha_{1e}$ on the phenyl moiety) are the most preferred.

In the case where $Z_{1c}$, $Z_{1d}$ and $Z_{1e}$ represent a "$C_6$–$C_{10}$ aryloxy group (optionally having from 1–5 substituting moieties $\alpha_{1c}$, $\alpha_{1d}$ and $\alpha_{1e}$)", examples of said group having such a substituting moiety are methylphenoxy, trifluoromethylphenoxy, hydroxyphenoxy, 4-hydroxy-2,3,5-trimethylphenoxy, 3,5-di-t-butyl-4-hydroxyphenoxy, cyclopropylphenoxy, adamantylphenoxy, cyanophenoxy, nitrophenoxy, 4-amino-3,5-dimethylphenoxy, acetylphenoxy, methoxyphenoxy, benzoylphenoxy, fluorophenoxy, difluorophenoxy, chlorophenoxy, dichlorophenoxy, nitrophenoxy, (dimethylamino)phendxy, 4-(4-trifluoromethylphenylcarbamoylamino)-3,5-dimethylphenoxy, biphenylyloxy, methylbiphenylyloxy, dimethylaminophenoxy, methylnaphthyloxy, trifluoronaphthyloxy, hydroxynaphthyloxy, methoxynaphthyloxy, fluoronaphthyloxy and chloronaphthyloxy groups. As to said group, $C_6$–$C_{10}$ aryloxy groups (optionally having from 1–3 substituting moieties $\alpha_{1c}$, $\alpha_{1d}$ and $\alpha_{1e}$) are preferred, further phenoxy groups (optionally having from 1–5 substituting moieties $\alpha_{1c}$, $\alpha_{1d}$ and $\alpha_{1e}$) are more preferred, furthermore phenoxy groups (optionally having one or two substituting moieties $\alpha_{1c}$, $\alpha_{1d}$ and $\alpha_{1e}$) are yet more preferred, and phenoxy groups (optionally having one substituting moiety $\alpha_{1c}$, $\alpha_{1d}$ or $\alpha_{1e}$) are the most preferred.

In the case where $Z_{1c}$, $Z_{1d}$ and $Z_{1e}$ represent a "$C_7$–$C_{16}$ aralkyloxy group (optionally having from 1–5 substituting moieties $\alpha_{1c}$, $\alpha_{1d}$ and $\alpha_{1e}$ hereafter described on the aryl moiety thereof)", examples of said group having such a substituting moiety are methylbenzyloxy, trifluoromethylbenzyloxy, hydroxybenzyloxy, 4-hydroxy-2,3,5-trimethylbenzyloxy, 3,5-di-t-butyl-4-hydroxybenzyloxy, adamantylbenzyloxy, 4-amino-3,5-dimethylbenzyloxy, acetylbenzyloxy, methoxybenzyloxy, benzoylbenzyloxy, fluorobenzyloxy, difluorobenzyloxy, chlorobenzyloxy, dichlorobenzyloxy, nitrobenzyloxy, (dimethylamino)benzyloxy, biphenylylmethoxy, methylbiphenylylmethoxy, methylphenethyloxy, trifluoromethylphenethyloxy, hydroxyphenethyloxy, 4-hydroxy-2,3,5-trimethylphenethyloxy, 3,5-di-t-butyl-4-hydroxyphenethyloxy, adamantylphenethyloxy, 4-amino-3,5-dimethylphenethyloxy, acetylphenethyloxy, methoxyphenethyloxy, benzoylphenethyloxy, fluorophenethyloxy, difluorophenethyloxy, chlorophenethyloxy, nitrophenethyloxy, (dimethylamino)phenethyloxy, biphenylylethyloxy, methylbiphenylylethoxy, methylphenylbutoxy, trifluoromethylphenylbutoxy, hydroxyphenylbutoxy, 4-hydroxy-2,3,5-trimethylphenylbutoxy, 3,5-di-t-butyl-4-hydroxyphenylbutoxy, adamantylphenylbutoxy, 4-amino-3,5-dimethylphenylbutoxy, acetylphenylbutoxy, methoxyphenylbutoxy, fluorophenylbutoxy, chlorophenylbutoxy, nitrophenylbutoxy, (dimethylamino)phenylbutoxy, biphenylbutoxy, methylnaphthylmethoxy, trifluoronaphthylmethoxy, hydroxynaphthylmethoxy, methoxynaphthylmethoxy, fluoronaphthylmethoxy and chloronaphthylmethoxy groups. As to said group, $C_7$–$C_{16}$ aralkyloxy groups (optionally having from 1–3 substituting moieties $\alpha_{1c}$, $\alpha_{1d}$ and $\alpha_{1e}$ on the aryl moiety thereof) are preferred, further phenyl-$C_1$–$C_6$ alkyloxy groups (optionally having from 1–3 substituting moieties $\alpha_{1c}$, $\alpha_{1d}$ and $\alpha_{1e}$ on the phenyl moiety) are more preferred, furthermore phenyl-$C_1$–$C_6$ alkyloxy groups (optionally having one substituting moiety $\alpha_{1c}$, $\alpha_{1d}$ or $\alpha_{1e}$ on the phenyl moiety) are yet more preferred, moreover phenyl-$C_1$–$C_4$ alkyloxy groups (optionally having one substituting moiety $\alpha_{1c}$, $\alpha_{1d}$ or $\alpha_{1e}$ on the phenyl moiety) are still more preferred, and phenyl-$C_1$–$C_2$ alkyloxy groups (optionally having one substituting moiety $\alpha_{1c}$, $\alpha_{1d}$ or $\alpha_{1e}$ on the phenyl moiety) are the most preferred.

In the case where $Z_{1c}$, $Z_{1d}$ and $Z_{1e}$ represent a "saturated heterocyclic ring-oxy group (optionally having from 1–5 substituting moieties $\alpha_{1c}$, $\alpha_{1d}$ and $\alpha_{1e}$)", said group means a monovalent group mainly derived from a monosaccharide. Said monosaccharides illustratively include pentoses such as arabinose, xylose, ribose, etc.; hexoses such as glucose, galactose, mannose, etc.; aminosugars such as glucosamine, galactosamine, etc.; and uronic acids such as glucuronic acid, etc. As to said groups, monovalent groups derived from monosaccharides showing physiological activity in vivo in warm-blooded animals (particularly human beings) are preferred, further monovalent groups derived from an uronic acid are more preferred, and monovalent groups derived from glucuronic acid are particularly preferred.

In the case where $Z_{2c}$, $Z_{2d}$, $Z_{2e}$, $Z_{3c}$, $Z_{3d}$ and $Z_{3e}$ represent a "saturated heterocyclic ring group (optionally having from 1–5 substituting moieties $\alpha_{1c}$, $\alpha_{1d}$ and $\alpha_{1e}$)", said group means a monovalent group mainly derived by removing the hydroxy group from said monosaccharide. As to said group, monovalent groups derived from monosaccharides showing phyiological activity in vivo in warm-blooded animals (particularly human beings) are preferred, further monovalent groups derived from an uronic acid are more preferred, and monovalent groups derived from glucuronic acid are particularly preferred.

In the case where $Z_{1c}$, $Z_{1d}$ and $Z_{1e}$ represent a "monocyclic type heteroaromatic ring-oxy group (optionally having from 1–5 substituting moieties $\alpha_{1c}$, $\alpha_{1d}$ and $\alpha_{1e}$)", examples of said group are fluorofuryloxy, fluorothienyloxy, fluoropyrrolyloxy, fluorooxazolyloxy, fluorothiazolyloxy, fluorotriazolyloxy, fluoropyranyloxy, fluoropyridyloxy, fluoropyridazinyloxy, fluoropyrimidinyloxy, methylfuryloxy, methylthienyloxy, methylpyrrolyloxy, methyloxazolyloxy, methylthiazolyloxy, methylpyridyloxy, methoxyfuryl, methoxythienyl, methoxypyrrolyloxy, methoxyoxazolyloxy, methoxythiazolyloxy, methoxypyridyloxy, dimethylaminofuryloxy, dimethylaminothienyloxy, dimethylaminopyrrolyloxy, dimethylaminooxazolyloxy, dimethylaminothiazolyloxy, and dimethylaminopyridyloxy groups. As to said group, monocyclic type heteroaromatic ring-oxy groups (optionally having from 1–3 substituting moieties $\alpha_{1c}$, $\alpha_{1d}$ and $\alpha_{1e}$) are preferred, further 5- or 6-membered monocyclic type heteroaromatic ring-oxy groups (optionally having one or two substituting moieties $\alpha_{1c}$, $\alpha_{1d}$ and $\alpha_{1e}$) are more preferred, furthermore 5- or 6-membered monocyclic type heteroaromatic ring-oxy groups (optionally having one or two substituting moieties $\alpha_{1c}$, $\alpha_{1d}$ and $\alpha_{1e}$) are yet more preferred, and 5- or 6-membered monocyclic type heteroaromatic ring-oxy groups containing one or more heteroatom(s) (optionally having one substituting moiety ($\alpha_{1c}$, $\alpha_{1d}$ or $\alpha_{1e}$) are the most preferred.

In the case where $Z_{1c}$, $Z_{1d}$ and $Z_{1e}$ represent a "$C_6$–$C_{10}$ arylthio group (optionally having from 1–5 substituting moieties $\alpha_{1c}$, $\alpha_{1d}$ and $\alpha_{1e}$)" examples of said group are methylphenylthio, trifluoromethylphenylthio, hydroxyphenylthio, 4-hydroxy-2,3,5-trimethylphenylthio, 3,5-di-t-butyl-4-hydroxyphenylthio, adamantylphenylthio, 4-amino-3,5-dimethylphenylthio, acetylphenylthio, methoxyphenylthio, benzoylphenylthio, fluorophenylthio, difluorophenylthio, chlorophenylthio, dichlorophenylthio, nitrophenylthio, (dimethylamino)phenylthio, biphenylylthio, methylbiphenylylthio, methylnaphthylthio, trifluoronaphthylthio, hydroxynaphthylthio, methoxynaphthylthio, fluoronaphthylthio, and chloronaphthylthio groups. As to said group, $C_6$–$C_{10}$ arylthio groups (optionally having from 1–3 substituting moieties $\alpha_{1c}$, $\alpha_{1d}$ and $\alpha_{1e}$) are preferred, further phenylthio groups (optionally having from 1–3 substituting moieties $\alpha_{1c}$, $\alpha_d$ and $\alpha_{1e}$) are more preferred, furthermore phenylthio groups (optionally having one or two substituting moieties $\alpha_{1c}$, $\alpha_{1d}$ and $\alpha_{1e}$) are yet more preferred, and phenylthio groups (optionally having one substituting moiety $\alpha_{1c}$, $\alpha_{1d}$ or $\alpha_{1e}$) are the most preferred.

In the case where $Z_{1c}$, $Z_{1d}$ and $Z_{1e}$ represent a "$C_7$–$C_{16}$ aralkylthio group (optionally having from 1–5 substituting moieties $\alpha_{1c}$, $\alpha_{1d}$ and $\alpha_{1e}$ on the aryl moiety thereof)", examples of said group having such a substituting moiety are methylbenzylthio, trifluoromethylbenzylthio, hydroxybenzylthio, 4-hydroxy-2,3,5-trimethylbenzylthio, 3,5-di-t-butyl-4-hydroxybenzylthio, adamantylbenzylthio, 4-amino-3,5-dimethylbenzylthio, acetylbenzylthio, methoxybenzylthio, benzoylbenzylthio, fluorobenzylthio, difluorobenzylthio, chlorobenzylthio, dichlorobenzylthio, nitrobenzylthio, (dimethylamino)benzylthio, biphenylylmethylthio, methylbiphenylylmethylthio, methylphenethylthio, trifluoromethylphenethylthio, hydroxyphenethylthio, 4-hydroxy-2,3,5-trifluoro-phenethylthio, 3,5-di-t-butyl-4-hydroxyphenethylthio, adamantylphenethylthio, 4-amino-3,5-dimethylphenethylthio, acetylphenethylthio, methoxyphenethylthio, benzoylphenethylthio, fluorophenethylthio, difluorophenethylthio, chlorophenethylthio, nitrophenethylthio, (dimethylamino)phenethylthio, biphenylylethylthio, methylbiphenylylethylthio, methylphenylbutylthio, trifluoromethylphenylbutylthio, hydroxyphenylbutylthio, 4-hydroxy-2,3,5-trimethylphenylbutylthio, 3,5-di-t-butyl-4-hydroxyphenylbutylthio, adamantylphenylbutylthio, 4-amino-3,5-dimethylphenylbutylthio, acetylphenylbutylthio, methoxyphenylbutylthio, fluorophenylbutylthio, chlorophenylbutylthio, nitrophenylbutylthio, (dimethylamino)phenylbutylthio, biphenylylbutylthio, methylnaphthylmethylthio, trifluoromethylnaphthylmethylthio, hydroxynaphthylmethylthio, methoxynaphthylmethylthio, fluoronaphthylmethylthio, and chloronaphthylmethylthio groups. As to said group, $C_7$–$C_{16}$ aralkylthio groups (optionally having from 1–3 substituting moieties $\alpha_{1c}$, $\alpha_{1d}$ and $\alpha_{1e}$ on the aryl moiety) are preferred, further phenyl-$C_1$–$C_6$ alkylthio groups (optionally having from 1–3 substituting moieties $\alpha_{1c}$, $\alpha_{1d}$ and $\alpha_{1e}$ on the phenyl moiety) are more preferred, furthermore phenyl-$C_1$–$C_6$ alkylthio groups (optionally having one substituting moiety $\alpha_{1c}$, $\alpha_{1d}$ or $\alpha_{1e}$ on the phenyl moiety) are yet more preferred, then phenyl-$C_1$–$C_4$ alkylthio groups (optionally having one substituting moiety $\alpha_{1c}$, $\alpha_{1d}$ or $\alpha_{1e}$ on the phenyl moiety) are still more preferred, and phenyl-$C_1$–$C_2$ alkylthio groups (optionally having one substituting moiety $\alpha_{1c}$, $\alpha_{1d}$ or $\alpha_{1e}$ on the phenyl moiety) are the most preferred.

In the case where $Z_{1c}$, $Z_{1d}$ and $Z_{1e}$ represent a "saturated heterocyclic ring-thio group (optionally having from 1–5 substituting moieties $\alpha_{1c}$, $\alpha_{1d}$ and $\alpha_{1e}$)", examples of said group having such a substituting moiety are methylpyrrolidylthio, methoxypyrrolidylthio, methyltetrahydrofuranylthio, methoxytetrahydrofuranylthio, methylpiperidylthio, methoxypiperidylthio, methyltetrahydropyranylthio, methoxytetrahydropyranylthio, methyltetrahydrothiopyranylthio, methoxytetrahydrothiopyranylthio, methylpiperazinylthio, methoxypiperazinylthio, methylmorpholylthio, methoxymorpholylthio, methylthiomorpholylthio and methoxythiomorpholylthio groups. As to said group, 5- or 6-membered saturated heterocyclic ring-thio groups (optionally having from 1–5 substituting moieties $\alpha_{1c}$, $\alpha_{1d}$ and $\alpha_{1e}$) are preferred, further 5- or 6-membered saturated heterocyclic ring-thio groups (optionally having from 1–3 substituting moieties $\alpha_{1c}$, $\alpha_{1d}$ and $\alpha_{1e}$) are more preferred, and furthermore 5- or 6-membered saturated heterocyclic ring-thio groups (optionally having one substituting moiety $\alpha_{1c}$, $\alpha_{1d}$ or $\alpha_{1e}$) are the most preferred.

In the case where $Z_{1c}$, $Z_{1d}$ and $Z_{1e}$ represent a "monocyclic type heteroaromatic ring-thio group (optionally having from 1–5 substituting moieties $\alpha_{1c}$, $\alpha_{1d}$ and $\alpha_{1e}$)", examples of said group having the substituting moiety are fluorofurylthio, fluorothienylthio, fluoropyrrolylthio, fluorooxazolylthio, fluorothiazolylthio, fluorotriazolylthio, fluoropyranylthio, fluoropyridylthio, fluoropyridazinylthio, fluoropyrimidinylthio, methylfurylthio, methylthienylthio, methylpyrrolylthio, methyloxazolylthio, methylthiazolylthio, methylpyridylthio, methoxyfurylthio, methoxythienylthio, methoxypyrrolylthio, methoxyoxazolylthio, methoxythiazolylthio, methoxypyridylthio, dimethylaminofurylthio, dimethylaminothienylthio, dimethylaminopyrrolylthio, dimethylaminooxazolylthio, dimethylaminothiazolylthio and dimethylaminopyridylthio groups. As to said group, 5–7 membered monocyclic type heteroaromatic ring-thio groups (optionally having from 1–3 subsituting moieties $\alpha_{1c}$, $\alpha_{1d}$ and $\alpha_{1e}$ are preferred, further 5–6 member monocyclic type heteroaromatic ring-thio groups (optionally having one or two substituting moieties $\alpha_{1c}$, $\alpha_{1d}$ and $\alpha_{1e}$) are more preferred, furthermore 5 or 6-membered monocyclic type heteroaromatic ring-thio groups (optionally having one substituting moiety $\alpha_{1c}$, $\alpha_{1d}$ or $\alpha_{1e}$) are yet more preferred, and 5- or 6-membered monocyclic type heteroaromatic ring-thio groups containing one or two heteroatom(s) (optionally having one substituting moiety $\alpha_{1c}$, $\alpha_{1d}$ or $\alpha_{1e}$) are the most preferred.

In the case where $Z_{1c}$, $Z_{1d}$ and $Z_{1e}$ represent an "amino group (optionally having one or two substituting moieties $\alpha_{1c}$, $\alpha_{1d}$ and $\alpha_{1e}$)", examples of said group are amino, methylamino, ethylamino, propylamino, isopropylamino, butylamino, s-butylamino, t-butylamino, pentylamino, hexylamino, dimethylamino, diethylamino, N-ethyl-N-methylamino, dipropylamino, dibutylamino, dipentylamino, dihexylamino, phenylamino, 1- or 2-indenylamino, 1- or 2-naphthylamino, diphenylamino, formylamino, acetylamino, propionylamino, butyrylamino, isobutyrylamino, valerylamino, isovalerylamino, pivaloylamino, hexanoylamino, acryloylamino, methacryloylamino, crotonoylamino, benzoylamino, 1-indanecarbonylamino, 1- or 2-naphthoylamino, 2,6-diisopropylbenzoylamino, 1-indanecarbonylamino, 1- or 2-naphthoylamino, phenylacetylamino, 3-phenylpropionylamino, 4-phenylbutyrylamino, 5-phenylpentanoylamino, 6-phenylhexanoylamino, cyclopropanecarbonylamino, cyclobutanecarbonylamino, cyclopentanecarbonylamino, cyclohexanoylamino, pyrrolylcarbonylamino, imidazolylcarbonylamino, pyrazolylcarbonylamino, triazolylcarbonylamino, tetrazolylcarbonylamino, nicotinoylamino, isonicotinoylamino, pyrazinylcarbonylamino, pyrimidinylcarbonylamino, pyridazinylcarbonylamino, thiazolylcarbonylamino, oxazolylcarbonylamino, oxadiazolylcarbonylamino, thiadiazolylcarbonyl-amino, 4-trifluoromethylphenylcarbamoylamino, N,N-diacetylamino, N-formyl-N-hexylamino, N-acetyl-N-methylamino, N-acetyl-N-ethylamino, N-acetyl-N-propylamino, N-acetyl-N-butylamino, N-acetyl-N-pentylamino, N-acetyl-N-hexylamino, N-benzoyl-N-methylamino, N-benzoyl-N-ethylamino, N-benzoyl-N-propylamino, N-benzoyl-N-butylamino, N-benzoyl-N-pentylamino, N-benzoyl-N-hexylamino, N-benzoyl-N-phenylamino, N-benzyl-N-benzoylamino, N-hexyl-N-1-naphthoylamino, N-hexyl-N-2-naphthoylamino, N-hexyl-N-phenylacetylamino, N-isobutyl-N-cycloheptanecarbonylamino, N-butyl-N-nicotinoylamino, N-hexyl-N-nicotinoylamino and N-isonicotinoyl-N-hexylamino groups. As to said group, amino groups (optionally having one or two substituting moieties selected from $C_1$–$C_6$ alkyl, $C_1$–$C_7$ aliphatic acyl, $C_6$–$C_{10}$ aryl optionally having from 1–3 substituting moieties $\beta_{1c}$, $\beta_{1d}$ and $\beta_{1e}$, $C_7$–$C_{16}$ aralkyl optionally having from 1–3 substituting moieties $\beta_{1c}$, $\beta_{1d}$ and $\beta_{1e}$ on the aryl moiety thereof, and $C_7$–$C_{11}$ arylcarbonyl optionally having from 1–3 substituting moieties $\beta_{1c}$, $\beta_{1d}$ and $\beta_{1e}$ on the aryl moiety thereof) are preferred, and further amino groups (optionally having one or two substituting moieties $\beta_{1c}$, $\beta_{1d}$ and $\beta_{1e}$ selected from $C_1$–$C_4$ alkyl, $C_1$–$C_2$ aliphatic acyl, phenyl optionally having one substituting moiety $\beta_{1c}$, $\beta_{1d}$ or $\beta_{1e}$, phenyl $C_1$–$C_4$ alkyl optionally having one substituting moiety $\beta_{1c}$, $\beta_{1d}$ or $\beta_{1e}$ on the phenyl moiety thereof, and benzoyl optionally having one substituting moiety $\beta_{1c}$, $\beta_{1d}$ or $\beta_{1e}$ on the phenyl moiety thereof) are more preferred.

The α-substituted carboxylic acid derivatives of formulae (Ic) to (Ie) in the present invention having a carboxyl group can be converted into their salts according to conventional methods. Examples of such salts are alkali metal salts such as sodium salt, potassium salt or lithium salt; alkaline earth metal salts such as calcium salt or magnesium salt; metal salts such as the aluminum salt, iron salt, zinc salt, copper salt, nickel salt, cobalt salt, etc.; inorganic salts such as ammonium salt; amine salts like organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt; N-benzyl-N-phenethylamine salt, piperazine salt, tetramethylammonium salt and tris(hydroxymethyl)aminomethane salt.

The α-substituted carboxylic acid derivatives of formulae (Ic) to (Ie) in the present invention can be converted into their salts both in the case of having any basic moiety such as a pyridyl group, quinolyl group or the like and also in the case of having no bases. Examples of such salts are hydrohalogenic acid salts such as hydrofluoride, hydrochloride, hydrobromide, hydroiodide; inorganic acid salts such as nitrate, perchlorate, sulfate, phosphate; lower alkanesulfonic acid salts such as methanesulfonate, trifluoromethanesulfonate, ethanesulfonate; arylsulfonic acid salts such as benzenesulfonate, p-toluenesulfonate, etc.; amino acid salts such as glutamate, aspartate, etc.; organic carboxylic acid salts such as fumarate, succinate, citrate, tartrate, oxalate, maleate; amino acid salts such as ornithine, glutamate, aspartate and the like. Of these, hydrohalogenic acid salts and organic acid salts are preferred.

The α-substituted carboxylic acid derivatives of formulae (Ic) to (Ie) in the present invention can be converted into their pharmacologically acceptable esters according to conventional methods. The pharmacologically acceptable esters of the α-substituted carboxylic acid derivatives of formulae (Ic) to (Ie) are not particularly limited as long as they can be used medically and their pharmacological acceptability is comparable with that of the α-substituted carboxylic acid derivatives of formulae (Ic) to (Ie).

The esters of the α-substituted carboxylic acid derivatives of formulae (Ic) to (Ie) in the present invention illustratively include $C_1$–$C_6$ alkyl substituted with $C_1$–$C_6$ alkyl, $C_7$–$C_{19}$ aralkyl or $C_1$–$C_7$ aliphatic acyloxy, $C_1$–$C_6$ alkyl substituted with $C_1$–$C_7$ alkyloxycarbonyloxy, $C_1$–$C_6$ alkyl substituted with $C_5$–$C_7$ cycloalkylcarbonyloxy, $C_1$–$C_6$ alkyl substituted with $C_6$–$C_8$ cycloalkyloxycarbonyloxy, $C_1$–$C_6$ alkyl substituted with $C_7$–$C_{11}$ arylcarbonyloxy, $C_1$–$C_6$ alkyl substituted with $C_7$–$C_{11}$ aryloxycarbonyloxy, and 2-oxo-1,3-dioxolen-4-ylmethyl group having $C_1$–$C_6$ alkyl as a substituent at the 5-position.

Concerning the ester group, $C_1$–$C_6$ alkyl groups include illustratively methyl, ethyl, propyl, isopropyl, butyl, isobutyl, s-butyl, t-butyl, pentyl, methylbutyl, dimethylpropyl, ethylpropyl, hexyl, methylpentyl, dimethylbutyl, ethylbutyl, and trimethylpropyl groups. $C_1$–$C_4$ alkyl groups are preferred, further methyl, ethyl, propyl, isopropyl, butyl and isobutyl groups are more preferred, and methyl or ethyl group is the most preferred.

$C_7$–$C_{19}$ aralkyl groups include benzyl, phenethyl, phenylpropyl, phenylbutyl, naphthylmethyl and benzyl groups. The benzyl group is preferred.

$C_5$–$C_7$ cycloalkyl groups include cyclopentyl, cyclohexyl and cycloheptyl groups. The cyclohexyl group is preferred.

$C_6$–$C_{10}$ aryl groups include phenyl and naphthyl groups, and the phenyl group is preferred.

Preferred examples of the ester residue are methyl, ethyl, propyl, isopropyl, butyl, isobutyl, t-butyl, benzyl, acetoxymethyl, 1-(acetoxy)ethyl, propionyloxymethyl, 1-propionyloxyethyl, butyryloxymethyl, 1-butyryloxyethyl, 1-isobutyryloxyethyl, valeryloxymethyl, 1-valeryloxyethyl, isovaleryloxymethyl, 1-isovaleryloxyethyl, pivaloyloxymethyl, 1-pivaloyloxyethyl, methoxycarbonyloxymethyl, 1-methoxycarbonyloxyethyl, ethoxycarbonyloxymethyl, 1-ethoxycarbonyloxyethyl, propoxycarbonyloxymethyl, 1-propoxycarbonyloxyethyl, isopropoxycarbonyloxymethyl, 1-isopropoxycarbonyloxyethyl, butoxycarbonyloxymethyl, 1-butoxycarbonyloxyethyl, isobutoxycarbonyloxymethyl, 1-isobutoxycarbonyloxyethyl, t-butoxycarbonyloxymethyl, 1-(t-butoxycarbonyloxy)ethyl, cyclopentanecarbonyloxymethyl, 1-cyclopentanecarbonyloxyethyl, cyclohexanecarbonyloxymethyl, 1-cyclohexanecarbonyloxyethyl, cyclopentyloxycarbonyloxymethyl, 1-cyclopentyloxycarbonyloxyethyl, cyclohexyloxycarbonyloxymethyl, 1-cyclohexyloxycarbonyloxyethyl, benzoyloxymethyl, 1-benzoyloxyethyl, phenoxycarbonyloxymethyl, 1-phenoxycarbonyloxyethyl and 5-methyl-2-oxo-1,3-dioxolen-4-ylmethyl groups.

The amides of the α-substituted carboxylic acid derivatives of general formulae (Ic) to (Ie) in the present invention mean compounds in which the carboxyl group of the α-substituted carboxylic acid derivatives and ammonia are condensed with dehydration. Concretely, they are prepared by converting the carboxyl group into a —$CONH_2$ group.

The compounds of the present invention involve various isomers. For example, the carbon atom at the 2-position of the α-substituted carboxylic acid derivatives of formulae (Ic) to (Ie) is asymmetrical, and any asymmetric carbon exists on the substituent. So, optical isomers may exist in the compounds of the invention.

Thus, the α-carbon atom is an asymmetric carbon to which $R_{2c}$, $R_{2d}$, $R_{2e}$, $Y_c$, $Y_d$, $Y_e$ and the nitrogen atom are bonded, as a result of which stereoisomers in R conformation and S conformation exist. The present invention involves each isomer or a mixture of isomers in an arbitrary ratio. Such stereoisomers can be prepared by synthesizing α-substituted carboxylic acid derivatives (Ic)–(Ie) from optically resolved starting compounds or by subjecting once synthesized α-substituted carboxylic acid derivatives (Ic)–(Ie), if desired, to optical resolution by conventional optical resolution methods or separating methods, or by asymmetric synthesis.

Further, in the case where $Y_c$, $Y_d$ and $Y_e$ represent a sulfoxide group, the sulfur atom becomes an asymmetric center to afford optical isomers. Also in this case, the respective isomers or a mixture in an arbitrary ratio are included in the scope of the present invention, and such stereoisomers can be optically resolved by conventional optical resolution methods or separating methods, or they can be also prepared by asymmetric synthesis.

Further, geometric isomers can exist also in the cases of those compounds having any double bond(s).

The present invention includes all these kinds of isomers.

In addition, the compounds (Ic) to (Ie) in the present invention may absorb water, be attached to adsorbed water, be converted into a hydrate or form a solvate by being allowed to remain in the atmosphere or by being recrystallized. They are to be included in the present invention.

Furthermore, compounds (Ic)–(Ie) of the present invention may absorb another kind of solvent to give a solvate, which will be included in the present invention.

Moreover, compounds, which may be converted in vivo by metabolism into the α-substituted carboxylic acid derivatives (Ic)–(Ie) or pharmacologically acceptable salts thereof of the present invention, namely so-called pro-drugs, are included also in this invention.

BEST MODE FOR CARRYING OUT THE INVENTION

In the present invention, one or more diuretics can be used. In addition, one or more insulin sensitizers can be used.

A diuretic and an insulin sensitizer can be co-administered as a combination drug. In addition, they can be independently or simultaneously administered. Furthermore, each agent can be independently administered at suitable intervals, and either agent can be administered prior to the other. The maximum administration interval of the two classes of agents to demonstrate the excellent effects brought about by said two classes of agents can be determined by clinical practice or by animal studies.

The administration route of the diuretic and insulin sensitizer used in the present invention is generally the oral administration route. Thus, it is possible that the two classes of agents can be prepared in the form of two separate administration units or in the form of a single administration unit by physically mixing the two classes of agents. Such a formulation has no limitation as long as the combination agent is prepared using conventional pharmaceutical formulation techniques. Powders, granules, tablets and capsules are considered as acceptable preparations for the combination agents.

These pharmaceutical formulations can be prepared using known additives such as excipients, binders, disintegrants, lubricants, solubilizers, flavoring agents, coating agents and the like according to conventional methods.

For instance, in order to formulate tablets, known additives in this field can be used, for example excipients such as lactose, sucrose, sodium chloride, glucose, urea, starch, calcium carbonate, kaolin, crystalline cellulose, silicic acid, etc.; binders such as water, ethanol, propanol, simple syrup, glucose solution, starch solution, gelatin solution, carboxymethyl cellulose, shellac, methyl cellulose, potassium phosphate, polyvinylpyrrolidone, etc.; disintegrants such as dry starch, sodium alginate, agar powder, laminaran powder, sodium hydrogencarbonate, calcium carbonate, polyoxyethylene sorbitan fatty acid ester, sodium lauryl sulfate, stearic acid monoglyceride, starch, lactose, etc.; disintegration suppressors such as sucrose, stearin, cacao butter, hydrogenated oil, etc.; absorbefacients such as quaternary ammonium bases, sodium lauryl sulfate, etc.; humectants such as glycerin, starch, etc.; absorbents such as starch, lactose, kaolin, bentonite, colloidal silicic acid, etc.; and lubricants such as purified talc, stearates, boric acid powder, polyethylene glycol, etc. In addition, coated tablets, for instance, sugar-coated tablets, gelatin-coated tablets, enteric coated tablets or film-coated tablets or double-layer tablets or multi-layers tablets can be prepared, if necessary.

In order to formulate pills, known carriers in this field can be used. For instance, excipients such as glucose, lactose, starch, cacao butter, hydrogenated vegetable oil, kaolin, talc, etc.; binders such as gum Arabic powder, tragacanth powder, gelatin, ethanol, etc.; disintegrants such as laminaran agar, etc. can be listed. Furthermore, colorants, preservatives, flavors, sweeteners and other pharmaceuticals-can be contained.

The amounts of the active compounds in the preparations described above are not limited and can be selected from a wide range. However, it is considered to be adequate that their weight percentage should be from 1–70%; preferably from 1–30%.

The doses of the diuretic and insulin sensitizer and their ratios may be widely varied according to various conditions including activity of the compounds, symptoms, age and body weight of the patient.

Although the doses of the diuretic and insulin sensitizer can be widely varied, the daily dose (mg/day) is usually from 0.01–40 mg and from 0.05–500 mg, respectively (preferably from 0.1–40 mg and from 0.5–200 mg, respectively).

The ratios of the two classes of agents' doses can be widely varied, but the dose ratio of the diuretic and insulin sensitizer is normally within the range of from 1:200 to 200:1 by weight (preferably from 1:100 to 100:1).

In the present invention, the diuretic and insulin sensitizer are administered simultaneously or independently at different times, at the doses described above, from once to several times per day.

EXAMPLE

Example 1

Improving effects of co-administration of a diuretic, furosemide, on increasing heart-weight and edema elicited by 5-[4-(6-methoxy-1-methyl-1H-benzimidazol-2-ylmethoxy)benzyl]thiazolidine-2,4-dione hydrochloride (compound A).

(1) Increases in Heart-weight and Circulating Serum Volume

After 5-[4-(6-methoxy-1-methyl-1H-benzimidazol-2-ylmethoxy)benzyl]thiazolidine-2,4-dione hydrochloride (200 mg/kg) was repeatedly and orally administered by gavage for 3 or 7 successive days to female Wistar rats (7 weeks old, Charles River Japan, Inc.), circulating serum volume was determined by Evans blue methods and heart-weight recorded. The results are summarized in Table 1.

TABLE 1

| Duration of Administration | Ratio against control | |
|---|---|---|
| (day) | Heart-Weight | Circulating Serum volume |
| 3 | $1.03^{a)}$ | $1.18^{a)*}$ |
| 7 | $1.22^{b)**}$ | $1.30^{b)**}$ |

Note:
$^{a)}$n = 5–6;
$^{b)}$n = 12;
*$p < 0.05$;
**$p < 0.01$ (Student's t-test)

Circulating serum volume and heart-weight were increased after administration for both 3 and 7 days. Therefore the increase in heart-weight elicited by repeated administration of 5-[4-(6-methoxy-1-methyl-1H-benzimidazol-2-ylmethoxy)benzyl]thiazolidine-2,4-dione hydrochloride is considered due to secondary hypervolume-loading caused by increases in circulating serum volume, which is considered to be owing to hypersensitivity to insulin, elicited by the compound.

(2) Improving Effects of Co-administering a Diuretic, Furosemide, on Increases in Circulating Serum Volume and Heart-weight and Edema Caused by Administration of 5-[4-(6-methoxy-1-methyl-1H-benzimidazol-2-ylmethoxy)benzyl]thiazolidine-2,4-dione hydrochloride 5-[4-(6-Methoxy-1-methyl-1H-benzimidazol-2-ylmethoxy)benzyl]thiazolidine-2,4-dione hydrochloride (200 mg/kg) was repeatedly and orally administered by gavage for 3 or 7 successive days to female Wistar rats (7 weeks old, Charles River Japan, Inc.) and furosemide (120 mg/kg and 240 mg/kg) was dietarily administered during the period. The results are summarized in Table 2 and FIG. 1.

TABLE 2

| | | Macroscopic Observation | | |
|---|---|---|---|---|
| | | Compound A | | |
| | | 200 | 200 | 200 |
| | | | Furosemide | |
| | | 0 | 120 | 240 |
| Edema: | brown adipose tissue | 12/12 | 12/12 | 10/12 |
| | interstitial tissue of thymus | 1/12 | 0/12 | 0/12 |
| | (mean weight of thymus, mg | 521.4 | 450.6 | 375.9) |
| | Subcutaneous tissue | 1/12 | 0/12 | 0/12 |
| Hydrothorax | | 6/12 | 2/12 | 0/12 |

Co-administration of the insulin sensitizer with furosemide suppressed increases in circulating serum volume and heart-weight elicited by compound A, 5-[4-(6-methoxy-1-methyl-1H-benzimidazol-2-ylmethoxy)benzyl]thiazolidine-2,4-dione hydrochloride. Decreases in the number of circulating red blood cells produced by the above compound were also prevented by co-administration with furosemide. Thus it was re-confirmed that increases in heart-weight caused by the compound were brought in by hypervolume loading of the circulating plasma. In addition, decreases in the number of circulating red blood cells are considered changes due to increases in hypervolume of the circulating plasma. Furthermore, edema and hydrothorax, which were associated with administration of compound A, 5-[4-(6-methoxy-1-methyl-1H-benzimidazol-2-ylmethoxy)benzyl]thiazolidine-2,4-dione hydrochloride, were also suppressed by co-administration with furosemide. Thus these changes were confirmed to be related to increases in circulating serum volume.

Example 2

Effects of a co-administering a diuretic, amiloride, on increases in circulating serum volume, heart-weight, and edema caused by administration of 5-[4-(6-methoxy-1-methyl-1H-benzimidazol-2-ylmethoxy)benzyl]thiazolidine-2,4-dione hydrochloride (compound A)

Zucker fatty rats (7 weeks old, SLC, Shizuoka, Japan) were grouped as 5 rats a group. Mean body weight, plasma glucose and glyceride levels, hematocrit value, and the number of red blood cells in each group were similar among the groups. The rats were allowed to take food pellets (F2, Funabashi Farm) and water ad libitum. In the control group, the rats were given only food pellets, while the rest of rats were administered 5-[4-(6-methoxy-1-methyl-1H-benzimidazol-2-ylmethoxy)benzyl]thiazolidine-2,4-dione hydrochloride (suspended in 0.5% solution of carboxymethylcellulose (CMC)) at a volume of 1 ml/kg orally by gavage. In the groups of rats administered the above compound with furosemide (100 mg/ml, suspended in 0.5% CMC solution) or amiloride (10 mg/ml, suspended in distilled water), these diuretics were orally administered by gavage for 14 successive days at a volume of 1 ml/kg. After the final administration, the rats were fasted overnight, and their blood was collected from the tail vein with a capillary treated with heparin and EDTA on the 15th day.

Figure 2:
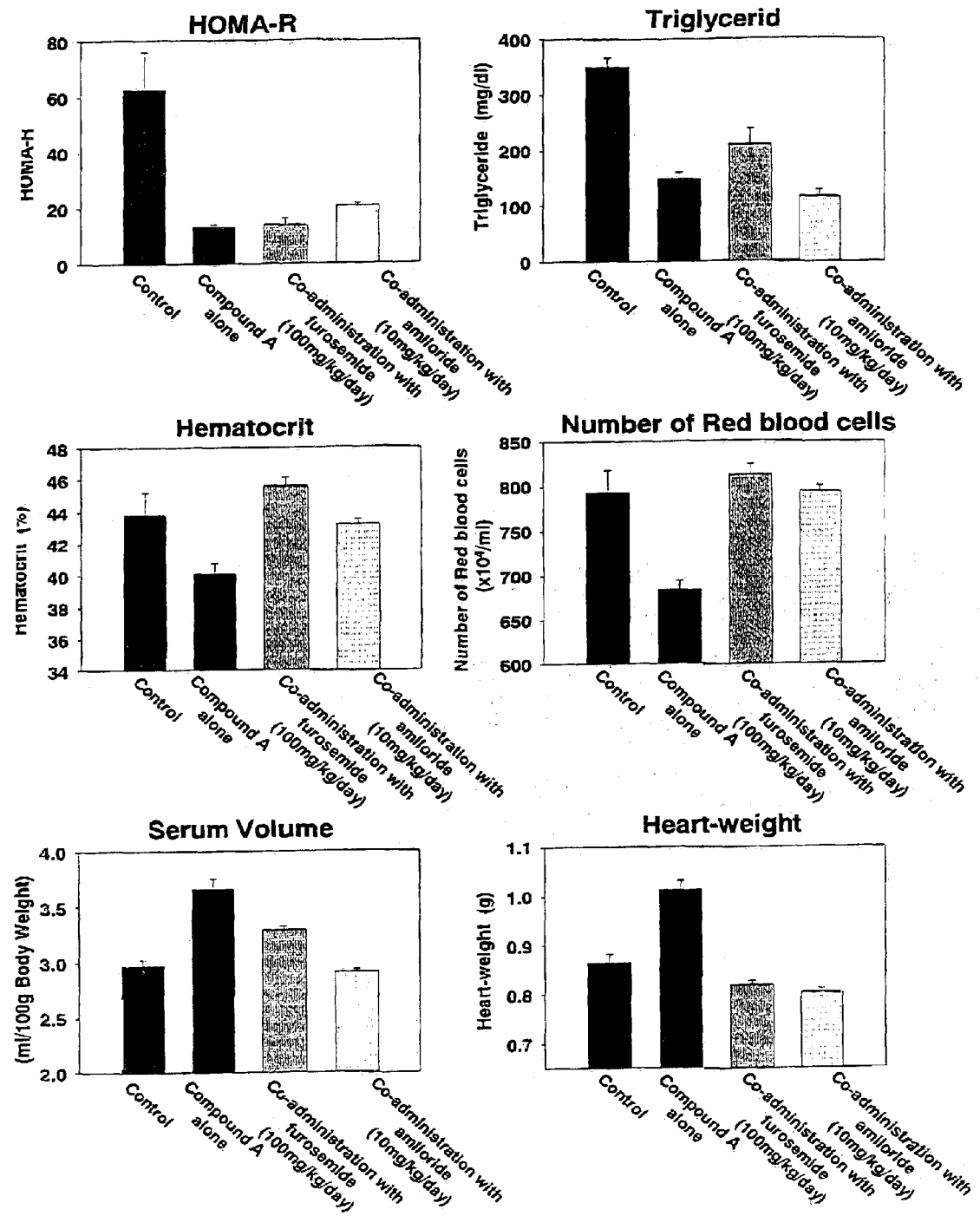
FIG. 2 represents the results of experiments that indicate that increases in serum volume, heart-weight and edema elicited by 5-[4-(6-methoxy-1-methyl-1H-benzimidazol-2-ylmethoxy)benzyl]thiazolidine-2,4-dione hydrochloride (compound A) are suppressed by co-administration with furosemide and amiloride (both diuretics).

Plasma glucose level and blood cell parameters were determined using an automatic analyzer (plasma glucose: Glucoloader GX-T, A&T Corp., blood cell parameters: K-1000, Sysmex Corporation, Kobe, Japan). Triglyceride was detected by the absorbance method with a kit (Triglyceride-E Test Wako, Wako Pure Chemical Industries, Ltd.). Concentrations of insulin and leptin were detected with RIA kits (Rat Insulin RIA Kit, Linco Research Inc.). Furthermore, circulating serum volume was determined by the dilution method using Evans blue. The results are summarized in FIG. 2.

In rats treated with 5-[4-(6-methoxy-1-methyl-1H-benzimidazol-2-ylmethoxy)benzyl]thiazolidine-2,4-dione hydrochloride, HOMA-R, an indicator of insulin resistance, and triglyceride levels were remarkably decreased. At the same time, dilution of the blood (decreases in hematocrit value and the number of red blood cells), considered to be due to increases in serum volume, and increases in heart-weight, which were considered due to increases in the serum volume for a long period, were detected.

However, in rats treated with furosemide or amiloride, both blood dilution (decreases in hematocrit value and the number of red blood cells) and increases in heart-weight were suppressed, and the increases in circulating serum volume were also suppressed. Furthermore, although amiloride is a less potent diuretic, amiloride exerted ameliorating effects at least as potent as those of furosemide, a potent diuretic, at a dose of $1/10$ the dose of furosemide.

These diuretics did not impair decreasing actions toward blood glucose levels and triglyceride levels of compound A, 5-[4-(6-methoxy-1-methyl-1H-benzimidazol-2-ylmethoxy)benzyl]thiazolidine-2,4-dione hydrochloride, when they were co-administered with compound A.

From these results, it was clearly shown that the therapeutic effects of insulin sensitizers could be maintained and their side effects specifically decreased by co-administration with diuretics. Furthermore, in rats co-treated with amiloride, the suppression of side effects caused by insulin sensitizers was more potent than those predicted from its diuretic action. The reasons for the potent effects observed were considered to be that insulin sensitizers enhance ENaC activation/expression, and amiloride, an ENaC inhibitor, exerts more potent co-administered effects with the insulin sensitizer.

REFERENCE EXAMPLE

Reference Example 1

5-[4-(6-Methoxy-1-methyl-1H-benzimidazol-2-ylmethoxy)benzyl]thiazolidine-2,4-dione.hydrochloride Reference Example 1(1)

5-[4-(6-Methoxy-1-methyl-1H-benzimidazol-2-ylmethoxy)benzyl]thiazolidine-2,4-dione A reaction mixture of 5-methoxy-N-methyl-1,2-phenylenediamine (21.8 g) (see Reference example 9 of Japanese Patent Application Publication No. Hei 9-295970), 5-(4-methoxycarbonylmethoxybenzyl)thiazolidine-2,4-dione (63.4 g) (see Reference example 21 of Japanese Patent Application Publication No. Hei 9-295970), 1,4-dioxane (250 ml) and concentrated hydrochloric acid (750 ml) was heated under reflux for 60 hours. The reaction mixture was cooled in an ice bath, and the resulting precipitate was filtered off. To this precipitate was added 5% aqueous sodium hydrogencarbonate solution (800 ml), and the mixture was stirred at room temperature for 2 hours. The precipitate was filtered off, dissolved in a mixed solvent of N,N-dimethylformamide (1000 ml) and methanol (200 ml), and then the solution was decolorized with activated charcoal powder. After the activated charcoal powder was filtered out, the solution was concentrated to a volume of about 50 ml. Diethyl ether (750 ml) was added thereto and the resulting solution was allowed to stand for 2 days to give a precipitate, which was filtered off to afford the target compound (20.1 g, mp 267–271° C., Rf-value=0.68 (silica gel chromatography; 5% ethanol-methylene chloride solution)).

Reference Example 1(2)

5-[4-(6-Methoxy-1-methyl-1H-benzimidazol-2-yl-methoxy)benzyl]thiazolidine-2,4-dione.hydrochloride A mixture of 5-[4-(6-methoxy-1-methyl-1H-benzimidazol-2-ylmethoxy)benzyl]thiazolidine-2,4-dione (10.6 g) obtained from Reference example 1(1) and 4N hydrochloric acid-1,4-dioxane (100 ml) was stirred at room temperature for 1 hour. After the reaction mixture was concentrated, ethyl acetate was added thereto, and the resulting precipitate was filtered off and washed with ethyl acetate to afford the target compound (11.0 g, mp 275–277° C.).

$^1$H-Nuclear magnetic resonance spectrum (400 MHz, DMSO-$d_6$, TMS (tetramethylsilane) was used as an internal standard): δ (ppm) 3.11 (1H, dd, J=14 Hz and 9 Hz), 3.34 (1H, dd, J=14 Hz and 4 Hz), 3.89 (3H, s), 3.98 (3H, s), 4.91 (1H, dd, J=9 Hz and 4 Hz), 5.64 (2H, s), 7.14 (2H, d, J=9 Hz), 7.15 (1H, d, J=9 Hz), 7.25 (2H, d, J=9 Hz), 7.50 (1H, s), 7.70 (1H, d, 9 Hz), 12.04 (1H, s, disappeared by addition of $D_2O$).

Reference Example 2

Ethyl 2-(4-chlorophenoxy)-3-[4-[2-[[1-[4-(2-pyridyl)phenyl]ethylidene]aminoxy]ethoxy]phenyl]propionate Ethyl 2-(4-chlorophenoxy)-3-(4-hydroxyphenyl)propionate (504 mg) obtained from the following Reference example 24(d) was dissolved in a mixed solvent of dimethyl sulfoxide (2 ml) and toluene (2 ml), and sodium hydride (55%, 85 mg) was added thereto. After the reaction mixture was stirred at 40° C. for 1 hour, a dimethyl sulfoxide solution (2 ml) of 4'-(2-pyridyl)acetophenone oxime O-2-(methanesulfonyloxy)ethyl ether (649 mg) obtained from the method according to Reference example 2 of WO 97/37970 (EP916651A) was added dropwise thereto. The reaction solution was stirred at 60° C. for 4 hours, and then ethyl acetate and water were added thereto. The obtained organic layer was washed with a saturated aqueous sodium chloride solution, dried over anhydrous magnesium sulfate, and concentrated under reduced pressure. The obtained crude product was purified by chromatography on a silica gel column (eluant; hexane/ethyl acetate=9/1) to afford the target compound (504 mg) as a colorless oil.

$^1$H-NMR (270 MHz, CDCl$_3$): δ (ppm) 1.19 (3H, t, J=7.0 Hz), 2.26 (3H, s), 3.17 (2H, d, J=6.5 Hz), 4.17 (2H, q, J=7.0 Hz), 4.28 (2H, t, J=5.0 Hz), 4.54 (2H, t, J=5.0 Hz), 4.69 (1H, t, J=6.5 Hz), 6.76 (2H, d, J=8.5 Hz), 6.90 (2H, d, J=8.5 Hz), 7.16–7.26 (5H, m), 7.74–7.77 (4H, m), 8.00 (2H, d, J=8.5 Hz), 8.70–8.71 (1H, m).

Reference Example 3

2-(4-Chlorophenoxy)-3-[4-[2-[[1-[4-(2-pyridyl)phenyl]ethylidene]aminoxy]ethoxy]phenyl]propionic acid To a solution of ethyl 2-(4-chlorophenoxy)-3-[4-[2-[[1-[4-(2-pyridyl)phenyl]ethylidene]aminoxy]ethoxy]phenyl]propionate (500 mg) obtained from Reference example 2 in ethanol (8 ml) was added an aqueous sodium hydroxide solution (1N, 1.79 ml), and the resulting solution was heated under reflux for 3 hours. The reaction solution was concentrated under reduced pressure, hydrochloric acid (1N) was added thereto to neutralize the solution, and then ethyl acetate was added thereto to extract the target compound. The separated organic layer was washed with a saturated aqueous sodium chloride solution, dried over anhydrous magnesium sulfate, and concentrated under reduced pressure. The obtained crude product was purified by chromatography on a silica gel column (eluant; methylene chloride/methanol=9/1) to afford the target compound (169 mg) as a colorless foam.

$^1$H-NMR (270 MHz, CDCl$_3$): δ (ppm) 2.17 (3H, s), 2.99 (2H, brs), 4.13 (2H, brs), 4.45 (3H, brs), 6.55–7.16 (9H, m), 7.66 (4H, d, J=8.5 Hz), 7.89 (2H, d, J=8.5 Hz), 8.63 (1H, d, J=5.0 Hz).

Reference Example 4

Ethyl 3-[4-[2-[[1-(4'-fluoro-4-biphenylyl)ethylidene]aminoxy]ethoxy]phenyl]-2-(4-fluorophenoxy)propionate The target compound (1.45 g) was obtained as a white powder by carrying out the reaction and the post-treatment according to Reference example 2 using ethyl 2-(4-fluorophenoxy)-3-(4-hydroxyphenyl)propionate (1.8 g) obtained from Reference example 25(b), sodium hydride (55%, 271 mg), and 2-[[1-(4'-fluoro-4-biphenylyl)ethylidene]aminoxy]ethyl methanesulfonate (2.14 g) obtained from Reference example 26(b).

mp: 103–105° C. $^1$H-NMR (270 MHz, CDCl$_3$): δ (ppm) 1.20 (3H, t, J=7.0 Hz), 2.26 (3H, s), 3.16 (2H, J=6.5 Hz), 4.17 (2H, q, J=7.0 Hz), 4.27 (2H, t, J=4.5 Hz), 4.54 (2H, t, J=4.5 Hz), 4.66 (1H, t, J=6.5 Hz), 6.74–6.79 (2H, m), 6.88–6.94 (4H, m), 7.13 (2H, t, J=8.5 Hz), 7.21 (2H, d, J=8.5 Hz), 7.52–7.59 (4H, m), 7.71 (2H, d, J=8.5 Hz).

Reference Example 5

3-[4-[2-[[1-(4'-Fluoro-4-biphenylyl)ethylidene]aminoxy]ethoxy]phenyl]-2-(4-fluorophenoxy)propionic acid The target compound (1.13 g) was obtained as colorless crystals by carrying out the reaction and the post-treatment according to Reference example 3 using ethyl 3-[4-[2-[[1-(4'-fluoro-4-biphenylyl)ethylidene]aminoxy]ethoxy]phenyl]-2-(4-fluorophenoxy)propionate (1.44 g) obtained from Reference example 4 and an aqueous sodium hydroxide solution (1N, 5.0 ml).

mp: 109–110° C. $^1$H-NMR (270 MHz, CDCl$_3$): δ (ppm) 2.25 (3H, s), 3.18–3.21 (2H, m), 4.27 (2H, t, J=5.0 Hz), 4.54 (2H, t, J=5.0 Hz), 4.72 (1H, t, J=5.5 Hz), 6.75–6.80 (2H, m), 6.88–6.89 (4H, m), 7.13 (2H, t, J=8.5 Hz), 7.21 (2H, d, J=8.5 Hz), 7.52–7.58 (4H, m), 7.70 (2H, d, J=8.5 Hz).

Reference Example 6

2-Trimethylsilylethyl (S)-3-[4-[2-[[1-(4-biphenylyl)ethylidene]aminoxy]ethoxy]phenyl]-2-(4-methylphenoxy)propionate To a solution of 2-[[1-(4-biphenylyl)ethylidene]aminoxy]ethanol (288 mg) obtained from Reference example 3(b) of WO 97/37970 (EP 916651A), 2-trimethylsilylethyl (S)-3-(4-hydroxyphenyl)-2-(4-methylphenoxy)propionate (280 mg) obtained from Reference example 20(e), and triphenylphosphine (296 mg) in toluene (10 ml) was added dropwise at 0° C. diisopropyl azodicarboxylate (40% toluene solution (0.61 ml)). After completion of the dropwise addition, the reaction solution was stirred at room temperature for 16 hours. The reaction solvent was evaporated under reduced pressure, and the residue was purified by chromatography on a silica gel column (eluant; hexane/ethyl acetate=9/1) to afford the target compound (270 mg) as a colorless oil.

$^1$H-NMR (270 MHz, CDCl$_3$): δ (ppm) 0.01 (9H, s), 0.92 (2H, t, J=8.5 Hz), 2.24 (3H, s), 2.26 (3H, s), 3.14–3.17 (2H, m), 4.10–4.23 (2H, m), 4.27 (2H, t, J=5.0 Hz), 4.54 (2H, t, J=5.0 Hz), 4.66 (1H, t, J=6.5 Hz), 6.73 (2H, d, J=8.5 Hz), 6.89 (2H, d, J=8.5 Hz), 7.02 (2H, d, J=8.5 Hz), 7.21 (2H, d, J=8.5 Hz), 7.33–7.48 (3H, m), 7.58–7.62 (4H, m), 7.71 (2H, d, J=8.5 Hz).

Reference Example 7

(S)-3-[4-[2-[[1-(4-Biphenylyl)ethylidene]aminoxy]ethoxy]phenyl]-2-(4-methylphenoxy)propionic acid To a solution of 2-trimethylsilylethyl (S)-3-[4-[2-[[1-(4-biphenylyl)ethylidene]aminoxy]ethoxy]phenyl]-2-(4-methylphenoxy)propionate (270 mg) obtained from Reference example 6 in tetrahydrofuran (5 ml) was added a 1M solution of tetrabutylammonium fluoride in tetrahydrofuran (1.1 ml), and the reaction solution was stirred at room temperature for 1.5 hours. The reaction solution was concentrated under reduced pressure, then hydrochloric acid (1N) was added thereto to neutralize the reaction mixture, and the reaction product was extracted with ethyl acetate. The separated ethyl acetate layer was washed with a saturated aqueous sodium chloride solution, dried over anhydrous magnesium sulfate, and concentrated under reduced pressure. The resulting crystals were filtered off and washed with hexane to afford the target compound (210 mg) as colorless crystals.

mp: 128–130° C. $^1$H-NMR (270 MHz, CDCl$_3$): δ (ppm) 2.26 (6H, s), 3.21 (2H, d, J=6.5 Hz), 4.27 (2H, t, J=5.0 Hz), 4.54 (2H, t, J=5.0 Hz), 4.78 (1H, t, J=6.5 Hz), 6.75 (2H, d, J=8.5 Hz), 6.89 (2H, d, J=8.5 Hz), 7.05 (2H, d, J=8.5 Hz), 7.21 (2H, d, J=8.5 Hz), 7.31–7.48 (3H, m), 7.58–7.62 (4H, m), 7.71 (2H, d, J=8.5 Hz).

Reference Example 8

2-Trimethylsilylethyl (S)-2-(4-methylphenoxy)-3-[4-[2-[[1-[4-(2-pyridyl)phenyl]ethylidene]aminoxy]ethoxy]phenyl]propionate The target compound (2.20 g) was obtained as a colorless oil by carrying out the reaction and the post-treatment according to Reference example 6 using 2-[[1-[4-(2-pyridyl)phenyl]ethylidene]aminoxy]ethanol (1.65 g) obtained from Reference example 1(d) of WO 97/37970 (EP 916651A), 2-trimethylsilylethyl (S)-3-(4-hydroxyphenyl)-2-(4-methylphenoxy)propionate (1.60 g) obtained from Reference example 20(e), triphenylphosphine (1.69 g) and diisopropyl azodicarboxylate (40% toluene solution (3.47 ml)).

$^1$H-NMR (270 MHz, CDCl$_3$): δ (ppm) 0.00 (9H, s), 0.91 (2H, t, J=8.5 Hz), 2.24 (3H, s), 2.26 (3H, s), 3.14–3.17 (2H, m), 4.09–4.23 (2H, m), 4.26 (2H, t, J=5.0 Hz), 4.54 (2H, t, J=5.0 Hz), 4.64–4.68 (1H, m), 6.71 (2H, d, J=8.5 Hz), 6.87 (2H, d, J=8.5 Hz), 7.01 (2H, d, J=8.5 Hz), 7.19–7.28 (3H, m), 7.73–7.79 (4H, m), 8.00 (2H, d, J=8.5 Hz), 8.70 (1H, d, J=5.5 Hz).

Reference Example 9

(S)-2-(4-Methylphehoxy)-3-[4-[2-[[1-[4-(2-pyridyl)phenyl]ethylidene]aminoxy]ethoxy]phenyl]propionic acid The target compound (1.48 g) was obtained as colorless crystals by carrying out the reaction and the post-treatment according to Reference example 7 using 2-trimethylsilylethyl (S)-2-(4-methylphenoxy)-3-[4-[2-[[1-[4-(2-pyridyl)phenyl]ethylidene]aminoxy]ethoxy]phenyl]propionate (2.20 g) and a 1M solution of tetrabutylammonium fluoride in tetrahydrofuran (9.00 ml).

mp: 54–56° C. $^1$H-NMR (270 MHz, CDCl$_3$): δ (ppm) 2.25 (6H, s), 3.21 (2H, d, J=6.0 Hz), 4.29 (2H, t, J=4.5 Hz), 4.55 (2H, t, J=4.5 Hz), 4.78 (1H, t, J=6.0 Hz), 6.77 (2H, d, J=8.5 Hz), 6.88 (2H, d, J=8.5 Hz), 7.03 (2H, d, J=8.5 Hz), 7.21 (2H, d, J=8.5 Hz), 7.26–7.30 (1H, m), 7.69–7.83 (4H, m), 7.89 (2H, d, J=8.5 Hz), 8.72 (1H, d, J=5.0 Hz)

Reference Example 10

2-Trimethylsilylethyl (S)-3-[4-[2-[[1-(4-biphenylyl)ethylidene]aminoxy]ethoxy]phenyl]-2-(4-t-butylphenoxy)propionate The target compound (300 mg) was obtained as a pale yellow oil by carrying out the reaction and the post-treatment according to Reference example 6 using 2-[[1-(4-biphenylyl)ethylidene]aminoxy]ethanol (288 mg) obtained by the method of Reference example 3(b) of WO 97/37970 (EP 916651A), 2-trimethylsilylethyl (S)-2-(4-t-butylphenoxy)-3-(4-hydroxyphenyl)propionate (311 mg) obtained from Reference example 19(e), triphenylphosphine (296 mg) and diisopropyl azodicarboxylate (40% toluene solution (0.61 ml)).

$^1$H-NMR (270 MHz, CDCl$_3$): δ (ppm) 0.00 (9H, s), 0.92 (2H, t, J=8.5 Hz), 1.25 (9H, s), 2.25 (3H, s), 3.14–3.17 (2H, m), 4.21–4.28 (4H, m), 4.53 (2H, t, J=4.5 Hz), 4.67 (1H, dd, J=6.0, 7.5 Hz), 6.75 (2H, d, J=9.0 Hz), 6.88 (2H, d, J=8.5 Hz), 7.19–7.24 (4H, m), 7.32–7.48 (3H, m), 7.57–7.62 (4H, m), 7.71 (2H, d, J=8.5 Hz).

Reference Example 11

(S)-3-[4-[2-[[1-(4-Biphenylyl)ethylidene]aminoxy]ethoxy]phenyl]-2-(4-t-butylphenoxy)propionic acid The reaction was carried out according to Reference example 7 using 2-trimethylsilylethyl (S)-3-[4-[2-[[1-(4-biphenylyl)ethylidene]aminoxy]ethoxy]phenyl]-2-(4-t-butylphenoxy)propionate (300 mg) obtained from Reference example 10 and a 1M solution of tetrabutylammonium fluoride in tetrahydrofuran (1.20 ml). The resulting residue was purified by chromatography on a silica gel column (eluant; methylene chloride/methanol=24/1~19/1), and then the obtained compound was filtered off and washed with isopropyl ether and hexane to afford the target compound (170 mg) as colorless crystals.

mp: 141–143° C. $^1$H-NMR (270 MHz, CDCl$_3$): δ (ppm) 1.27 (9H, s), 2.26 (3H, s), 3.21 (2H, d, J=6.5 Hz), 4.27(2H, t, J=5.0 Hz), 4.54 (2H, t, J=5.0 Hz), 4.81 (1H, t, J=6.5 Hz), 6.79 (2H, d, J=9.0 Hz), 6.89 (2H, d, J=8.5 Hz), 7.21 (2H, d, J=8.5 Hz), 7.27 (2H, d, J=9.0 Hz), 7.33–7.48 (3H, m), 7.58–7.62 (4H, m), 7.72 (2H, d, J=8.5 Hz).

Reference Example 12

2-Trimethylsilylethyl (S)-2-(4-t-butylphenoxy)-3-[4-[2-[[1-[4-(2-pyridyl)phenyl]ethylidene]aminoxy]ethoxy]phenyl]propionate The target compound (310 mg) was obtained as a colorless oil by carrying out the reaction and the post-treatment according to Reference example 6 using 2-[[1-[4-(2-pyridyl)phenyl]ethylidene]aminoxy]ethanol (290 mg) obtained by the method of Reference example 1(d) of WO 97/37970 (EP 916651A), 2-trimethylsilylethyl (S)-2-(4-t-butylphenoxy)-3-(4-hydroxyphenyl)propionate (311 mg) obtained from Reference example 21(e), triphenylphosphine (296 mg) and diisopropyl azodicarboxylate (40% toluene solution (0.61 ml)).

$^1$H-NMR (270 MHz, CDCl$_3$): δ (ppm) 0.00 (9H, s), 0.92 (2H, t, J=8.5 Hz), 1.25 (9H, s), 2.26 (3H, s), 3.13–3.17 (2H, m), 4.15–4.28 (4H, m), 4.54 (2H, t, J=4.5 Hz), 4.64–4.69 (1H, m), 6.75 (2H, d, J=9.0 Hz), 6.88 (2H, d, J=8.5 Hz), 7.19–7.26 (5H, m), 7.72–7.76 (4H, m), 8.00 (2H, d, J=8.5 Hz), 8.69–8.71 (1H, m).

Reference Example 13

(S)-2-(4-t-Butylphenoxy)-3-[4-[2-[[1-[4-(2-pyridyl)phenyl]ethylidene]aminoxy]ethoxy]phenyl]propionic acid The reaction was carried out according to Reference example 7 using 2-trimethylsilylethyl (S)-2-(4-t-butylphenoxy)-3-[4-[2-[[1-[4-(2-pyridyl)phenyl]ethylidene]aminoxy]ethoxy]phenyl]propionate (310 mg) obtained from Reference example 12 and a 1M solution of tetrabutylammonium fluoride in tetrahydrofuran (1.7 ml). The resulting residue was purified by chromatography on a silica gel column (eluant; methylene chloride/methanol=24/1~19/1), and then the obtained compound was filtered off and washed with isopropyl ether and hexane to afford the target compound (180 mg) as colorless crystals.

mp: 148–150° C. $^1$H-NMR (270 MHz, CDCl$_3$) δ (ppm) 1.30 (9H, s), 2.31 (3H, s), 3.26 (2H, d, J=6.0 Hz), 4.34 (2H, t, J=5.0 Hz), 4.59 (2H, t, J=5.0 Hz), 4.84 (1H, t, J=6.0 Hz), 6.86 (2H, d, J=9.0 Hz), 6.93 (2H, d, J=8.5 Hz), 7.25–7.35 (5H, m), 7.74–7.88 (4H, m), 7.95 (2H, d, J=8.5 Hz), 8.76 (1H, d, J=4.5 Hz).

Reference Example 14

2-Trimethylsilylethyl (S)-3-[4-[2-[[1-(4-biphenylyl)ethylidene]aminoxy]ethoxy]phenyl]-2-(4-fluorophenoxy)propionate The target compound (88 mg) was obtained as a colorless oil by carrying out the reaction and the post-treatment according to Reference example 6 using 2-[[1-(4-biphenylyl)ethylidene]aminoxy]ethanol (83 mg) obtained by the method of Reference example 3(b) of WO 97/37970 (EP 916651A), 2-trimethylsilylethyl (S)-2-(4-fluorophenoxy)-3-(4-hydroxyphenyl)propionate (100 mg) obtained from Reference example 22(e), triphenylphosphine (86 mg) and diisopropyl azodicarboxylate (40% toluene solution (0.14 ml)).

$^1$H-NMR (270 MHz, CDCl$_3$): δ (ppm) 0.02 (9H, s), 0.92 (2H, dd, J=7.5, 9.5 Hz), 2.26 (3H, s), 3.16 (2H, d, J=6.5 Hz), 4.16–4.24 (2H, m), 4.28 (2H, t, J=5.0 Hz), 4.54 (2H, t, J=5.0 Hz), 4.63 (1H, t, J=6.5 Hz), 6.76 (2H, dd, J=4.0, 9.0 Hz), 6.90 (2H, d, J=8.5 Hz), 6.91 (2H, dd, J=8.5, 9.0 Hz), 7.21 (2H, d, J=8.5 Hz), 7.36 (1H, t, J=7.0 Hz), 7.45 (2H, dd, J=7.0, 8.5 Hz), 7.60 (2H, d, J=8.5 Hz), 7.61 (2H, d, J=8.5 Hz), 7.73 (2H, d, J=8.5 Hz).

Reference Example 15

(S)-3-[4-[2-[[1-(4-Biphenylyl)ethylidene]aminoxy]ethoxy]phenyl]-2-(4-fluorophenoxy)propionic acid The target compound (568 mg) was obtained as colorless crystals by carrying out the reaction and the post-treatment according to Reference example 7 using 2-trimethylsilylethyl (S)-3-[4-[2-[[1-(4-biphenylyl)ethylidene]aminoxy]ethoxy]phenyl]-2-(4-fluorophenoxy)propionate (938 mg) obtained from Reference example 14 and a 1M solution of tetrabutylammonium fluoride in tetrahedrofuran (3.8 ml).

mp: 106–107° C. $^1$H-NMR (270 MHz, CDCl$_3$): δ (ppm) 2.26 (3H, s), 3.20 (1H, d, J=5.0 Hz), 3.21 (1H, d, J=7.5 Hz), 4.28 (2H, t, J=5.0 Hz), 4.54 (2H, t, J=5.0 Hz), 4.73 (1H, dd, J=5.0, 7.5 Hz), 6.79 (2H, dd, J=4.0, 9.0 Hz), 6.90 (2H, d, J=8.5 Hz), 6.92 (2H, dd, J=8.0, 9.0 Hz), 7.22 (2H, d, J=8.5 Hz), 7.36 (1H, t, J=7.0 Hz), 7.45 (2H, dd, J=7.0, 8.5 Hz), 7.60 (2H, d, J=8.5 Hz), 7.61 (2H, d, J=8.5 Hz), 7.72 (2H, d, J=8.5 Hz).

Reference Example 16

2-Trimethylsilylethyl (S)-2-(4-fluorophenoxy)-3-[4-[2-[[1-(4'-methoxy-4-biphenylyl)ethylidene]aminoxy]ethoxy]phenyl]propionate The target compound (438 mg) was obtained as a colorless oil by carrying out the reaction and the post-treatment according to Reference example 6 using 2-[1-(4'-methoxy-4-biphenylyl)ethylidene]aminoxy]ethanol (325 mg) obtained from Reference example 23(b), 2-trimethylsilylethyl (S)-2-(4-fluorophenoxy)-3-(4-hydroxyphenyl)propionate (286 mg) obtained from Reference example 22(e), triphenylphosphine (299 mg) and diisopropyl azodicarboxylate (40% toluene solution (0.61 ml)).

$^1$H-NMR (270 MHz, CDCl$_3$): δ (ppm) 0.01 (9H, s), 0.91 (2H, dd, J=7.5, 10.0 Hz), 2.25 (3H, s), 3.15 (2H, d, J=6.5 Hz), 3.85 (3H, s), 4.14–4.23 (2H, m), 4.26 (2H, t, J=5.0 Hz), 4.53 (2H, t, J=5.0 Hz), 4.62 (1H, t, J=6.5 Hz), 6.75 (2H, dd, J=4.5, 9.0 Hz), 6.89 (2H, d, J=8.5 Hz), 6.90 (2H, dd, J=8.5, 9.0 Hz), 6.97 (2H, d, J=8.5 Hz), 7.20 (2H, d, J=8.5 Hz), 7.53 (2H, d, J=8.5 Hz), 7.54 (2H, d, J=8.5 Hz), 7.68 (2H, d, J=8.5 Hz).

Reference Example 17

(S)-2-(4-Fluorophenoxy)-3-[4-[2-[[1-(4'-methoxy-4-biphenylyl)ethylidene]aminoxy]ethoxy]phenyl]propionic acid The target compound (243 mg) was obtained as colorless crystals by carrying out the reaction and the post-treatment according to Reference example 7 using 2-trimethylsilylethyl (S)-2-(4-fluorophenoxy)-3-[4-[2-[[1-(4'-methoxy-4-biphenylyl)ethylidene]aminoxy]ethoxy]phenyl]propionate (438 mg) obtained from Reference example 16 and a 1M solution of tetrabutylammonium fluoride in tetrahydrofuran (1.7 ml).

mp: 118–120° C. $^1$H-NMR (270 MHz, CDCl$_3$): δ (ppm) 2.25 (3H, s), 3.20 (1H, d, J=7.0 Hz), 3.21 (1H, d, J=4.0 Hz), 3.86 (3H, s), 4.27 (2H, t, J=5.0 Hz), 4.53 (2H, t, J=5.0 Hz), 4.73 (1H, dd, J=4.0, 7.0 Hz), 6.78 (2H, dd, J=4.0, 9.0 Hz), 6.90 (2H, d, J=8.5 Hz), 6.92 (2H, dd, J=8.0, 9.0 Hz), 6.98 (2H, d, J=8.5 Hz), 7.21 (2H, d, J=8.5 Hz), 7.54 (2H, d, J=8.5 Hz), 7.55 (2H, d, J=8.5 Hz), 7.68 (2H, d, J=8.5 Hz).

Reference Example 18

2-Trimethylsilylethyl (S)-2-(4-fluorophenoxy)-3-[4-[2-[[1-[4-(2-pyridyl)phenyl]ethylidene]aminoxy]ethoxy]phenyl]propionate The target compound (531 mg) was obtained as a colorless oil by carrying out the reaction and the post-treatment according to-Reference example 6 using 2-[[1-[4-(2-pyridyl)phenyl]ethylidene]aminoxy]ethanol (520 mg) obtained by the method of Reference example 1(d) of WO 97/37970(EP 916651A), 2-trimethylsilylethyl (S)-2-(4-fluorophenoxy)-3-(4-hydroxyphenyl)propionate (380 mg) obtained from Reference example 22(e), triphenylphosphine (537 mg) and diisopropyl azodicarboxylate (40% toluene solution (0.94 ml)).

$^1$H-NMR (270 MHz, CDCl$_3$): δ (ppm) 0.01 (9H, s), 0.92 (2H, dd, J=7.5, 10.0 Hz), 2.26 (3H, s), 3.15 (2H, d, J=6.5 Hz), 4.15–4.23 (2H, m), 4.28 (2H, t, J=5.0 Hz), 4.54 (2H, t, J=5.0 Hz), 4.63 (1H, t, J=6.5 Hz), 6.76 (2H, dd, J=4.0, 9.0 Hz), 6.90 (2H, d, J=8.5 Hz), 6.91 (2H, dd, J=8.5, 9.0 Hz), 7.21 (2H, d, J=8.5 Hz), 7.22–7.27 (1H, m), 7.74–7.77 (4H, m), 8.00 (2H, d, J=8.5 Hz), 8.71 (1H, d, J=5.0 Hz).

Reference Example 19

(S)-2-(4-Fluorophenoxy)-3-[4-[2-[[1-[4-(2-pyridyl)phenyl]ethylidene]aminoxy]ethoxy]phenyl]propionic acid The target compound (1.16 g) was obtained as colorless crystals by carrying out the reaction and the post-treatment according to Reference example 7 using 2-trimethylsilylethyl (S)-2-(4-fluorophenoxy)-3-[4-[2-[[1-[4-(2-pyridyl)phenyl]ethylidene]aminoxy]ethoxy]phenyl]propionate (1.84 g) obtained from Reference example 18 and a 1M solution of tetrabutylammonium fluoride in tetrahydrofuran (7.5 ml).

mp: 88–90° C. $^1$H-NMR (270 MHz, CDCl$_3$): δ (ppm) 2.25 (3H, s), 3.20 (1H, d, J=7.0 Hz), 3.21 (1H, d, J=5.5 Hz), 4.30 (2H, t, J=5.0 Hz), 4.55 (2H, t, J=5.0 Hz), 4.72 (1H, dd, J=5.5, 7.0 Hz), 6.81 (2H, dd, J=4.5, 9.0 Hz), 6.89 (2H, d, J=8.5 Hz), 6.91 (2H, dd, J=8.5, 9.0 Hz), 7.22 (2H, d, J=8.5 Hz), 7.27–7.32 (1H, m), 7.69 (2H, d, J=8.5 Hz), 7.72 (1H, d, J=7.5 Hz), 7.80 (1H, dd, J=2.0, 7.5 Hz), 7.86 (2H, d, J=8.5 Hz), 8.72 (1H, d, J=5.0 Hz).

Reference Example 20

2-Trimethylsilylethyl (S)-3-(4-hydroxyphenyl)-2-(4-methylphenoxy)propionate

Reference Example 20(a)

(S)-4-Benzyl-3-[(4-methylphenoxy)acetyl]oxazolidin-2-one

Oxalyl chloride (8.83 ml) and N,N-dimethylformamide (3 drops) were added at room temperature to a solution of 4-methylphenoxyacetic acid (6.73 g) in dichloromethane (70 ml), and the reaction mixture was stirred for 1.5 hours. The reaction solution was concentrated under reduced pressure, then the resulting acidic gas was removed as the toluene azeotrope, and the product was dried under reduced pressure to give 4-methylphenoxyacetyl chloride. A 1.61N solution of n-butyl lithium in hexane (25.2 ml) was added dropwise at −78° C. to a solution of (S)-4-benzyl-2-oxazolidinone (7.08 g) in tetrahydrofuran (70-ml), and after the completion of the dropwise addition, the reaction mixture was stirred at −78° C. for 30 minutes. To this resulting solution was added at −78° C. a solution of 4-methylphenoxyacetyl chloride obtained above in tetrahydrofuran (70 ml) followed by stirring at 0° C. for 1 hour. The resulting reaction mixture was partitioned between ethyl acetate and water, and the ethyl acetate layer was washed successively with a 1N aqueous solution of hydrochloric acid, a saturated aqueous sodium hydrogencarbonate solution and a saturated aqueous sodium chloride solution, dried over anhydrous magnesium sulfate, and concentrated under reduced pressure. The obtained residue was purified by chromatography on a silica gel column (eluant; hexane/ethyl acetate =3/1~1/1) to afford the target compound (9.00 g) as a colorless oil.

$^1$H-NMR (270 MHz, CDCl$_3$): δ (ppm) 2.30 (3H, s), 2.84 (1H, dd, J=9.5, 13.5 Hz), 3.36 (1H, dd, J=3.0, 13.5 Hz), 4.25–4.37 (2H, m), 4.68–4.76 (1H, m), 5.22 (2H, s), 6.88 (2H, d, J=8.5 Hz), 7.11 (2H, d, J=8.5 Hz), 7.20–7.38 (5H, m).

Reference Example 20(b)

(S)-4-Benzyl-3-[(2S,3R)-3-(4-benzyloxyphenyl)-3-hydroxy-2-(4-methylphenoxy)propionyl]oxazolidin-2-one A 1M solution of dibutylboron triflate in dichloromethane (33.2 ml) and triethylamine (5.12 ml) were added at 0° C. to a solution of (S)-4-benzyl-3-[(4-methylphenoxy)acetyl]oxazolidin-2-one (9.00 g) obtained from Reference example 20(a) in dichloromethane (90 ml), and the mixture was stirred at 0° C. for 1 hour. A solution of 4-benzyloxybenzaldehyde (6.46 g) in dichloromethane (6 ml) was added dropwise at −78° C. to the reaction solution, and then the reaction solution was stirred at 0° C. for 2 hours. A mixed solution (20 ml) of a saturated aqueous sodium chloride solution and methanol (1:1) and a mixed solution (100 ml) of an aqueous solution of hydrogen peroxide (31%) and methanol (2:1) were added thereto, and the resulting reaction solution was stirred for 1 hour. After the methanol was evaporated under reduced pressure, the residue was extracted with ethyl acetate. The ethyl acetate layer was washed successively with an aqueous solution of hydrochloric acid (1N), a saturated aqueous sodium hydrogencarbonate solution and a saturated aqueous sodium chloride solution, dried over anhydrous magnesium sulfate, and concentrated under reduced pressure. The residue was purified by chromatography on a silica gel column (eluant; hexane/ethyl acetate=3/1~1/1) to afford the target compound (9.80 g) as a foam.

$^1$H-NMR (270 MHz, CDCl$_3$): δ (ppm) 2.28 (3H, s), 2.71 (1H, dd, J=9.0, 13.5 Hz), 3.04–3.10 (2H, m), 3.57 (1H, t, J=8.5 Hz), 3.99 (1H, dd, J=2.0, 8.5 Hz), 4.22–4.28 (1H, m), 5.05–5.09 (3H, m), 6.18 (1H, d, J=6.0 Hz), 6.89 (2H, d, J=8.5 Hz), 6.95 (2H, d, J=8.5 Hz), 7.04–7.10 (4H, m), 7.25–7.44 (10H, m).

Reference Example 20(c)

(S)-4-Benzyl-3-[(2S,3R)-3-hydroxy-3-(4-hydroxyphenyl)-2-(4-methylphenoxy)propionyl]oxazolidin-2-one To a solution of (S)-4-benzyl-3-[(2S,3R)-3-(4-benzyloxyphenyl)-3-hydroxy-2-(4-methylphenoxy)propionyl]oxazolidin-2-one (9.80 g) obtained from Reference example 20(b) in ethanol (150 ml) was added 5% palladium-charcoal (1.00 g), and the reaction solution was stirred at 50° C. for 4 hours in an atmosphere of hydrogen. After the catalyst was removed by filtration, the filtrate was concentrated under reduced pressure. Water was added to the residue, and the resulting solution was extracted with ethyl acetate. The ethyl acetate layer was dried over anhydrous magnesium sulfate, and then the target compound (9.10 g) was obtained as a foam.

$^1$H-NMR (270 MHz, CDCl$_3$): δ (ppm) 2.28(3H, s), 2.74 (1H, dd, J=9.0, 13.5 Hz), 3.04–3.10 (2H, m), 3.74 (1H, t, J=8.5 Hz), 4.04 (1H, dd, J=1.5, 8.5 Hz), 4.28–4.34 (1H, m), 5.08, (1H, t, J=5.5 Hz), 5.15 (1H, s), 6.17 (1H, d, J=5.5 Hz), 6.79 (2H, d, J=8.5 Hz), 6.88 (2H, d, J=8.5 Hz), 7.04–7.10 (4H, m), 7.25–7.38 (5H, m).

Reference Example 20(d)

(S)-4-Benzyl-3-[(S)-3-(4-hydroxyphenyl)-2-(4-methylphenoxy)propionyl]oxazolidin-2-one Triethylsilane (24.0 ml) was added at room temperature to a solution of (S)-4-benzyl-3-[(2S,3R)-3-hydroxy-3-(4-hydroxyphenyl)-2-(4-methylphenoxy)propionyl]oxazolidin-2-one (8.15 g) obtained from Reference example 20(c) in trifluoroacetic acid (90 ml), then the mixture was stirred for 18 hours and concentrated under reduced pressure. The residue was partitioned between ethyl acetate and water. The ethyl acetate layer was washed successively with a saturated aqueous sodium hydrogencarbonate solution, a 1N aqueous solution of hydrochloric acid and a saturated aqueous sodium chloride solution, dried over anhydrous magnesium sulfate, and concentrated under reduced pressure. The obtained crystals were filtered off and washed with a mixed solvent of isopropyl ether and hexane to give the target compound (6.70 g) as colorless crystals.

mp: 135–136° C. $^1$H-NMR (270 MHz, CDCl$_3$): δ (ppm) 2.26 (3H, s), 2.77 (1H, dd, J=9.5, 13.5 Hz), 3.08–3.23 (3H, m), 4.01 (1H, t, J=8.5 Hz), 4.15 (1H, dd, J=2.0, 8.5 Hz), 4.46–4.55 (1H, m), 4.80–4.88 (1H, m), 6.09 (1H, dd, J=6.0, 8.0 Hz), 6.75 (2H, d, J=8.5 Hz), 6.80 (2H, d, J=8.5 Hz), 7.05 (2H, d, J=8.5 Hz), 7.10–7.15 (2H, m), 7.21–7.33 (5H, m).

Reference Example 20(e)

2-Trimethylsilylethyl (S)-3-(4-hydroxyphenyl)-2-(4-methylphenoxy)propionate

To a suspension of (S)-4-benzyl-3-[(S)-3-(4-hydroxyphenyl)-2-(4-methylphenoxy)propionyl]oxazolidin-2-one (6.50 g) obtained from Reference example 20(d) in methanol (80 ml) was added dropwise a mixed solution of an aqueous solution of lithium hydroxide (1N, 37.7 ml) and an aqueous solution of hydrogen peroxide (31%, 4.14 ml). The reaction solution was stirred for 1 hour at room temperature, then an aqueous solution (20 ml) of sodium hydrosulfite (6.56 g) was added thereto followed by stirring for 1 hour, and the resulting reaction solution was concentrated under reduced pressure. To the residue was added an aqueous solution of sodium hydroxide (1N), then the resulting alkaline solution was washed with dichloromethane and acidified by addition of hydrochloric acid. Ethyl acetate was added thereto, and the resulting solution was stirred and partitioned between ethyl acetate and water. The separated ethyl acetate layer was dried over anhydrous magnesium sulfate, and concentrated under reduced pressure. The residue was crystallized by addition of isopropyl ether and hexane to yield (S)-3-(4-hydroxyphenyl)-2-(4-methylphenoxy)propionic acid (3.38 g) as a white powder.

Oxalyl chloride (5.21 ml) and N,N-dimethylformamide (5 drops) were added at room temperature to a suspension of the above carboxylic acid (3.25 g) in dichloromethane (40 ml), and the mixture was stirred for 1 hour. The reaction solution was concentrated under reduced pressure, and then the remaining acidic gas was removed as the toluene azeotrope to remove the excess reagent. To a solution of the residue in dichloromethane (40 ml) was added 2-trimethylsilylethanol (8.55 ml), and the resulting solution was stirred for 15 hours at room temperature. Triethylamine (4.16 ml) and 4-N,N-dimethylaminopyridine (146 mg) were added to the mixture solution followed by stirring for 1 hour at room temperature. The reaction solution was concentrated under reduced pressure, and the residue was partitioned between ethyl acetate and water. The ethyl acetate layer was washed with a saturated aqueous sodium chloride solution, dried over anhydrous magnesium sulfate, and concentrated under reduced pressure. The residue was purified by chromatography on a silica gel column (eluant; hexane/ethyl acetate=6/1~4/1) to afford the target compound (3.43 g) as colorless crystals.

mp: 94–95° C. $^1$H-NMR (270 MHz, CDCl$_3$): δ (ppm) 0.02 (9H, s), 0.92 (2H, t, J=8.5 Hz), 2.25 (3H, s), 3.13–3.19 (2H, m), 4.10–4.28 (2H, m), 4.66 (1H, dd, J=6.0, 7.0 Hz), 4.77 (1H, s), 6.73 (2H, d, J=8.5 Hz), 6.75 (2H, d, J=8.5 Hz), 7.02 (2H, d, J=8.5 Hz), 7.16 (2H, d, J=8.5 Hz).

Reference Example 21

2-Trimethylsilylethyl (S)-2-(4-t-butylphenoxy)-3-(4-hydroxyphenyl)propionate

Reference Example 21(a)

(S)-4-Benzyl-3-[(4-t-butylphenoxy)acetyl]oxazolidin-2-one

The target compound (28.3 g) was obtained as colorless crystals by carrying out the reaction and the post-treatment according to Reference example 20(a) using 4-t-butylphenoxyacetic acid (17.0 g), oxalyl chloride (17.8 ml), (S)-4-benzyl-2-oxazolidinone (14.2 g) and a solution of n-butyl lithium in hexane (1.61N, 50.4 ml).

mp: 107–108° C. $^1$H-NMR (270 MHz, CDCl$_3$) δ (ppm) 1.30 (9H, s), 2.85 (1H, dd, J=9.5, 13.5 Hz), 3.36 (1H, dd, J=3.0, 13.5 Hz), 4.25–4.37 (2H, m), 4.68–4.77 (1H, m), 5.22 (2H, s), 6.91 (2H, d, J=8.5 Hz), 7.20–7.38 (7H, m).

Reference Example 21(b)

(S)-4-Benzyl-3-[(2S,3R)-3-(4-benzyloxyphenyl)-2-(4-t-butylphenoxy)-3-hydroxypropionyl]oxazolidin-2-one The target compound (30.0 g) was obtained as a colorless oil by carrying out the reaction and the post-treatment according to Reference example 20(b) using (S)-4-benzyl-3-[(4-t-butylphenoxy)acetyl]oxazolidin-2-one (28.2 g) obtained from Reference example 21(a), a solution of dibutylboron triflate in dichloromethane (1M, 92.1 ml), triethylamine (13.9 ml) and 4-benzyloxybenzaldehyde (17.9 g).

$^1$H-NMR (270 MHz, CDCl$_3$): δ (ppm) 1.28 (9H, s), 2.73 (1H, dd, J=9.0, 13.5 Hz), 3.03–3.12 (2H, m), 3.58 (1H, t, J=8.5 Hz), 3.97 (1H, dd, J=1.5, 8.5 Hz), 4.23–4.29 (1H, m), 5.05 (2H, s), 5.08 (1H, t, J=5.5 Hz), 6.19 (1H, d, J=5.5 Hz), 6.92 (2H, d, J=8.5 Hz), 6.95 (2H, d, J=8.5 Hz), 7.06–7.08 (2H, m), 7.25–7.40 (12H, m).

Reference Example 21(c)

(S)-4-Benzyl-3-[(2S,3R)-2-(4-t-butylphenoxy)-3-hydroxy-3-(4-hydroxyphenyl)propionyl]oxazolidin-2-one The target compound (27.0 g) was obtained as a foam by carrying out the reaction and the post-treatment according to Reference example 20(c) using (S)-4-benzyl-3-[((2S,3R)-3-(4-benzyloxyphenyl)-2-(4-t-butylphenoxy)-3-hydroxypropionyl]oxazolidin-2-one (30.0 g) obtained from Reference example 21(b) and palladium-charcoal (5%, 3.00 g).

$^1$H-NMR (270 MHz, CDCl$_3$): δ (ppm) 2.05 (9H, s), 2.76 (1H, dd, J=9.0, 13.5 Hz), 3.07–3.13 (2H, m), 3.75 (1H, t, J=8.5 Hz), 4.05 (1H, dd, J=2.0, 8.5 Hz), 4.29–4.34 (1H, m), 5.08, (1H, t, J=5.5 Hz), 5.32 (1H, s), 6.18 (1H, d, J=5.5 Hz), 6.80 (2H, d, J=8.5 Hz), 6.92 (2H, d, J=8.5 Hz), 7.06–7.09 (2H, m), 7.25–7.36 (7H, m).

Reference Example 21(d)

(S)-4-Benzyl-3-[(S)-2-(4-t-butylphenoxy)-3-(4-hydroxyphenyl)propionyl]oxazolidin-2-one The target compound (18.2 g) was obtained as colorless crystals by carrying out the reaction and the post-treatment according to Reference example 20(d) using (S)-4-benzyl-3-[(2S,3R)-2-(4-t-butylphenoxy)-3-hydroxy-3-(4-hydroxyphenyl)propionyl]oxazolidin-2-one (25.3 g) obtained from Reference example 21(c) and triethylsilane (66 ml).

mp: 160–161° C. $^1$H-NMR (270 MHz, CDCl$_3$): δ (ppm) 1.26 (9H, s), 2.79 (1H, dd, J=9.5, 13.5 Hz), 3.08–3.23 (3H, m), 4.03 (1H, t, J=8.5 Hz), 4.17 (1H, dd, J=2.5, 8.5 Hz), 4.48–4.56 (1H, m), 4.77 (1H, brs), 6.08 (1H, dd, J=5.5, 8.0 Hz), 6.75 (2H, d, J=8.5 Hz), 6.83 (2H, d, J=8.5 Hz), 7.11–7.14 (2H, m), 7.22–7.32 (7H, m).

Reference Example 21(e)

2-Trimethylsilylethyl (S)-2-(4-t-butylphenoxy)-3-(4-hydroxyphenyl)propionate

A white powder of (S)-2-(4-t-butylphenoxy)-3-(4-hydroxyphenyl)propionic acid (13.4 g) was obtained by carrying out the reaction and the post-treatment according to Reference example 20(e) using (S)-4-benzyl-3-[(S)-2-(4-t-butylphenoxy)-3-(4-hydroxyphenyl)propionyl]oxazolidin-2-one (24.3 g) obtained from Reference example 21(d), an aqueous solution of lithium hydroxide (1N, 128 ml) and an aqueous solution of hydrogen peroxide (31%, 14.1 ml).

The target compound (16.0 g) was obtained as colorless crystals by carrying out the reaction and the post-treatment according to Reference example 20(e) using the above carboxylic acid (13.3 g), oxalyl chloride (18.45 ml) and 2-trimethylsilylethanol (30.3 ml).

mp: 71–72° C. $^1$H-NMR (270 MHz, CDCl$_3$): δ (ppm) 0.06 (9H, s), 0.93 (2H, t, J=8.5 Hz), 1.31 (9H, s), 3.18–3.21 (2H, m), 4.18–4.33 (2H, m), 4.69–4.73 (2H, m), 6.79 (2H, d, J=8.5 Hz), 6.80 (2H, d, J=8.5 Hz), 7.21 (2H, d, J=8.5 Hz), 7.28 (2H, d, J=8.5 Hz).

Reference Example 22

2-Trimethylsilylethyl (S)-2-(4-fluorophenoxy)-3-(4-hydroxyphenyl)propionate

Reference Example 22(a)

(S)-4-Benzyl-3-[(4-fluorophenoxy)acetyl]oxazolidin-2-one

The target compound (2.76 g) was obtained as colorless crystals by carrying out the reaction and the post-treatment according to Reference example 20(a) using 4-fluorophenoxyacetic acid (1.70 g), oxalyl chloride (2.18 ml), (S)-4-benzyl-2-oxazolidinone (1.77 g) and a solution of n-butyl lithium in hexane (1.61N, 7.14 ml).

mp: 113–115° C. $^1$H-NMR (270 MHz, CDCl$_3$): δ (ppm) 2.85 (1H, dd, J=9.5, 13.5 Hz), 3.36 (1H, dd, J=3.0, 13.5 Hz), 4.26–4.38 (2H, m), 4.68–4.77 (1H, m), 5.21 (2H, s), 6.90–7.04 (4H, m), 7.20–7.38 (5H, m).

Reference Example 22(b)

(S)-4-Benzyl-3-[(2S,3R)-3-(4-benzyloxyphenyl)-2-(4-fluorophenoxy)-3-hydroxypropionyl]oxazolidin-2-one The target compound (2.68 g) was obtained as a foam by carrying out the reaction and the post-treatment according to Reference example 20(b) using (S)-4-benzyl-3-[(4-fluorophenoxy)acetyl]oxazolidin-2-one (1.96 g) obtained from Reference example 22(a), a solution of dibutylboron triflate in dichloromethane (1M, 7.14 ml), triethylamine (1.08 ml) and 4-benzyloxybenzaldehyde (1.39 g).

$^1$H-NMR (270 MHz, CDCl$_3$): δ (ppm) 2.72 (1H, dd, J=9.0, 13.5 Hz), 2.97–3.11 (1H, m), 3.05 (1H, dd, J=3.0, 13.5 Hz), 3.57 (1H, t, J=8.5 Hz), 3.97 (1H, dd, J=2.0, 8.5 Hz), 4.21–4.27(1H, m), 5.03–5.13 (1H, m), 5.05 (2H, s), 6.16 (1H, d, J=5.5 Hz), 6.85–7.06 (6H, m), 7.07–7.12 (2H, m), 7.25–7.43 (10H, m).

Reference Example 22(c)

(S)-4-Benzyl-3-[(2S,3R)-2-(4-fluorophenoxy)-3-hydroxy-3-(4-hydroxyphenyl)propionyl]oxazolidin-2-one The target compound (1.94 g) was obtained as a foam by carrying out the reaction and the post-treatment according to Reference example 20(c) using (S)-4-benzyl-3-[(2S,3R)-3-(4-benzyloxyphenyl)-2-(4-fluorophenoxy)-3-hydroxypropionyl]oxazolidin-2-one (2.33 g) obtained from Reference example 22(b) and palladium-charcoal (5%, 490 mg).

$^1$H-NMR (270 MHz, CDCl$_3$): δ (ppm) 2.75 (1H, dd, J=9.0, 13.5 Hz), 3.03–3.10 (1H, m), 3.07 (1H, dd, J=3.0, 13.5 Hz), 3.75 (1H, t, J=8.5 Hz), 4.06 (1H, dd, J=2.0, 8.5 Hz), 4.26–4.34 (1H, m), 5.08, (1H, dd, J=4.5, 5.5 Hz), 6.16 (1H, d, J=5.5 Hz), 6.81 (2H, d, J=8.5 Hz), 6.89–7.01 (4H, m), 7.02–7.10 (2H, m), 7.24–7.30 (5H, m), 7.34 (2H, d, J=8.5 Hz).

Reference Example 22(d)

(S)-4-Benzyl-3-[(S)-2-(4-fluorophenoxy)-3-(4-hydroxyphenyl)propionyl]oxazolidin-2-one The target compound (1.21 g) was obtained as colorless crystals by carrying out the reaction and the post-treatment according to Reference example 20(d) using (S)-4-benzyl-3-[(2S,3R)-2-(4-fluorophenoxy)-3-hydroxy-3-(4-hydroxyphenyl)propionyl]oxazolidin-2-one (1.89 g) obtained from Reference example 22(c) and triethylsilane (5.4 ml).

mp: 137–138° C. $^1$H-NMR (270 MHz, CDCl$_3$): δ (ppm) 2.77 (1H, dd, J=9.0, 13.5 Hz), 3.08–3.20 (3H, m), 4.02 (1H, t, J=8.5 Hz), 4.17 (1H, dd, J=2.5, 8.5 Hz), 4.46–4.54 (1H, m), 4.82–4.92 (1H, m), 6.06 (1H, dd, J=6.0, 7.5 Hz), 6.76 (2H, d, J=8.5 Hz), 6.86 (2H, dd, J=4.5, 9.0 Hz), 6.94 (2H, dd, J=8.0, 9.0 Hz), 7.09–7.12 (2H, m), 7.22 (2H, d, J=8.5 Hz), 7.26–7.30 (5H, m).

Reference Example 22(e)

2-Trimethylsilylethyl (S)-2-(4-fluorophenoxy)-3-(4-hydroxyphenyl)propionate

A white powder of (S)-2-(4-fluorophenoxy)-3-(4-hydroxyphenyl)propionic acid (2.31 g) was obtained by carrying out the reaction and the post-treatment according to Reference example 20(e) using (S)-4-benzyl-3-[(S)-2-(4-fluorophenoxy)-3-(4-hydroxyphenyl)propionyl]oxazolidin-2-one (4.20 g) obtained from Reference example 22(d), an aqueous solution of lithium hydroxide (1N, 24.1 ml) and an aqueous solution of hydrogen peroxide (31%, 2.64 ml).

The target compound (1.81 g) was obtained as colorless crystals by carrying out the reaction and the post-treatment according to Reference example 20(e) using the above carboxylic acid (2.30 g), oxalyl chloride (1.80 ml) and 2-trimethylsilylethanol (15.96 ml).

mp: 99–100° C. $^1$H-NMR (270 MHz, CDCl$_3$): δ (ppm) 0.02 (9H, s), 0.93 (2H, dd, J=7.5, 10.0 Hz), 3.15 (2H, d, J=6.5 Hz), 4.16–4.24 (2H, m), 4.62 (1H, t, J=6.5 Hz), 4.82 (1H, brs), 6.74–6.79 (4H, m), 6.91 (2H, dd, J=8.5, 9.0 Hz); 7.16 (2H, d, J=8.5 Hz).

Reference Example 23

2-[[1-(4'-Methoxy-4-biphenylyl)ethylidene]aminoxy]ethanol

Reference Example 23(a)

4'-(4-Methoxyphenyl)acetophenone oxime

To a solution of potassium hydroxide (2.9 g) in a mixture of methanol (40 ml)/water (8 ml) was added hydroxylamine hydrochloride (3.07 g), then the solution was stirred at 50° C. for 30 minutes, and 4-(4-methoxyphenyl)acetophenone (5.0 g) was added thereto. The reaction solution was stirred at 50° C. for 7 hours, and then potassium hydroxide (2.9 g) and hydroxylamine hydrochloride (3.07 g) were added thereto. The reaction solution was further stirred at 50° C. for 65 hours and then concentrated under reduced pressure. Ethyl acetate and water were added to the residue to yield crystals, which were filtered off and washed successively with water and ethyl acetate. The obtained crystals were further washed with isopropyl ether to afford the target compound (4.05 g) as colorless crystals.

mp: 82–84° C. $^1$H-NMR (270 MHz, DMSO-d$_6$): δ (ppm) 2.18 (3H, s), 3.80 (3H, s), 7.03 (2H, d, J=8.5 Hz), 7.64 (4H, d, J=8.0 Hz), 7.71 (2H, d, J=8.5 Hz).

Reference Example 23(b)

2-[[1-(4'-Methoxy-4-biphenylyl)ethylidene]aminoxy]ethanol

To a solution of 2-(2-bromoethoxy)tetrahydropyran (494 mg) and 4'-(4-methoxyphenyl)acetophenone oxime (380 mg) obtained from Reference example 23(a) in N,N-dimethylacetamide (10 ml) was added potassium carbonate (660 mg), and the mixture was stirred at 80° C. for 16 hours. The reaction solution was partitioned between ethyl acetate and water. The ethyl acetate layer was dried over anhydrous magnesium sulfate and then concentrated under reduced pressure. The residue was purified by chromatography on a silica gel column (eluant; hexane/ethyl acetate=5/1) to afford 4'-(4-methoxyphenyl)acetophenone oxime O-2-[(tetrahydropyran-2-yl)oxy]ethylether (590 mg) as a white solid.

To a solution of 4'-(4-methoxyphenyl)acetophenone oxime O-2-[(tetrahydropyran-2-yl)oxy]ethylether (561 mg) in methanol (30 ml) was added p-toluenesulfonic acid monohydrate (290 mg), then the mixture was stirred for 2 hours at room temperature and concentrated under reduced pressure. The residue was dissolved in ethyl acetate, and then the solution was washed with a saturated aqueous sodium hydrogencarbonate solution, dried over anhydrous magnesium sulfate and concentrated under reduced pressure. The obtained crystals were filtered off and washed with isopropyl ether to afford the target compound (390 mg) as colorless crystals.

mp: 164–166° C. $^1$H-NMR (270 MHz, CDCl$_3$): δ (ppm) 2.30 (3H, s), 3.80 (3H, s), 3.94–3.98 (2H, m), 4.32–4.35 (2H, m), 6.99 (2H, d, J=8.5 Hz), 7.55 (2H, d, J=8.5 Hz), 7.56 (2H, d, J=8.5 Hz), 7.68 (2H, d, J=8.5 Hz).

Reference Example 24

Ethyl 2-(4-chlorophenoxy)-3-(4-hydroxyphenyl)propionate

Reference Example 24(a)

Ethyl 3-(4-benzyloxyphenyl)lactate

To a solution of ethyl 3-(4-hydroxyphenyl)lactate (22.4 g) in N,N-dimethylformamide (220 ml) were added benzyl bromide (21.9 g) and calcium carbonate (35.3 g), and the reaction mixture was stirred at 50° C. for 2 hours. The reaction solution was partitioned between ethyl acetate and water, and then the separated ethyl acetate layer was dried over anhydrous magnesium sulfate and concentrated under reduced pressure. The residue was purified by chromatography on a silica gel column (eluant; hexane/ethyl acetate=7/3) to give the target compound (31.0 g) as a pale yellow oil.

Reference Example 24(b)

Ethyl 3-(4-benzyloxyphenyl)-2-methanesulfonyloxypropionate

To a solution of ethyl 3-(4-benzyloxyphenyl)lactate (3.32 g) obtained from Reference example 24(a) in anhydrous dichloromethane (30 ml) was added methanesulfonyl chloride (0.94 ml), and then triethylamine (2.47 ml) was added dropwise thereto in an ice bath. The reaction solution was stirred for 3 hours at room temperature and then concentrated under reduced pressure. The residue was partitioned between ethyl acetate and water, and the separated ethyl acetate layer was dried over anhydrous magnesium sulfate and concentrated under reduced pressure. The residue was crystallized from hexane to afford the target compound (3.60 g) as colorless crystals.

mp: 81–83° C. $^1$H-NMR (270 MHz, CDCl$_3$): δ (ppm) 1.27 (3H, t, J=7.0 Hz), 2.80 (3H, s), 3.02–3.29 (2H, m), 4.24 (2H, q, J=7.0 Hz), 5.05 (2H, s), 5.05–5.14 (1H, m), 6.93 (2H, d, J=8.5 Hz), 7.17 (2H, d, J=8.5 Hz), 7.28–7.45 (5H, m).

Reference Example 24(c)

Ethyl 3-(4-benzyloxyphenyl)-2-(4-chlorophenoxy) propionate

To a solution of ethyl 3-(4-benzyloxyphenyl)-2-methanesulfonyloxypropionate (8.82 g) obtained from Reference example 24(b) and 4-chlorophenol (3.00 g) in N,N-dimethylformamide (110 ml) was added potassium carbonate (6.44 g), and the mixture was stirred at 70° C. for 16 hours. The reaction solution was partitioned between ethyl acetate and water, and then the ethyl acetate layer was dried over anhydrous magnesium sulfate and concentrated under reduced pressure. The residue was purified by chromatography on a silica gel column (eluant; hexane/ethyl acetate=9/1) to afford the target compound (5.99 g) as colorless crystals.

mp: 63–64° C. $^1$H-NMR (270 MHz, CDCl$_3$): δ (ppm) 1.18 (3H, t, J=7.0 Hz), 3.17 (2H, d, J=6.5 Hz), 4.16 (2H, q, J=7.0 Hz), 4.69 (1H, t, J=6.5 Hz), 5.04 (2H, s), 6.75 (2H, d, J=9.0 Hz), 6.91 (2H, d, J=8.5 Hz), 7.13–7.23 (4H, m), 7.25–7.55 (5H, m).

Reference Example 24(d)

Ethyl 2-(4-chlorophenoxy)-3-(4-hydroxyphenyl)propionate

Ethyl 3-(4-benzyloxyphenyl)-2-(4-chlorophenoxy)propionate (5.99 g) obtained from Reference example 24(c) was dissolved in a hydrogen bromide acetic acid solution (25%, 60 ml), and the mixture was stirred for 3 hours at room temperature. The resulting solution was concentrated under reduced pressure, then the residue was dissolved in ethanol (70 ml), and potassium carbonate (4.68 g) was added thereto, and the mixture was stirred for 4 hours at room temperature. The reaction solution was concentrated under reduced pressure. The residue was partitioned between ethyl acetate and water, and then the separated ethyl acetate layer was dried over anhydrous magnesium sulfate and concentrated under reduced pressure. The residue was purified by chromatography on a silica gel column (eluant; hexane/ethyl acetate=9/1~4/1) to give the target compound (3.85 g) as colorless crystals.

mp: 90–93° C. $^1$H-NMR (270 MHz, CDCl$_3$): δ (ppm) 1.19 (3H, t, J=7.0 Hz), 3.16 (2H, d, J=6.5 Hz), 4.17 (2H, q, J=7.0 Hz), 4.69 (1H, t, J=6.5 Hz), 4.95 (1H, brs), 6.76 (4H, d, J=8.5 Hz) 7.15 (2H, d, J=8.5 Hz), 7.18 (2H, d, J=8.5 Hz).

Reference Example 25

Ethyl 2-(4-fluorophenoxy)-3-(4-hydroxyphenyl)propionate

Reference Example 25(a)

Ethyl 3-(4-benzyloxyphenyl)-2-(4-fluorophenoxy) propionate

A solution of diethyl azodicarboxylate (40% toluene solution, 6.40 ml) in toluene (3.0 ml) was added dropwise at room temperature to a solution of ethyl 3-(4-benzyloxyphenyl)lactate (10.0 g) obtained from Reference example 24(a), 4-fluorophenol (4.15 g) and triphenylphosphine (10.6 g) in toluene (10 ml). The reaction mixture was stirred for 2 hours at room temperature and then concentrated under reduced pressure. The residue was purified by chromatography on a silica gel column (eluant; dichloromethane/ethyl acetate=3/2) to afford the target compound (7.00 g) as a colorless oil.

$^1$H-NMR (270 MHz, CDCl$_3$): δ (ppm) 1.18 (3H, t, J=7.0 Hz), 3.16 (2H, d, J=6.5 Hz), 4.16 (2H, q, J=7.0 Hz), 4.66 (1H, t, J=6.5 Hz), 5.04 (2H, s), 6.72–6.80 (2H, m), 6.89–6.97 (4H, m), 7.21 (2H, d, J=8.5 Hz), 7.31–7.48 (5H, m).

Reference Example 25(b)

Ethyl 2-(4-fluorophenoxy)-3-(4-hydroxyphenyl)propionate

To a hydrogen bromide.acetic acid solution (25%, 70 ml) was added ethyl 3-(4-benzyloxyphenyl)-2-(4-fluorophenoxy)propionate (7.00 g) obtained from Reference example 25(a), and the reaction solution was stirred for 3 hours at room temperature. The reaction solution was concentrated under reduced pressure, then the residue was dissolved in ethanol (70 ml), and potassium carbonate (6.90 g) was added thereto followed by stirring for 4 hours at room temperature. The reaction solution was concentrated under reduced pressure, and the residue was partitioned between ethyl acetate and water. The separated ethyl acetate layer was dried over anhydrous magnesium sulfate and concentrated under reduced pressure. The residue was purified by chromatography on a silica gel-column (eluant; hexane/ethyl acetate=9/1~4/1) to give the target compound (2.75 g) as a white powder.

mp: 80~81° C. $^1$H-NMR (270 MHz, CDCl$_3$): δ (ppm) 1.19 (3H, t, J=7.0 Hz), 3.15 (2H, d, J=6.5 Hz), 4.17 (2H, q, J=7.0 Hz), 4.65 (1H, t, J=6.5 Hz), 4.76 (1H, s), 6.71–6.80 (4H, m), 6.87–6.95 (2H, m), 7.16 (2H, d, J=8.5 Hz).

Reference Example 26

2-[[1-(4'-Fluoro-4-biphenylyl)ethylidene]aminoxy] ethyl methanesulfonate

Reference Example 26(a)

2-[[1-(4'-Fluoro-4-biphenylyl)ethylidene]aminoxy] ethanol

The target compound (3.84 g) was obtained as white crystals by carrying out the reaction and the post-treatment according to Reference examples 1(c) and 1(d) of WO 97/37970(EP 916651A) using 2-(2-bromoethoxy)tetrahydropyran (6.84 g), 4'-(4-fluorophenyl)acetophenone oxime (5.00 g), potassium carbonate (6.02 g) and a catalytic amount of p-toluenesulfonic acid monohydrate.

mp: 131–133° C. $^1$H-NMR (270 MHz, CDCl$_3$): δ (ppm) 2.30 (3H, s), 3.96 (2H, t, J=4.5 Hz), 4.34 (2H, t, J=4.5 Hz), 7.14 (2H, t, J=8.5 Hz), 7.53–7.59 (4H, m), 7.69 (2H, d, J=8.5 Hz).

Reference Example 26(b)

2-[[1-(4'-Fluoro-4-biphenylyl)ethylidene]aminoxy] ethyl methanesulfonate

Triethylamine (2.83 ml) was added dropwise at 0° C. to a solution of methanesulfonyl chloride (1.15 ml) and 2-[[1-(4'-fluoro-4-biphenylyl)ethylidene]aminoxy]ethanol (3.70 g) obtained from Reference example 26(a) in dichloromethane (40 ml), and the reaction mixture was stirred at room temperature for 2 hours. The reaction solution was concentrated under reduced pressure, and the residue was partitioned between ethyl acetate and water. The ethyl acetate layer was washed with a saturated aqueous sodium chloride solution, dried over anhydrous magnesium sulfate, and concentrated under reduced pressure. The obtained crystals were filtered off and washed with hexane and isopropyl ether to afford the target compound (4.70 g) as colorless crystals.

mp: 103–106° C. $^1$H-NMR (270 MHz, CDCl$_3$): δ (ppm) 2.29 (3H, s), 3.04 (3H, s), 4.46 (2H, t, J=4.5 Hz), 4.56 (2H, t, J=4.5 Hz), 7.14 (2H, t, J=8.5 Hz), 7.54–7.59 (4H, m), 7.72 (2H, d, J=8.5 Hz).

INDUSTRIAL APPLICABILITY

According to the present invention, side effects such as cardiac enlargement, edema, retention of body fluid and hydrothorax elicited by an insulin sensitizer can be prevented or treated by administration of a preventing or treating agent for diabetes mellitus comprising an insulin sensitizer and a diuretic.

Furthermore, in co-administration with the insulin sensitizer, amiloride, which is an ENaC inhibitor, exerted more potent effects than those predicted from its diuretic action. The reason that the ENaC inhibitor showed such a potent action is believed to be that the insulin sensitizer enhances ENaC activation and thus the ENaC inhibitor exerts potent action by co-administration with the insulin sensitizer.

What is claimed is:

1. A pharmaceutical composition comprising a diuretic and an insulin sensitizer in ratio of amount by weight of 1:200 to 200:1, wherein said insulin sensitizer is 5-[4-(6-methoxy-1-methyl-1H-benzimidazol-2-ylmethoxy)benzyl]thiazolidine-2,4-dione or a pharmacologically acceptable salt thereof; and said diuretic is amiloride.

* * * * *